(12) United States Patent
Dickhaut et al.

(10) Patent No.: US 11,542,280 B2
(45) Date of Patent: Jan. 3, 2023

(54) SUBSTITUTED PYRIMIDINIUM COMPOUNDS AND DERIVATIVES FOR COMBATING ANIMAL PESTS

(71) Applicant: BASF SE, Ludwigshafen am Rhein (DE)

(72) Inventors: Joachim Dickhaut, Ludwigshafen (DE); Ashokkumar Adisechan, Navi Mumbai (IN); Gopal Krishna Datta, Goettingen (DE); Olesya Kuzmina, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 271 days.

(21) Appl. No.: 16/624,053

(22) PCT Filed: Jun. 18, 2018

(86) PCT No.: PCT/EP2018/066039
§ 371 (c)(1),
(2) Date: Dec. 18, 2019

(87) PCT Pub. No.: WO2018/234202
PCT Pub. Date: Dec. 27, 2018

(65) Prior Publication Data
US 2020/0131198 A1  Apr. 30, 2020

(30) Foreign Application Priority Data

Jun. 19, 2017 (IN) .............................. 201721021381
Sep. 6, 2017 (EP) ..................................... 17189534

(51) Int. Cl.
| | |
|---|---|
| *A01N 43/90* | (2006.01) |
| *C07D 471/04* | (2006.01) |
| *C07D 487/04* | (2006.01) |
| *C07D 498/04* | (2006.01) |
| *C07D 513/04* | (2006.01) |

(52) U.S. Cl.
CPC .......... *C07D 513/04* (2013.01); *A01N 43/90* (2013.01); *C07D 471/04* (2013.01); *C07D 487/04* (2013.01); *C07D 498/04* (2013.01)

(58) Field of Classification Search
None
See application file for complete search history.

(56) References Cited

FOREIGN PATENT DOCUMENTS

| | | |
|---|---|---|
| WO | WO-2009/099929 A1 | 8/2009 |
| WO | WO-2011/017342 A2 | 2/2011 |
| WO | WO-2011/017347 A2 | 2/2011 |
| WO | WO-2014/167084 A1 | 10/2014 |
| WO | WO-2016/044431 A1 | 3/2016 |
| WO | WO-2016/171053 A1 | 10/2016 |
| WO | WO-2018/177970 A1 | 10/2018 |
| WO | WO-2018/197541 A1 | 11/2018 |
| WO | WO-2018/202654 A1 | 11/2018 |
| WO | WO-2018/229202 A1 | 12/2018 |
| WO | WO-2018/234202 A1 | 12/2018 |
| WO | WO-2019/042932 A1 | 3/2019 |

OTHER PUBLICATIONS

European Search Report for EP Patent Application No. 17189534.5, dated Jun. 6, 2018, 5 pages.
International Search Report for PCT Patent Application No. PCT/EP2018/066039, dated Nov. 9, 2018, 6 pages.

*Primary Examiner* — Alton N Pryor
(74) *Attorney, Agent, or Firm* — Marshall, Gerstein & Borun LLP

(57) ABSTRACT

The present invention relates to substituted pyrimidinium compounds of formula (I), to the stereoisomers, salts, tautomers and N-oxides thereof and to compositions comprising such compounds. The invention also relates to methods and uses of these substituted pyrimidinium compounds and of compositions thereof, for combating and controlling animal pests. Furthermore the invention relates also to pesticidal methods of applying such substituted pyrimidinium compounds.
The substituted pyrimidinium compounds of the present invention are defined by the following general formula (I)

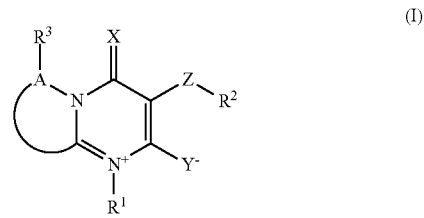

wherein X, Y, Z, $R^1$, $R^2$, A and $R^3$ are defined as in the description.

20 Claims, No Drawings

SUBSTITUTED PYRIMIDINIUM COMPOUNDS AND DERIVATIVES FOR COMBATING ANIMAL PESTS

This application is a National Stage application of International Application No. PCT/EP2018/066039, filed Jun. 18, 2018. This application also claims priority under 35 U.S.C. § 119 to European Patent Application No. 17189534.5, filed Sep. 6, 2017 and Indian Patent Application No. 201721021381 filed Jun. 19, 2017.

The present invention relates to insecticidal substituted pyrimidinium compounds and/or to the compositions comprising such compounds for combating invertebrate pests. The invention also relates to pesticidal methods, to uses and to applications of substituted pyrimidinium compounds as described in the present invention and the stereoisomers, salts, tautomers and N-oxides thereof as well as compositions comprising them.

Invertebrate pests and in particular insects, arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control insects, arachnids and nematodes.

It has been found that these objectives can be achieved by substituted pyrimidinium compounds of the general formula (I), as defined below, including their stereoisomers, their salts, in particular their agriculturally or veterinary acceptable salts, their tautomers and their N-oxides.

Therefore, in a first aspect the present invention provides substituted pyrimidinium compounds of formula (I) or a composition comprising at least one substituted pyrimidinium compound of formula (I)

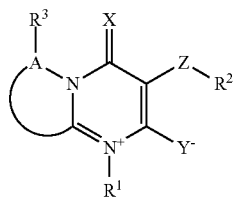

(I)

wherein

X, Y are each independently O or S;

Z is a direct bond, O, $S(O)_m$, $NR^b$, $C(R^aR^{aa})O$, $C(=X^1)$, $C(=X^1)Y^1$, or $Y^1C(=X^1)$;

$X^1$ is O, S, or $NR^b$;

$Y^1$ is O, S, or $NR^c$;

A is CH or N and, wherein the nitrogen of the pyrimidinium ring taken together with the contiguous linking carbon atom and A as depicted in formula (I), form a four- to seven-membered ring, wherein each remaining ring member is selected from carbon atoms and up to 3 heteroatoms independently selected from up to 2 O, up to 2 S, and up to 3 $N(R^c)_p$, wherein up to 2 carbon atom ring members are independently selected from C(=O) and C(=S), and the sulfur atom ring members are independently selected from $S(=O)_m$, wherein each ring may be substituted with up to 3 $R^a$;

$R^3$ is $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_7$-cycloalkyl, $C_3$-$C_7$-halocycloalkyl, $C_4$-$C_8$-alkylcycloalkyl, $C_4$-$C_8$-haloalkylcycloalkyl, $C_4$-$C_8$-cycloalkylalkyl, $C_4$-$C_8$-halocycloalkylalkyl, $C_1$-$C_6$-alkoxy, $C_1$-$C_6$-haloalkoxy, $C_2$-$C_6$-alkylcarbonyl, $C_2$-$C_6$-haloalkylcarbonyl, each substituted with at least one substituent selected from CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$ $NR^bC(=O)NR^bR^c$, $C(=S)NR^bR^c$, $S(O)_rR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$ $NR^bC(=NR^b)NR^bR^c$, $NR^bNR^bC(=X^2)NR^bR^c$, $NR^bNR^bSO_2NR^bR^c$, or $N=S(=O)_pR^cR^c$, or two geminally bound groups $R^3$ together may form a group selected from =O, =S, =$CR^bR^c$, =$NR^c$, =$NOR^c$, and =$NNR^cR^c$;

or $R^3$ is phenyl optionally substituted with one or more substituents selected from halogen, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$ $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$ $NR^bC(=NR^b)NR^bR^c$, $NR^bNR^bC(=X^2)NR^bR^c$, $NR^bNR^bSO_2NR^bR^c$, or $N=S(=O)_pR^cR^c$, or $R^3$ is phenyl optionally substituted with one or more substituents selected from $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_7$-cycloalkyl, $C_3$-$C_7$-halocycloalkyl, $C_4$-$C_8$-alkylcycloalkyl, $C_4$-$C_8$-haloalkylcycloalkyl, $C_4$-$C_8$-cycloalkylalkyl, $C_4$-$C_8$-halocycloalkylalkyl, $C_1$-$C_6$-alkoxy, $C_1$-$C_6$-haloalkoxy, $C_2$-$C_6$-alkylcarbonyl, $C_2$-$C_6$-haloalkylcarbonyl, which groups may optionally be substituted with halogen, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$ $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$ $NR^bC(=NR^b)NR^bR^c$, $NR^bNR^bC(=X^2)NR^bR^c$, $NR^bNR^bSO_2NR^bR^c$, or $N=S(=O)_pR^cR^c$;

$R^1$ is hydrogen, $C_1$-$C_8$-alkyl, $C_2$-$C_8$-alkenyl, $C_2$-$C_8$-alkynyl, $C_3$-$C_{10}$-cycloalkyl, $C_4$-$C_{10}$-cycloalkenyl, $C_5$-$C_{14}$-cycloalkylcycloalkyl or $R^1$ may form a three- to eleven-membered saturated, or partially unsaturated or aromatic carbo- or heterocyclic ring or ring system, which may contain 1 to 4 heteroatoms selected from $N(R^e)_p$, O, and S, wherein S may be oxidized, and wherein the aforementioned groups and the carbo- or heterocyclic rings system may be unsubstituted, partially or fully substituted with $R^a$; or $R^1$ is $C(=O)R^b$, $C(=O)OR^e$, $NR^bR^c$, $C(=O)NR^bR^c$, $C(=S)NR^bR^c$, $SO_2NR^bR^c$, $OC(=O)R^c$, $OC(=O)OR^e$, $OC(=O)NR^bR^e$, $N(R^c)C(=O)R^c$, $N(R^c)C(=O)OR^e$, $N(R^c)C(=O)NR^bR^c$, $NR^cSO_2R^b$, $NR^cSO_2NR^bR^c$, $Si(R^d)_3$, $C(=NR^c)R^c$, $C(=NOR^c)R^c$, $C(=NNR^bR^c)R^c$, $C(=NN(C(=O)R^b)R^c)R^c$, $C(=NN(C(=O)OR^e)(R^c)_2$, $S(=O)_o(=NR^b)_qR^c$, or $N=CR^bR^c$;

$R^a$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$ $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $N=S(=O)_pR^cR^c$, $S(=O)_o(=NR^b)_qR^c$, $SF_5$, OCN, SCN, $Si(R^d)_3$ or a three- to six-membered saturated, or partially unsaturated or aromatic carbo- or heterocyclic ring, which may contain 1 to 3 heteroatoms selected from $N-(R^e)_p$, O, and S which may be oxidized, and wherein the aforementioned groups and the carbo- or heterocyclic ring may be partially or fully substituted with $R^{aa}$, or two geminally bound groups $R^a$ together may form a group selected from =O, =S, =$CR^bR^c$, =$NR^c$, =$NOR^c$, and =$NNR^cR^c$;

$R^{aa}$ is each independently halogen, $C_1$-$C_6$-alkyl, $C_1$-$C_6$-haloalkyl, $C_1$-$C_6$-alkoxy or $C_1$-$C_6$-haloalkoxy;

$R^b$ is each independently hydrogen, $C_1$-$C_6$-alkyl, $C_1$-$C_6$-haloalkyl, $C_1$-$C_6$-alkoxy, $C_1$-$C_6$-haloalkoxy or a three- to six-membered saturated, or partially unsaturated or aromatic carbo- or heterocyclic ring, which may contain 1 to 3 heteroatoms selected from $N(R^c)_p$, O, and S, wherein S may be oxidized and which carbo- or heterocyclic ring may be partially or fully substituted with $R^{aa}$;

$R^c$ is each independently hydrogen, $C_1$-$C_4$-alkyl, $C_1$-$C_4$-haloalkyl, $C_1$-$C_4$-alkylcarbonyl, $C_1$-$C_6$ cycloalkyl, or a three- to six-membered saturated, partially unsaturated or aromatic carbo- or heterocyclic ring, which may contain 1 to 3 heteroatoms selected from $N(R^{aa})_p$, O and S, wherein S may be oxidized and wherein the carbo- or heterocyclic ring may be partially or fully substituted with $R^{aa}$;

wherein two geminally bound groups $R^bR^b$, $R^cR^b$ or $R^cR^c$ together with the atom to which they are bound, may form a 3-, 4-, 5-, 6- or 7-membered saturated, partially unsaturated or aromatic carbo- or heterocyclic ring, which may contain 1 to 2 heteroatoms or heteroatoms groups selected from N, O, S, NO, SO and $SO_2$ and wherein the carbo- or heterocyclic ring may be partially or fully substituted with $R^4$;

$R^d$ is each independently hydrogen, phenyl, $C_1$-$C_6$-alkyl, $C_2$-$C_6$-alkenyl, $C_2$-$C_6$-alkynyl, $C_3$-$C_8$-cycloalkyl, or $C_1$-$C_6$-alkoxyalkyl, wherein the above mentioned groups may be substituted with one or more halogen;

$R^e$ is each independently, $C_1$-$C_4$-alkyl, $C_1$-$C_4$-haloalkyl, $C_1$-$C_4$-alkylcarbonyl, $C_1$-$C_6$ cycloalkyl, or a three- to six-membered saturated, partially unsaturated or aromatic carbo- or heterocyclic ring, which may contain 1 to 3 heteroatoms selected from $N(R^{aa})_p$, O and S, wherein S may be oxidized and wherein the carbo- or heterocyclic ring may be partially or fully substituted with $R^{aa}$;

n is 0, 1 or 2;
m is 0, 1, or 2;
p is 0 or 1;

$R^2$ is H, halogen, CN, $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, or $C_3$-$C_6$ cycloalkenyl, wherein the aforementioned groups may be unsubstituted, partially, or fully substituted with $R^{2a}$, or $R^2$ may form a carbo- or heterocyclic three- to ten-membered ring or a seven- to eleven-membered rings system, which ring or ring system may be saturated, partially unsaturated, or aromatic, and which ring or ring system may contain 1 to 4 heteroatoms selected from $N(R^e)_p$, O, and S, wherein S may be oxidized, and wherein the carbo- or heterocyclic ring or rings system may be unsubstituted, partially, or fully substituted with $R^{2a}$;

with the proviso that if $R^2$ is halogen or CN, then Z is a direct bond;

$R^{2a}$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$ $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$ $NR^bC(=NR^b)NR^bR^c$, $NR^bNR^bC(=X^2)NR^bR^c$, $NR^bNR^bSO_2NR^bR^c$, $N=S(=O)_pR^cR^c$, or a three- to six-membered saturated, or partially unsaturated or aromatic carbo- or heterocyclic ring, which may contain 1 to 3 heteroatoms selected from $N-(R^c)_p$, O, and S, wherein S may be oxidized, and wherein the aforementioned groups and the carbo- or heterocyclic ring may be partially or fully substituted with $R^{2aa}$; or two geminally bound groups $R^{2a}$ together may form a group selected from =O, =S, =$CR^bR^c$, =$NR^c$, =$NOR^c$, and =$NNR^cR^c$;

$R^{2aa}$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$ $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or $N=S(=O)_pR^cR^c$, or two geminally bound groups $R^{2aa}$ together may form a group selected from =O, =S, =$CR^bR^c$, =$NR^c$, =$NOR^c$, and =$NNR^cR^c$;

$X^2$ is independently O or S;

$R^4$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$ $NR^bC(=O)NR^bR^c$, $C(=S)NR^bR^c$, $S(O)_nR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or $N=S(=O)_pR^cR^c$, or two geminally bound groups $R^4$ together may form a group selected from $=O$, $=S$, $=CR^bR^c$, $=NR^c$, $=NOR^c$, and $=NNR^cR^c$;

or a stereoisomer, tautomer, salt, or N-oxide thereof.

WO2014/167084 describes certain substituted pyrimidinium compounds with heterocyclic substituents for combating invertebrate pests.

WO2016/171053 describes certain substituted pyrido[1,2-a]pyrimidinium compounds.

The substituted pyrimidinium compounds of formula (I) according to the present invention, with their characteristic substitution pattern, have not yet been described for pesticidal uses or pesticidal applications in agricultural industry or veterinary practice.

The substituted pyrimidinium compounds of the formula (I), and their agriculturally acceptable salts are highly active against animal pest, i.e. harmful arthropodes and nematodes, especially against insects and acaridae which are difficult to control by other means.

Moreover, the present invention relates to and includes the following embodiments:

compositions comprising at least one compound of formula (I) as defined above;

agricultural and veterinary compositions comprising an amount of at least one compound of formula (I) or an enantiomer, diasteromer or salt thereof as defined above;

a method for combating invertebrate pests, infestation, or infection by invertebrate pests, which method comprises contacting said pest or its food supply, habitat or breeding grounds with a pesticidally effective amount of at least one compound of formula (I) as defined above or a composition thereof;

a method for controlling invertebrate pests, infestation, or infection by invertebrate pests, which method comprises contacting said pest or its food supply, habitat or breeding grounds with a pesticidally effective amount of at least one compound of formula (I) as defined above or a composition comprising at least one compound of formula (I);

a method for preventing or protecting against invertebrate pests comprising contacting the invertebrate pests, or their food supply, habitat or breeding grounds with a substituted pyrimidinium compounds of the general formula (I) as defined above or a composition comprising at least one compound of formula (I) as defined above or a composition comprising at least one compound of formula (I);

a method for protecting crops, plants, plant propagation material and/or growing plants from attack or infestation by invertebrate pests comprising contacting or treating the crops, plants, plant propagation material and growing plants, or soil, material, surface, space, area or water in which the crops, plants, plant propagation material is stored or the plant is growing, with a pesticidally effective amount of at least one compound of formula (I) as defined above or a composition comprising at least one compound of formula (I);

a non-therapeutic method for treating animals infested or infected by parasites or preventing animals of getting infected or infested by parasites or protecting animals against infestation or infection by parasites which comprises orally, topically or parenterally administering or applying to the animals a parasiticidally effective amount of a compound of formula (I) as defined above or a composition comprising at least one compound of formula (I);

a method for treating, controlling, preventing or protecting animals against infestation or infection by parasites by administering or applying orally, topically or parenterally to the animals a substituted pyrimidinium compound of the general formula (I) as defined above or a composition comprising at least one compound of formula (I);

seed comprising a compound of formula (I) as defined above, in an amount of from 0.1 g to 10 kg per 100 kg of seed;

the use of the compounds of formula (I) as defined above for protecting growing plants or plant propagation material from attack or infestation by invertebrate pests;

the use of compounds of formula (I) or the enantiomers, diastereomers or veterinary acceptable salts thereof for combating parasites in and on animals;

a process for the preparation of a veterinary composition for treating, controlling, preventing or protecting animals against infestation or infection by parasites which comprises adding a parasiticidally effective amount of an compound of formula (I) or the enantiomers, diastereomers and/or veterinary acceptable salt thereof to a carrier composition suitable for veterinary use;

the use of a compound of formula (I) or the enantiomers, diastereomers and/or veterinary acceptable salt thereof for the preparation of a medicament for treating, controlling, preventing or protecting animals against infestation or infection by parasites.

All the compounds of the present invention including if applicable their stereoisomers, their tautomers, their salts or their N-oxides as well as compositions thereof are particularly useful for controlling invertebrate pests, in particular for controlling arthropods and nematodes and especially insects. Therefore, the invention relates to the use of a compound as disclosed in the present invention, for combating or controlling invertebrate pests, in particular invertebrate pests of the group of insects, arachnids or nematodes.

The term "compound(s) according to the invention" or "compound(s) of formula (I)" as used in the present invention refers to and comprises the compound(s) as defined herein and/or stereoisomer(s), salt(s), tautomer(s) or N-oxide(s) thereof. The term "compound(s) of the present invention" is to be understood as equivalent to the term "compound(s) according to the invention" therefore also comprising stereoisomer(s), salt(s), tautomer(s) or N-oxide(s) of compounds of formula (I).

The term composition(s) according to the invention or "composition(s) of the present invention" encompasses composition(s) comprising at least one compound of formula (I) according to the invention as defined above, therefore also including a stereoisomer, an agriculturally or veterinary acceptable salt, tautomer or an N-oxide of the compounds of formula (I).

The compounds of the formula (I) are present in mesomeric forms.

These forms may be expressed in different isoelectronic formulae, each having the formal positive and negative charges on different atoms (as shown below). The present invention extends to all representative isoelectronic structures of compounds of formula I.

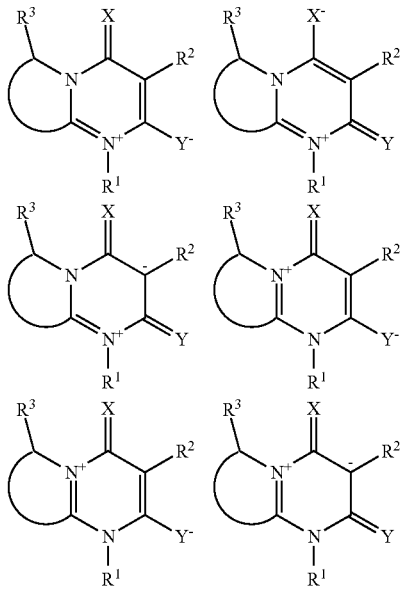

The compounds of the formula (I) have one or more centers of chirality, i.e. they are present as mixtures of enantiomers or diastereomers. The invention provides both the single pure enantiomers or pure diastereomers of the compounds of formula (I), and their mixtures and the use according to the invention of the pure enantiomers or pure diastereomers of the compound of formula (I) or its mixtures. Suitable compounds of the formula (I) also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula (I), i.e. to single enantiomers or diastereomers, as well as to mixtures thereof.

In one embodiment of the invention, the compounds of formula (I) have the following stereochemistry as in formula (I-R):

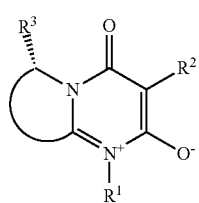
(I-R)

In another embodiment of the invention, the compounds of formula (I) have the following stereochemistry as in formula (I-S):

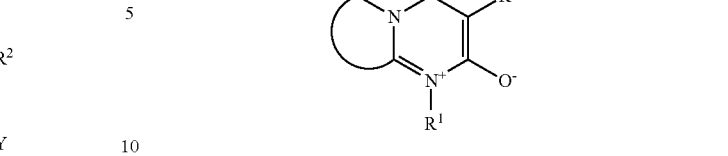
(I-S)

The compounds of the present invention may be amorphous or may exist in one or more different crystalline states (polymorphs) or modifications which may have a different macroscopic properties such as stability or show different biological properties such as activities. The present invention includes both amorphous and crystalline compounds of the formula (I), mixtures of different crystalline states or modifications of the respective compound I, as well as amorphous or crystalline salts thereof.

Salts of the compounds of the formula (I) are preferably agriculturally and/or veterinary acceptable salts. They can be formed in a customary method, e.g. by reacting the compound with an acid of the anion in question if the compound of formula (I) has a basic functionality or by reacting an acidic compound of formula (I) with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The term "N-oxide" includes any compound of the present invention which has at least one tertiary nitrogen atom that is oxidized to an N-oxide moiety.

The organic moieties groups mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen (or sulfur linkages, respectively) at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkyl-sulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_n$-$C_m$-alkoxy-$C_n$-$C_m$-alkyl" as used herein refers to alkyl having n to m carbon atoms, e.g. like specific examples mentioned above, wherein one hydrogen atom of the alkyl radical is replaced by an $C_n$-$C_m$-alkoxy group; wherein the value of n and m of the alkoxy group are independently chosen from that of the alkyl group.

The suffix "-carbonyl" in a group or "C(=O)" denotes in each case that the group is bound to the remainder of the molecule via a carbonyl C=O group. This is the case e.g. in alkylcarbonyl, haloalkylcarbonyl, aminocarbonyl, alkylaminocarbonyl, dialkylaminocarbonyl, alkoxycarbonyl, haloalkoxycarbonyl.

The term "aryl" as used herein refers to a mono-, bi- or tricyclic aromatic hydrocarbon radical such as phenyl or naphthyl, in particular phenyl (also referred as to $C_6H_5$ as substituent).

The term "ring system" denotes two or more directly connected rings.

The term "$C_3$-$C_m$-cycloalkyl" as used herein refers to a monocyclic ring of 3- to m-membered saturated cycloaliphatic radicals, e.g. cyclopropyl, cyclobutyl, cyclopentyl, cyclohexyl, cycloheptyl, cyclooctyl and cyclodecyl.

The term "alkylcycloalkyl" denotes as well as the term "alkyl which may be substituted with cycloalkyl" an alkyl group which is substituted with a cycloalkyl ring, wherein alkyl and cycloakyl are as herein defined.

The term "cycloalkylalkyl" denotes as well as the term "cycloalkyl which may be substituted with alkyl" a cycloalkyl ring which is substituted with an alkyl group, wherein alkyl and cycloakyl are as herein defined.

The term "alkylcycloalkylalkyl" denotes as well as the term "alkylcycloalkyl which may be substituted with alkyl" an alkylcycloalkyl group which is substituted with an alkyl, wherein alkyl and alkylcycloakyl are as herein defined.

The term "$C_3$-$C_m$-cycloalkenyl" as used herein refers to a monocyclic ring of 3- to m-membered partially unsaturated cycloaliphatic radicals.

The term "cycloalkylcycloalkyl" denotes as well as the term "cycloalkyl which may be substituted with cycloalkyl" a cycloalkyl substitution on another cycloalkyl ring, wherein each cycloalkyl ring independently has from 3 to 7 carbon atom ring members and the cycloalkyls are linked through one single bond or have one common carbon atom. Examples of cycloalkylcycloalkyl include cyclopropylcyclopropyl (e.g. 1,1'-bicyclopropyl-2-yl), cyclohexylcyclohexyl wherein the two rings are linked through one single common carbon atom (e.g. 1,1'-bicyclohexyl-2-yl), cyclohexylcyclopentyl wherein the two rings are linked through one single bond (e.g. 4-cyclopentylcyclohexyl) and their different stereoisomers such as (1R,2S)-1, 1'-bicyclopropyl-2-yl and (1R,2R)-1,1'-bicyclopropyl-2-yl.

The term "3- to 6-membered carbocyclic ring" as used herein refers to cyclopropane, cyclobutane, cyclopentane and cyclohexane rings.

The term "3-, 4-, 5-, 6- or 7-membered saturated, partially unsaturated or aromatic heterocyclic ring which may contain 1, 2, 3 or 4 heteroatoms" or "containing heteroatom groups", wherein those heteroatom(s) (group(s)) are selected from N (N-substituted groups), O and S (S-substituted groups) as used herein refers to monocyclic radicals, the monocyclic radicals being saturated, partially unsaturated or aromatic (completely unsaturated). The heterocyclic radical may be attached to the remainder of the molecule via a carbon ring member or via a nitrogen ring member.

Examples of 3-, 4-, 5-, 6- or 7-membered saturated heterocyclyl or heterocyclic rings include: oxiranyl, aziridinyl, azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin 5 yl, 1,2,4-thiadiazolidin-3-yl, 1,2,4-thiadiazolidin-5-yl, 1,2, 4-triazolidin-3-yl-1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like. Examples of 3-, 4-, 5-, 6- or 7-membered partially unsaturated heterocyclyl or heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin 3 yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H] azepin-1-, -2-, -3-, -4-, -5-, -6- or -7-yl, 3,4,5,6-tetrahydro [2H]azepin-2-, -3-, -4-, -5-, -6- or -7-yl, 2,3,4,7 tetrahydro [1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin 2, 3, 4, 5, 6 or -7 yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of 5- or 6-membered aromatic heterocyclic (hetaryl) or heteroaromatic rings are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

A "$C_2$-$C_m$-alkylene" is divalent branched or preferably unbranched saturated aliphatic chain having 2 to m, e.g. 2 to 7 carbon atoms, for example $CH_2CH_2$, $—CH(CH_3)—$, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$.

Embodiments and preferred compounds of the present invention for use in pesticidal methods and for insecticidal application purposes are outlined in the following paragraphs.

The remarks made below concerning preferred embodiments of the variables (substituents) of the compounds according to the invention, especially with respect to their substituents X, Y, Z, $X^1$, $X^2$, $Y^1$, A, $R^1$, $R^a$, $R^{aa}$, $R^b$, $R^c$, $R^d$, $R^e$, $R^2$, $R^{2a}$, $R^{2aa}$, $R^4$, m, n, p and $R^3$ are valid both on their own and, in particular, in every possible combination with each other and where applicable, the uses, the methods and the compositions according to the invention.

In a particular embodiment, the variables of the compounds of formula (I) have the following meanings, these meanings, both on their own and in combination with one another, being particular embodiments of the compounds of the formula (I):

In one preferred embodiment of the compounds of formula (I), X is O. These compounds correspond to the compounds of formula (I.1).

In a further embodiment of the compounds of the formula (I), X is S. These compounds correspond to the compounds of formula (I.2).

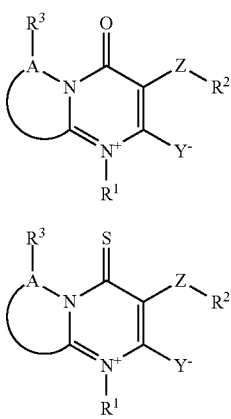

(I.1)

(I.2)

In another embodiment of the compounds of formula (I), Y is S. These compounds correspond to the compounds of formula (I.A).

In another embodiment of the compounds of formula (I), Y is O. These compounds correspond to the compounds of formula (I.B).

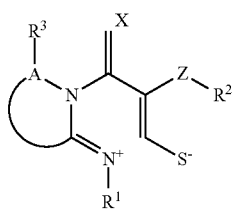

(I.A)

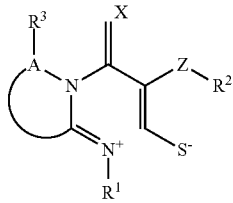

(I.B)

In another embodiment of the compounds of formula (I), Y is S and X is O. These compounds correspond to compounds of formula I.1.A:

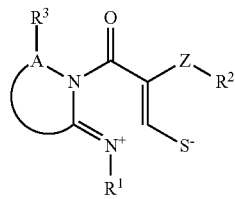

(I.1.A)

In another embodiment of the compounds of formula (I), Y is S and X is S. These compounds correspond to compounds of formula I.2.A.

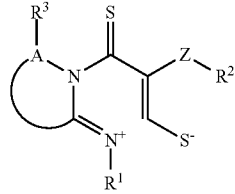

(I.2.A)

In another embodiment of the compounds of formula (I), Y is O and X is O. These compounds correspond to compounds of formula I.1.B.

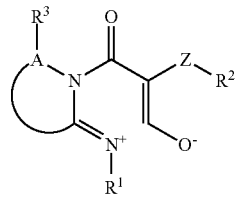

(I.1.B)

In another embodiment of the compounds of formula (I), Y is O and X is S. These compounds correspond to compounds of formula I.2.B.

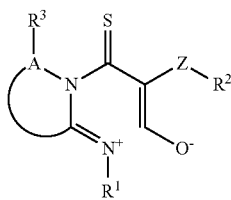

(I.2.B)

Within these embodiments, compounds of formula I.1.B are preferred.

In an embodiment of the compounds of formula (I), Z is a direct bond or $C(R^a R^{aa})O$.

In a further embodiment of the compounds of formula (I), Z is a direct bond.

In an embodiment of the compounds of formula (I), Z is O, $S(O)_m$, $NR^b$, $C(=X^1)$, $C(=X^1)Y^1$, or $Y^1C(=X^1)$. In a further embodiment, Z is O, $S(O)_m$, or $NR^b$. In another embodiment, Z is $C(=X^1)$, $C(=X^1)Y^1$, or $Y^1C(=X^1)$.

In an embodiment of the compounds of formula (I), $X^1$ is O.

In an embodiment of the compounds of formula (I), $X^1$ is S.

In an embodiment of the compounds of formula (I), $X^1$ is $NR^b$.

In an embodiment of the compounds of formula (I), $Y^1$ is O.

In an embodiment of the compounds of formula (I), $Y^1$ is S.

In an embodiment of the compounds of formula (I), $Y^1$ is $NR^c$.

In an embodiment of the compounds of formula (I), A is CH or N and, wherein the nitrogen of the pyrimidinium ring taken together with the contiguous linking carbon atom and A as depicted in formula (I), form a four- to seven-membered ring, wherein such ring is not an aromatic ring, and wherein each remaining ring member is selected from carbon atoms and up to 3 heteroatoms independently selected from up to 2 O, up to 2 S, and up to 3 $N(R^c)_p$, wherein up to 2 carbon atom ring members are independently selected from C(=O) and C(=S), and the sulfur atom ring members are independently selected from $S(=O)_m$, wherein each ring may be substituted with up to 3 $R^a$;

In an embodiment of the compounds of formula (I), A is CH and, wherein the nitrogen of the pyrimidinium ring taken together with the contiguous linking carbon atom and A as depicted in formula (I), form a four- to seven-membered ring, wherein such ring is not an aromatic ring, and wherein each remaining ring member is selected from carbon atoms and up to 3 heteroatoms independently selected from up to 2 O, up to 2 S, and up to 3 $N(R^c)_p$, wherein up to 2 carbon atom ring members are independently selected from C(=O) and C(=S), and the sulfur atom ring members are independently selected from $S(=O)_m$, wherein each ring may be substituted with up to 3 $R^a$;

In an embodiment of the compounds of formula (I), A is CH or N, and wherein the nitrogen of the pyrimidinium ring taken together with the contiguous linking carbon atom and A as depicted in formula (I), form a five or six membered ring, wherein each remaining ring member is selected from carbon atoms and up to one heteroatoms independently selected from O, S, and $N(R^c)_p$, wherein each ring may be substituted with up to one $R^a$, wherein $R^a$ has the meaning as hereunder described.

In an embodiment of the compounds of formula (I), A is CH or N, and wherein the nitrogen of the pyrimidinium ring taken together with the contiguous linking carbon atom and A as depicted in formula (I), form a five or six membered ring, wherein such ring is not an aromatic ring, and wherein each remaining ring member is selected from carbon atoms and up to one heteroatoms independently selected from O, S, and $N(R^c)_p$, wherein each ring may be substituted with up to one $R^a$, wherein $R^a$ has the meaning as hereunder described.

In a further embodiment of the compounds of formula (I), A is CH or N, and wherein the nitrogen of the pyrimidinium ring taken together with the contiguous linking carbon atom and A as depicted in formula (I), form a five membered ring, wherein each remaining ring member is selected from carbon atoms and up to one heteroatoms independently selected from O, S, and $N(R^c)_p$.

In a further embodiment of the compounds of formula (I), A is CH or N, and wherein the nitrogen of the pyrimidinium ring taken together with the contiguous linking carbon atom and A as depicted in formula (I), form a five membered ring, wherein such ring is not an aromatic ring, and wherein each remaining ring member is selected from carbon atoms and up to one heteroatoms independently selected from O, S, and $N(R^c)_p$.

In a further embodiment of the compounds of formula (I), A is CH or N, and wherein the nitrogen of the pyrimidinium ring taken together with the contiguous linking carbon atom and A as depicted in formula (I), form a six membered ring, wherein each remaining ring member is selected from carbon atoms and up to one heteroatoms independently selected from O, S, and $N(R^c)_p$.

In a further embodiment of the compounds of formula (I), A is CH or N, and wherein the nitrogen of the pyrimidinium ring taken together with the contiguous linking carbon atom and A as depicted in formula (I), form a six membered ring, wherein such ring is not an aromatic ring, and wherein each remaining ring member is selected from carbon atoms and up to one heteroatoms independently selected from O, S, and $N(R^c)_p$.

In a further embodiment of the compounds of formula (I), A is CH, and wherein the nitrogen of the pyrimidinium ring taken together with the contiguous linking carbon atom and A as depicted in formula (I), form a five membered ring, wherein each remaining ring member is selected from carbon atoms and up to one heteroatoms independently selected from O, S, and $N(R^c)_p$, wherein each ring may be substituted with up to one $R^a$, wherein $R^a$ has the meaning as hereunder described.

In a further embodiment of the compounds of formula (I), A is CH, and wherein the nitrogen of the pyrimidinium ring taken together with the contiguous linking carbon atom and A as depicted in formula (I), form a five membered ring, wherein such ring is not an aromatic ring, and wherein each remaining ring member is selected from carbon atoms and up to one heteroatoms independently selected from O, S, and $N(R^c)_p$, wherein each ring may be substituted with up to one $R^a$, wherein $R^a$ has the meaning as hereunder described.

In a further embodiment of the compounds of formula (I), A is CH, and wherein the nitrogen of the pyrimidinium ring taken together with the contiguous linking carbon atom and A as depicted in formula (I), form a five membered ring, wherein each remaining ring member is selected from carbon atoms and up to one heteroatoms independently selected from O and S, wherein each ring may be substituted with up to one $R^a$, wherein $R^a$ has the meaning as hereunder described.

In a further embodiment of the compounds of formula (I), A is CH, and wherein the nitrogen of the pyrimidinium ring taken together with the contiguous linking carbon atom and A as depicted in formula (I), form a five membered ring, wherein such ring is not an aromatic ring, and wherein each remaining ring member is selected from carbon atoms and up to one heteroatoms independently selected from O and S, wherein each ring may be substituted with up to one $R^a$, wherein $R^a$ has the meaning as hereunder described.

In a further embodiment of the compounds of formula (I), A is CH, and wherein the nitrogen of the pyrimidinium ring taken together with the contiguous linking carbon atom and A as depicted in formula (I), form a six membered ring, wherein each remaining ring member is selected from carbon atoms and up to one heteroatoms independently selected from O, S, and $N(R^c)_p$, wherein each ring may be substituted with up to one $R^a$, wherein $R^a$ has the meaning as hereunder described.

In a further embodiment of the compounds of formula (I), A is CH, and wherein the nitrogen of the pyrimidinium ring taken together with the contiguous linking carbon atom and A as depicted in formula (I), form a six membered ring, wherein each remaining ring member is selected from carbon atoms and up to one heteroatoms independently selected from O, S, and $N(R^c)_p$, wherein each ring may be substituted with up to one $R^a$, wherein $R^a$ has the meaning as hereunder described.

In a further embodiment of the compounds of formula (I), A is CH, and wherein the nitrogen of the pyrimidinium ring taken together with the contiguous linking carbon atom and A as depicted in formula (I), form a six membered ring, wherein such ring is not an aromatic ring, and wherein each remaining ring member is selected from carbon atoms and up to one heteroatoms independently selected from O and S, wherein each ring may be substituted with up to one $R^a$, wherein $R^a$ has the meaning as hereunder described.

In a further embodiment, preferred are compounds of formula (I), wherein A is CH, and wherein the nitrogen of the pyrimidinium ring taken together with the contiguous linking carbon atom and A as depicted in formula (I), form a five or six membered ring resulting in the compounds of formula (II) selected from the group of compounds of formulae II-1 to II-16

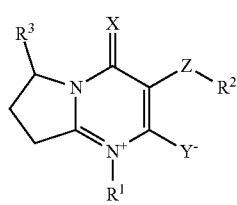

II-1

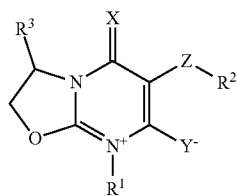

II-2

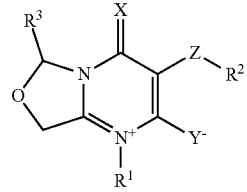

II-3

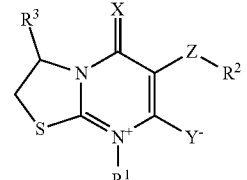

II-4

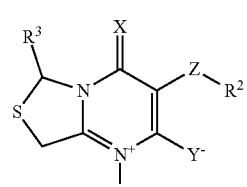

II-5

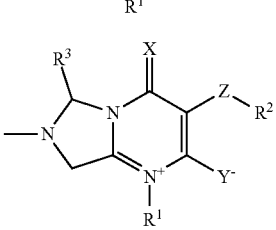

II-6

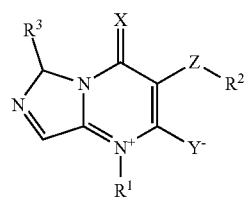

II-7

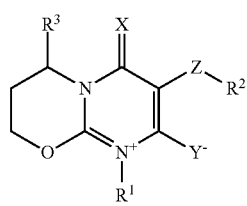

II-8

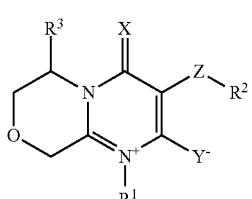

II-9

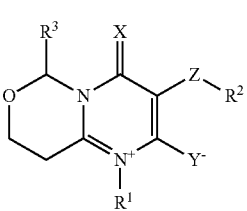

II-10

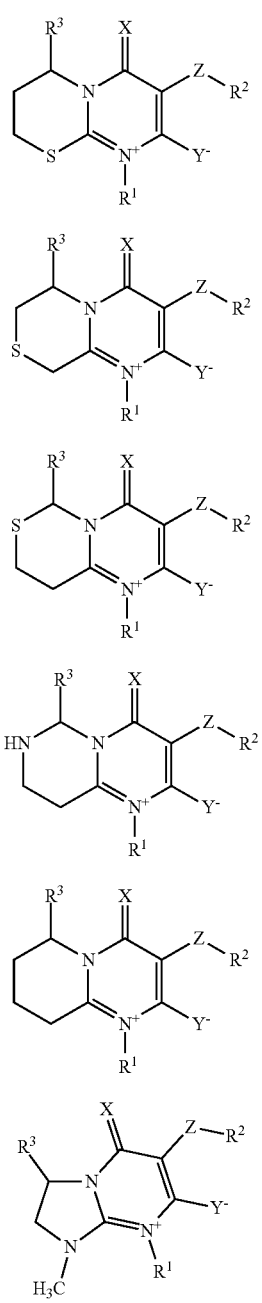

In a further embodiment, compounds of formula (I) are selected from the group of compounds of formulae II-1, II-2, II-3, II-4, II-5, II-6, II-8, II-9, II-10, II-11, II-12, II-13, II-14, II-15, and II-16.

In a further embodiment, compounds of formula (I) are selected from the group of compounds of formulae II-1, II-2, II-3, II-4, II-5, II-6, II-7 and II-15.

In a further embodiment, compounds of formula (I) are selected from the group of compounds of formulae II-1, II-2, II-3, II-4, II-5, II-6 and II-7.

In a further embodiment, compounds of formula (I) are selected from the group of compounds of formulae II-1, II-2, II-3, II-4, II-5, II-6 and II-16.

In a further embodiment, compounds of formula (I) are selected from the group of compounds of formulae II-1, II-4, II-5, and II-6.

In a further embodiment, compounds of formula (I) are selected from the group of compounds of formulae, II-8, II-9, II-10, II-11, II-12, II-13, II-14, and II-15.

In a further embodiment, compounds of formula (I) are selected from the group of compounds of formulae, II-11, II-12, II-13, II-14, and II-15.

In a further embodiment, compounds of formula (I) are selected from the group of compounds of formulae, II-1, II-4, II-5, II-6, II-11, II-12, II-13, II-14, and II-15.

In a preferred embodiment, the compound of formula (I) is a compound of formula II-1. In an other embodiment, the compound of formula (I) is a compound of formula II-4.

In an other embodiment, the compound of formula (I) is a compound of formula II-5.

In an other embodiment, the compound of formula (I) is a compound of formula II-6.

In an other embodiment, the compound of formula (I) is a compound of formula II-11.

In an other embodiment, the compound of formula (I) is a compound of formula II-12.

In an other embodiment, the compound of formula (I) is a compound of formula II-13.

In an other embodiment, the compound of formula (I) is a compound of formula II-14.

In an other embodiment, the compound of formula (I) is a compound of formula II-15.

In an other embodiment, the compound of formula (I) is a compound of formula II-16.

In an embodiment, $R^1$ is hydrogen, $C_1$-$C_8$-alkyl, $C_2$-$C_8$-alkenyl, $C_2$-$C_8$-alkynyl, $C_1$-$C_6$-alkoxy, $C_3$-$C_6$-cycloalkyl, $C_4$-$C_{10}$-cycloalkenyl or $C_5$-$C_{11}$-cycloalkylcycloalkyl, wherein the C-atoms of the aforementioned groups may be unsubstituted, or partially or fully substituted with $R^a$, wherein $R^a$ has the meaning as hereunder described.

In another embodiment, $R^1$ is a three- to ten-membered saturated, or partially saturated or heterocyclic ring system, which may contain 1 to 3 heteroatoms selected from $N(R^c)_p$, O, and S, wherein S may be oxidized and which heterocyclic ring may be unsubstituted or substituted with $R^a$.

In a further embodiment, $R^1$ is hydrogen, $C_1$-$C_4$-alkyl, $C_2$-$C_8$-alkenyl, $C_1$-$C_6$-alkoxy, $C_3$-$C_6$-cycloalkyl or $C_5$-$C_{11}$-cycloalkylcycloalkyl, wherein the C-atoms of the aforementioned groups may be unsubstituted, or partially or fully substituted with halogen.

In a further embodiment $R^1$ is $C_1$-$C_4$-alkyl, $C_2$-$C_8$-alkenyl, $C_3$-$C_6$-cycloalkyl, phenyl or benzyl, wherein the C-atoms of the aforementioned groups may be unsubstituted, or partially or fully substituted with $R^a$, wherein $R^a$ has the meaning as hereunder described.

In a further embodiment $R^1$ is $C_1$-$C_4$-alkyl, $C_3$-$C_6$-cycloalkyl or phenyl, wherein the C-atoms of the aforementioned groups may be unsubstituted, or partially or fully substituted with halogen or In a further embodiment $R^1$ is $C_1$-$C_4$-alkyl, $C_2$-$C_4$-alkenyl, phenyl or benzyl, wherein the c-atoms of the aforementioned groups may be partially or fully substituted with halogen, preferably Cl or F.

In a further embodiment $R^1$ is $C_1$-$C_4$-alkyl, $C_3$-$C_6$-cycloalkyl or phenyl, preferably $CH_3$, $CH_2CH_3$, $CH(CH_3)_2$, cyclopropyl or phenyl.

In another embodiment $R^1$ is $C_1$-$C_3$-alkyl, preferably $CH_3$, $CH_2CH_3$ or $CH(CH_3)_2$; particularly $R^1$ is $CH_2CH_3$.

In an embodiment, $R^2$ is hydrogen, halogen, CN, $NO_2$, $C_1$-$C_6$ alkyl, $C_1$-$C_6$-haloalkyl, $C_1$-$C_6$-haloalkoxy, $C_1$-$C_6$-alkoxy, $C_2$-$C_6$-alkenyl, $C_2$-$C_6$-alkynyl, $C_3$-$C_6$-cycloalkyl, $C_5$-$C_6$-cycloalkenyl, $C_5$-$C_{14}$-cycloalkylcycloalkyl or $S(O)_m$ $R^b$, wherein the C-atoms of the aforementioned groups may be unsubstituted, or partially or fully substituted with $R^{2a}$.

In an embodiment, $R^2$ is hydrogen, halogen, CN, $C_1$-$C_6$ alkyl, $C_1$-$C_2$-alkoxy-$C_1$-$C_2$-alkyl or $C_3$-$C_6$-cycloalkyl, wherein the C-atoms of the aforementioned groups may be substituted with halogen or CN.

In an embodiment, $R^2$ is hydrogen, halogen, CN or $C_1$-$C_4$-alkyl which may be substituted with halogen.

In a further embodiment $R^2$ is CN.

In a further embodiment, $R^2$ is hydrogen or $C_1$-$C_2$-alkyl, particularly $CH_3$.

In a further embodiment, $R^2$ is $C_1$-$C_6$-haloalkyl, preferably $C_1$-$C_2$-haloalkyl, particularly halomethyl, such as $CF_3$ or $CHF_2$.

In another embodiment, $R^2$ is $C_1$-$C_2$-alkoxy-$C_1$-$C_2$-alkyl, preferably $C_1$-$C_2$-alkoxy-methyl, particularly $CH_2OCH_3$.

In another embodiment, $R^2$ is $C_3$-$C_6$-cycloalkyl, preferably cyclopropyl which may be substituted, preferably by halogen or cyano.

In another embodiment, $R^2$ is $C_2$-$C_6$-alkyl, preferably $C_2$-$C_4$-alkyl, particularly $CH_2CH_3$ or $C(CH_3)_3$.

In another embodiment, $R^2$ is $C_1$-$C_6$-alkyl, preferably $C_1$-$C_2$-alkyl, particularly $CH_3$.

In another embodiment, $R^2$ is halogen, preferably Cl or F, particularly F.

In another embodiment, $R^2$ is a five- or six-membered carbo- or heterocyclic ring, which ring may be unsubstituted, partially, or fully substituted with $R^{2a}$, and wherein $R^{2a}$ is as hereunder defined or $R^{2a}$ is preferably halogen, $C_1$-$C_6$-haloalkyl, $C_1$-$C_6$-haloalkoxy, $OR^c$, $C(=O)OR^c$, $C(=O)NR^bR^c$, phenyl, or pyridyl which may be substituted with halogen, $C_1$-$C_6$-haloalkyl or $C_1$-$C_6$-haloalkoxy. In a further embodiment, $R^2$ is a six-membered carbo- or heterocyclic ring, which ring may be unsubstituted, partially, or fully substituted with $R^{2a}$, and wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl which may be substituted with $R^{2aa}$, wherein $R^{2aa}$ is as hereunder defined.

In a further embodiment, $R^2$ is a six-membered aromatic carbocyclic ring, which ring may be unsubstituted, partially, or fully substituted with $R^{2a}$, and wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl which may be substituted with $R^{2aa}$, wherein $R^{2aa}$ is as hereunder defined, preferably $R^{2aa}$ is halogen, $C_1$-$C_6$-haloalkyl or $C_1$-$C_6$-haloalkoxy.

Within this embodiment, $R^2$ is phenyl which may be substituted with halogen, $C_1$-$C_6$-haloalkyl or $C_1$-$C_6$-haloalkoxy.

Further, within this embodiment $R^2$ is phenyl which may be substituted with phenyl.

In a further embodiment, $R^2$ is a six-membered heterocyclic ring, which contains 1 or 2, preferably 1, heteroatom(s) selected from N—$R^c$, O, and S, wherein S may be oxidised, which heterocyclic ring is unsubstituted or substituted with one or more groups $R^{2a}$, wherein $R^{2a}$ is as hereunder defined.

In an embodiment, $R^a$ is halogen, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, CN, $OR^c$, $NR^bR^c$, $NO_2$, phenyl, pyridyl, thiazyl, furanyl, pyrimidinyl or thienyl, wherein the C-atoms aforementioned which groups may be unsubstituted or substituted with one or more $R^{aa}$, wherein $R^{aa}$ is as hereunder defined.

In a further embodiment, $R^a$ is halogen, $C_1$-$C_4$-alkyl, $C_1$-$C_4$-haloalkyl or $C_3$-$C_6$-cycloalkyl.

In a further embodiment, $R^a$ is halogen, $C_1$-$C_4$-alkyl, $C_1$-$C_4$-haloalkyl or $C_3$-$C_6$-cycloalkyl.

In a further embodiment, $R^a$ is halogen.

In an embodiment, $R^a$ is halogen, CN, $NO_2$, $S(O)_mR^b$, $C(O)R^c$, $C(O)OR^c$, $C(O)NR^bR^c$, $C(=S)NR^bR^c$, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, wherein the C-atoms of the aforementioned groups may be unsubstituted, partially or fully substituted with $R^{aa}$, wherein is as hereunder defined.

In a further embodiment, $R^a$ is halogen, CN, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, which C-atoms of the aforementioned groups may be unsubstituted, partially or fully substituted with $R^{aa}$, wherein $R^{aa}$ is as hereunder defined.

In a further embodiment, $R^a$ is halogen, CN, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, wherein the C-atoms of the aforementioned groups may be unsubstituted, partially or fully substituted with halogen.

In a further embodiment, $R^a$ is halogen, $C_1$-$C_6$-haloalkyl or $C_1$-$C_6$-alkoxy.

In a further embodiment, $R^a$ is halogen, CN or $C_1$-$C_2$-haloalkyl.

In a further embodiment, $R^a$ is halogen or $C_1$-$C_2$-haloalkyl.

In an embodiment, $R^a$ is halogen, preferably Br, Cl or F, particularly Cl.

In another embodiment, $R^a$ is $C_1$-$C_2$-haloalkyl, preferably halomethyl such as $CHF_2$ or $CF_3$, particularly $CF_3$.

In an embodiment, two geminally bound groups $R^a$ together may form a group selected from =O, =S, =$CR^bR^c$, =$NR^c$, =$NOR^c$, and =$NNR^cR^c$;

In another embodiment, two geminally bound groups $R^a$ together may form a group selected from =$CR^bR^c$, =$NR^c$, =$NOR^c$, and =$NNR^cR^c$;

In another embodiment, two geminally bound groups $R^a$ together may form a group selected from =O, =S and =$N(C_1$-$C_6$-alkyl).

In another embodiment, two geminally bound groups $R^a$ together may form a =$N(C_1$-$C_6$-alkyl) group.

In an embodiment, $R^b$ is hydrogen, $C_1$-$C_6$-alkyl, $C_1$-$C_6$-haloalkyl, $C_1$-$C_6$-alkoxy, $C_1$-$C_6$-haloalkoxy, phenyl, pyridyl, thiazyl or thienyl, wherein the C-atoms of the aforementioned groups may be substituted with $R^{aa}$, wherein $R^{aa}$ is as hereunder defined. In a further embodiment, $R^b$ is hydrogen, $C_1$-$C_6$-alkyl, $C_1$-$C_6$-haloalkyl, $C_1$-$C_6$-alkoxy or $C_1$-$C_6$-haloalkoxy. In a further embodiment, $R^b$ is hydrogen, $C_1$-$C_6$-alkyl or $C_1$-$C_6$-haloalkyl. In an embodiment, $R^b$ is $C_1$-$C_6$-alkyl or $C_1$-$C_6$-haloalkyl. In an embodiment, $R^b$ is H.

In an embodiment, $R^c$ is hydrogen, $C_1$-$C_4$-alkyl, $C_1$-$C_4$-haloalkyl, $C_1$-$C_4$-alkylcarbonyl, $C_1$-$C_6$ cycloalkyl, phenyl, pyridyl, thiazyl or thienyl wherein the C-atoms of the aforementioned groups may be substituted with $R^{aa}$, wherein $R^{aa}$ is as hereunder defined. In a further embodiment, $R^c$ is hydrogen, $C_1$-$C_4$-alkyl, $C_1$-$C_4$-haloalkyl, $C_1$-$C_4$-alkylcarbonyl, or $C_1$-$C_6$-cycloalkyl. In an embodiment, $R^c$ is hydrogen, $C_1$-$C_6$-alkyl or $C_1$-$C_6$-haloalkyl. In an embodiment, $R^c$ is $C_1$-$C_6$-alkyl or $C_1$-$C_6$-haloalkyl. In an embodiment, $R^c$ is H.

In an embodiment, two geminally bound groups $R^bR^b$, $R^cR^b$ or $R^cR^c$ together with the atom to which they are bound, may form a 3-, 4-, 5-, 6- or 7-membered saturated, partially unsaturated or aromatic carbo- or heterocyclic ring, which may contain 1 to 2 heteroatoms or heteroatoms groups selected from N, O, S, NO, SO and $SO_2$ and wherein the carbo- or heterocyclic ring may be partially or fully substituted with $R^4$.

In another embodiment, two geminally bound groups $R^bR^b$, $R^cR^b$ or $R^cR^c$ together with the atom to which they are bound, may form a 5- or 6-membered saturated, partially unsaturated or aromatic carbocyclic ring, which ring may be partially or fully substituted with $R^4$, and wherein $R^4$ is as hereunder defined.

In another embodiment, two geminally bound groups $R^bR^c$, $R^cR^b$ or $R^cR^c$ together with the atom to which they are bound, may form a 5- or 6-membered saturated, partially unsaturated or aromatic heterocyclic ring, which may contain 1 to 2 heteroatoms or heteroatoms groups selected from N, O, S, NO, SO and $SO_2$, wherein the heterocyclic ring may be partially or fully substituted with $R^4$, and wherein $R^4$ is as hereunder defined.

In an embodiment, $R^d$ is hydrogen, phenyl, $C_1$-$C_4$-alkyl or $C_2$-$C_6$-alkenyl, wherein the aforementioned groups may be substituted with one or more halogen. In a further embodiment, $R^d$ is $C_1$-$C_4$-alkyl or phenyl, which may be substituted with halogen. In another embodiment, $R^e$ $C_1$-$C_4$-alkyl, preferably $CH_3$.

In an embodiment, $R^e$ is $C_1$-$C_4$-alkyl, $C_1$-$C_4$-haloalkyl, $C_1$-$C_4$-alkylcarbonyl, $C_1$-$C_6$ cycloalkyl, phenyl, pyridyl, thiazyl or thienyl wherein the aforementioned groups may be substituted with $R^{aa}$, wherein $R^{aa}$ is as hereunder defined. In a further embodiment, $R^e$ is $C_1$-$C_4$-alkyl, $C_1$-$C_4$-haloalkyl, $C_1$-$C_4$-alkylcarbonyl, or $C_1$-$C_6$-cycloalkyl. In a further embodiment, $R^e$ is $C_1$-$C_4$-alkyl or $C_1$-$C_4$-haloalkyl.

In an embodiment, $R^{aa}$ is halogen, $C_1$-$C_6$-alkyl or $C_1$-$C_6$-haloalkyl. In another embodiment, $R^{aa}$ is $C_1$-$C_6$-alkoxy or $C_1$-$C_6$-haloalkoxy. In an embodiment, $R^{aa}$ is halogen.

In an embodiment, $R^{2a}$ is halogen, $C_1$-$C_6$-haloalkyl, $C_1$-$C_6$-alkoxy, $C_1$-$C_6$-haloalkoxy, $OR^c$, $C(=O)OR^c$, $C(=O)NR^bR^c$, or phenyl, wherein the C-atoms of the aforementioned groups may be unsubstituted or substituted with one or more $R^{2aa}$, wherein $R^{2aa}$ is as hereunder defined, particularly $R^{2a}$ is halogen, $C_1$-$C_6$-alkoxy, or $C_1$-$C_6$-haloalkoxy.

In an embodiment, two geminally bound groups $R^{2a}$ together may form a group selected from $=O$, $=S$ and $=N(C_1$-$C_6$-alkyl).

In an embodiment, $R^{2a}$ is halogen, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, CN, $OR^c$, $NR^bR^c$, $NO_2$, phenyl, pyridyl, thiazyl, furanyl, pyrimidinyl or thienyl, wherein the C-atoms of the aforementioned groups may be unsubstituted or substituted with one or more $R^{2aa}$, wherein $R^{2aa}$ is as hereunder defined.

In a further embodiment, $R^{2a}$ is halogen, $C_1$-$C_4$-haloalkyl or $C_3$-$C_6$-haloalkoxy.

In a another embodiment, $R^{2a}$ is phenyl which may be substituted with one or more $R^{2aa}$.

In a another embodiment, $R^{2a}$ is halogen. In another embodiment, $R^{2a}$ is $C_1$-$C_6$-haloalkyl. In another embodiment, $R^{2a}$ is $C_1$-$C_6$-haloalkoxy.

In another embodiment, $R^{2a}$ is halogen, CN, $NO_2$, $S(O)_m R^b$, $C(=O)R^c$, $C(=O)OR^c$, $C(O)NR^bR^c$, $C(=S)NR^bR^c$, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, which C-atoms of the aforementioned groups may be unsubstituted, partially or fully substituted with $R^{aa}$, wherein is as hereunder defined.

In further embodiment, $R^{2a}$ is, $C(=O)OR^c$ or $C(=O)NR^bR^c$.

In another embodiment, $R^{2a}$ is halogen, CN, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, which C-atoms of the aforementioned groups may be unsubstituted, partially or fully substituted with $R^{2aa}$, wherein $R^{2aa}$ is as hereunder defined.

In an embodiment, $R^{2a}$ is Br, Cl or F, particularly Cl.

In another embodiment, $R^{2a}$ is $C_1$-$C_2$-haloalkyl, preferably halomethyl such as $CHF_2$ or $CF_3$, particularly $CF_3$.

In an embodiment, $R^{2aa}$ is halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $N(C_1$-$C_6$-alkyl)(C(=O)(O)_p(C_1$-$C_6$-alkyl)$, $C(=O)N(C_1$-$C_6$-alkyl)(S(O)_m(C_1$-$C_6$-alkyl)$, $SO_2N(C_1$-$C_6$-alkyl)(C_1$-$C_6$-alkyl)$, $OSO_2(C_1$-$C_6$-alkyl)$, $N(C_1$-$C_6$-alkyl)SO_2(C_1$-$C_6$-alkyl)$, or $S(=O)_p(=N(C_1$-$C_6$-alkyl))(C_1$-$C_6$-alkyl)$ or two geminally bound groups $R^{2aa}$ together may form a group selected from $=O$, $=S$ and $=N(C_1$-$C_6$-alkyl)$.

In an embodiment, $R^{2aa}$ is halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $N(C_1$-$C_6$-alkyl)(C(=O)(O)_p(C_1$-$C_6$ alkyl)$, $C(=O)N(C_1$-$C_6$-alkyl)(S(O)_m(C_1$-$C_6$-alkyl)$, $SO_2N(C_1$-$C_6$-alkyl)(C_1$-$C_6$-alkyl)$, $OSO_2(C_1$-$C_6$-alkyl)$, $N(C_1$-$C_6$-alkyl)SO_2(C_1$-$C_6$-alkyl)$, or $S(=O)_p(=N(C_1$-$C_6$-alkyl))(C_1$-$C_6$-alkyl)$. In another embodiment, two geminally bound groups $R^{2aa}$ together may form a group selected from $=O$, $=S$ and $=N(C_1$-$C_6$-alkyl)$.

In an embodiment, $R^4$ is halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $N(C_1$-$C_6$-alkyl)(C(=O)(O)_p(C_1$-$C_6$ alkyl)$, $C(=O)N(C_1$-$C_6$-alkyl)(S(O)_m(C_1$-$C_6$-alkyl)$, $SO_2N(C_1$-$C_6$-alkyl)(C_1$-$C_6$-alkyl)$, $OSO_2(C_1$-$C_6$-alkyl)$, $N(C_1$-$C_6$-alkyl)SO_2(C_1$-$C_6$-alkyl)$, $S(=O)_p(=N(C_1$-$C_6$-alkyl))(C_1$-$C_6$-alkyl)$, or two geminally bound groups $R^4$ together may form a group selected from $=O$, $=S$ and $=N(C_1$-$C_6$-alkyl)$.

In an embodiment, $R^4$ is halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $N(C_1$-$C_6$-alkyl)(C(=O)(O)_p(C_1$-$C_6$ alkyl)$, $C(=O)N(C_1$-$C_6$-alkyl)(S(O)_m(C_1$-$C_6$-alkyl)$, $SO_2N(C_1$-$C_6$-alkyl)(C_1$-$C_6$-alkyl)$, $OSO_2(C_1$-$C_6$-alkyl)$, $N(C_1$-$C_6$-alkyl)SO_2(C_1$-$C_6$-alkyl)$, or $S(=O)_p(=N(C_1$-$C_6$-alkyl))(C_1$-$C_6$-alkyl)$. In another embodiment, two geminally bound groups $R^4$ together may form a group selected from $=O$, $=S$ and $=N(C_1$-$C_6$-alkyl)$.

In an embodiment, m is 0. In another embodiment, m is 1. In another embodiment, m is 2.

In an embodiment, n is 0. In another embodiment, n is 1. In another embodiment, n is 2.

In an embodiment, p is 0. In another embodiment, p is 1.

In one embodiment, $R^3$ is $C_1$-$C_4$-alkyl or $C_1$-$C_4$-haloalkyl, each substituted with at least one substituent selected from cyano and $NO_2$, preferably $C_1$-$C_4$-alkyl substituted with at least one substituent selected from cyano and $NO_2$, preferably $C_1$-$C_4$-alkyl substituted with one cyano.

In a further embodiment, $R^3$ is $CH_2$—CN or $CH_2$—$CH_2$—CN,

In a further embodiment, $R^3$ is $CH_2$—CN.

In a further embodiment of compounds of formula (I), wherein

X, Y are each O;

A is CH and the nitrogen of the pyrimidinium ring taken together with the contiguous linking carbon atom and A as depicted in formula (I), form a five or six membered ring, wherein each remaining ring member is selected from 2 and 3 carbon atoms;

$R^1$ is $CH_3$, $CH_2CH_3$, isopropyl, cyclopropyl, $CH_2CF_3$, phenyl, allyl or benzyl;

$R^2$ is phenyl which may be substituted with halogen, $C_1$-$C_6$-haloalkyl, $C_1$-$C_6$-haloalkoxy or phenyl;

Z is a direct bond and $R^3$ is cyanoethyl or cyanomethyl.

In particular, with a view to their use, preference is given to the compounds of the formula (I) compiled in the tables below, which compounds correspond to the compounds of formulae I.1.B (i.e. wherein X and Y are O) and to the preferred compounds of formula II-1, II-2, II-3, II-4, II-5, II-6, II-7, and II-15. Each of the groups mentioned for the substituents in the tables are furthermore per se, independently of the combination in which they are mentioned, a particularly preferred aspect of the substituent in question. Further, each individual meaning of a substituent in the tables constitutes a particularly preferred embodiment of the substituents in question.

TABLE 1

Compounds of the formula (III-1) corresponding to
the compounds of the formula II-1,
in which X and Y are O, $R^3$ is cyanoethyl and
the combination of $R^1$, $ZR^2$ for a compound
corresponds in each case to one line of Table A:

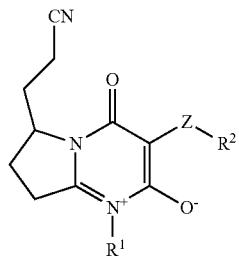

III-1

TABLE 2

Compounds of the formula (III-2) corresponding to
the compounds of the formula II-2,
in which X and Y are O, $R^3$ is cyanoethyl, and
the combination of $R^1$, $ZR^2$ for a compound
corresponds in each case to one line of Table A:

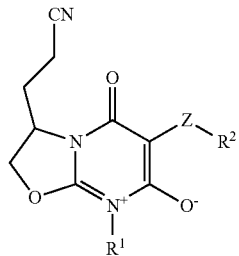

III-2

TABLE 3

Compounds of the formula (III-3) corresponding to
the compounds of the formula II-3,
in which X and Y are O, $R^3$ is cyanoethyl, and
the combination of $R^1$, $ZR^2$ for a compound
corresponds in each case to one line of Table A.

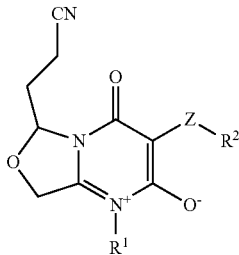

III-3

TABLE 4

Compounds of the formula (III-4) corresponding to
the compounds of the formula II-4,
in which X and Y are O, $R^3$ is cyanoethyl, and
the combination of $R^1$, $ZR^2$ for a compound
corresponds in each case to one line of Table A.

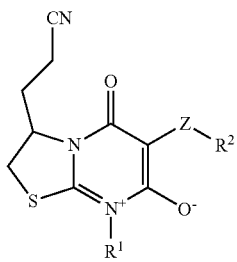

III-4

TABLE 5

Compounds of the formula (III-5) corresponding to
the compounds of the formula II-5,
in which X and Y are O, $R^3$ is cyanoethyl, and
the combination of $R^1$, $ZR^2$ for a compound
corresponds in each case to one line of Table A.

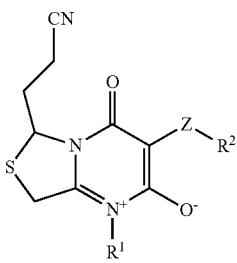

III-5

TABLE 6

Compounds of the formula (III-6) corresponding to
the compounds of the formula II-6,
in which X and Y are O, $R^3$ is cyanoethyl, and
the combination of $R^1$, $ZR^2$ for a compound
corresponds in each case to one line of Table A.

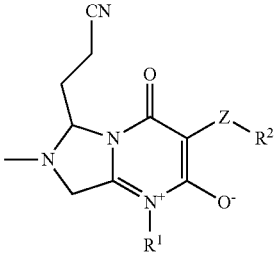

III-6

TABLE 7

Compounds of the formula (III-7) corresponding to the compounds of the formula II-7, in which X and Y are O, $R^3$ is cyanoethyl, and the combination of $R^1$, $ZR^2$ for a compound corresponds in each case to one line of Table A.

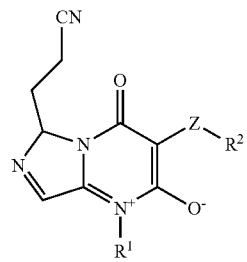

III-7

TABLE 8

Compounds of the formula (III-8) corresponding to the compounds of the formula II-15, in which X and Y are O, $R^3$ is cyanoethyl, and the combination of $R^1$, $ZR^2$ for a compound corresponds in each case to one line of Table A.

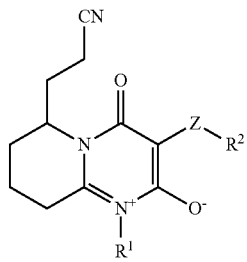

III-8

TABLE 9

Compounds of the formula (III-9) corresponding to the compounds of the formula II-1, in which X and Y are O, $R^3$ is cyanomethyl, and the combination of $R^1$, $ZR^2$ for a compound corresponds in each case to one line of Table A:

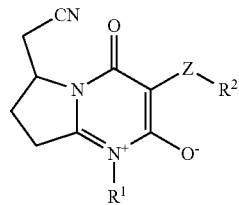

III-9

TABLE 10

Compounds of the formula (III-10) corresponding to the compounds of the formula II-2, in which X and Y are O, $R^3$ is cyanomethyl, and the combination of $R^1$, $ZR^2$ for a compound corresponds in each case to one line of Table A:

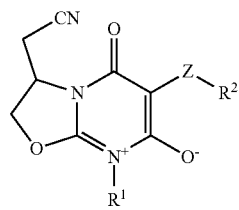

III-9

TABLE 11

Compounds of the formula (III-11) corresponding to the compounds of the formula II-3, in which X and Y are O, $R^3$ is cyanomethyl, and the combination of $R^1$, $ZR^2$ for a compound corresponds in each case to one line of Table A.

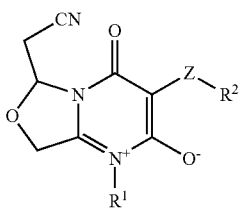

III-11

TABLE 12

Compounds of the formula (III-12) corresponding to the compounds of the formula II-4, in which X and Y are O, $R^3$ is cyanomethyl, and the combination of $R^1$, $ZR^2$ for a compound corresponds in each case to one line of Table A.

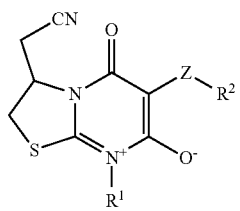

III-12

TABLE 13

Compounds of the formula (III-13) corresponding to the compounds of the formula II-5, in which X and Y are O, $R^3$ is cyanomethyl, and the combination of $R^1$, $ZR^2$ for a compound corresponds in each case to one line of Table A.

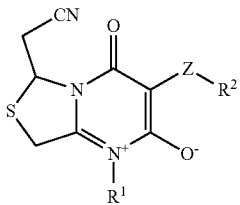

III-13

TABLE 14

Compounds of the formula (III-14) corresponding to the compounds of the formula II-6, in which X and Y are O, $R^3$ is cyanomethyl, and the combination of $R^1$, $ZR^2$ for a compound corresponds in each case to one line of Table A.

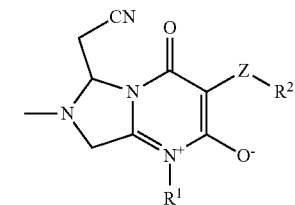

III-14

TABLE 15

Compounds of the formula (III-15) corresponding to the compounds of the formula II-7, in which X and Y are O, $R^3$ is cyanomethyl, and the combination of $R^1$, $ZR^2$ for a compound corresponds in each case to one line of Table A.

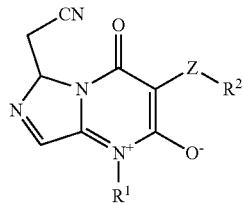

III-15

TABLE 16

Compounds of the formula (III-16) corresponding to the compounds of the formula II-15, in which X and Y are O, $R^3$ is cyanomethyl, and the combination of $R^1$, $ZR^2$ for a compound corresponds in each case to one line of Table A.

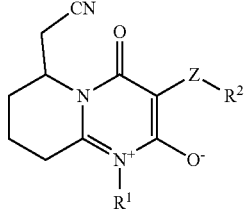

III-16

TABLE 17

Compounds of the formula (III-17) corresponding to the compounds of the formula II-1, in which X and Y are O, $R^3$ is phenyl, and the combination of $R^1$, $ZR^2$ for a compound corresponds in each case to one line of Table A:

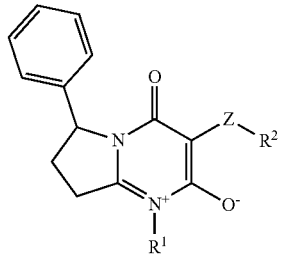

III-17

TABLE 18

Compounds of the formula (III-18) corresponding to the compounds of the formula II-2, in which X and Y are O, $R^3$ is phenyl, and the combination of $R^1$, $ZR^2$ for a compound corresponds in each case to one line of Table A:

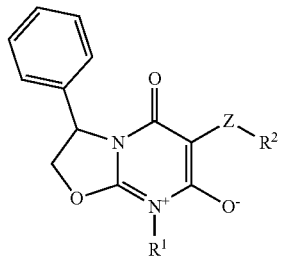

III-18

TABLE 19

Compounds of the formula (III-19) corresponding to the compounds of the formula II-3, in which X and Y are O, $R^3$ is phenyl, and the combination of $R^1$, $ZR^2$ for a compound corresponds in each case to one line of Table A.

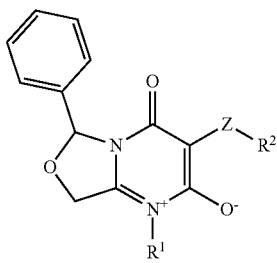

III-19

TABLE 20

Compounds of the formula (III-20) corresponding to the compounds of the formula II-4, in which X and Y are O, $R^3$ is phenyl, and the combination of $R^1$, $ZR^2$ for a compound corresponds in each case to one line of Table A.

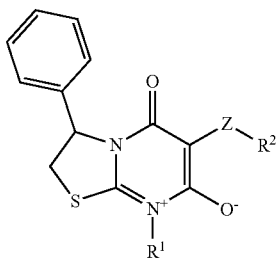

III-20

TABLE 21

Compounds of the formula (III-21) corresponding to the compounds of the formula II-5, in which X and Y are O, $R^3$ is phenyl, and the combination of $R^1$, $ZR^2$ for a compound corresponds in each case to one line of Table A.

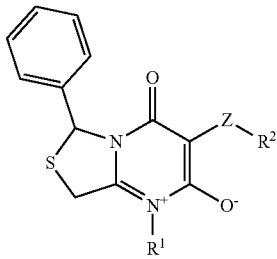

III-21

TABLE 22

Compounds of the formula (III-22) corresponding to the compounds of the formula II-6, in which X and Y are O, $R^3$ is phenyl, and the combination of $R^1$, $ZR^2$ for a compound corresponds in each case to one line of Table A.

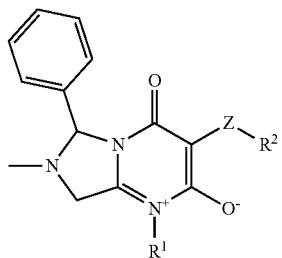

III-22

TABLE 23

Compounds of the formula (III-23) corresponding to the compounds of the formula II-7, in which X and Y are O, $R^3$ is phenyl, and the combination of $R^1$, $ZR^2$ for a compound corresponds in each case to one line of Table A.

III-23

TABLE 24

Compounds of the formula (III-24) corresponding to the compounds of the formula II-15, in which X and Y are O, $R^3$ is phenyl, and the combination of $R^1$, $ZR^2$ for a compound corresponds in each case to one line of Table A.

III-24

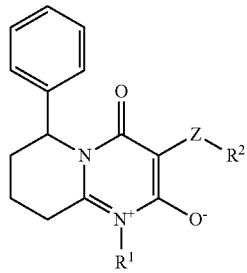

TABLE 25

Compounds of the formula (III-25) corresponding to the compounds of the formula II-1, in which X and Y are O, $R^3$ is phenylmethyl and the combination of $R^1$, $ZR^2$ for a compound corresponds in each case to one line of Table A:

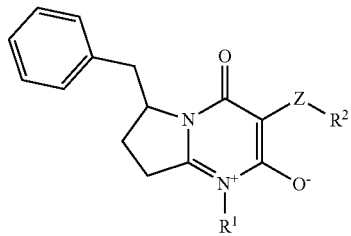

III-25

TABLE 26

Compounds of the formula (III-26) corresponding to the compounds of the formula II-2, in which X and Y are O, $R^3$ is phenylmethyl, and the combination of $R^1$, $ZR^2$ for a compound corresponds in each case to one line of Table A:

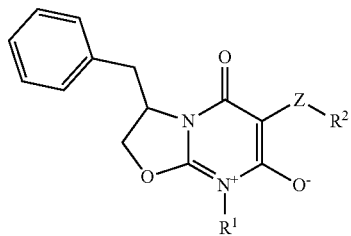

III-26

TABLE 27

Compounds of the formula (III-27) corresponding to the compounds of the formula II-3, in which X and Y are O, $R^3$ is phenylmethyl, and the combination of $R^1$, $ZR^2$ for a compound corresponds in each case to one line of Table A.

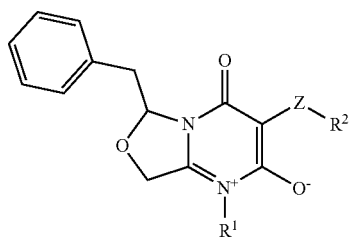

III-27

TABLE 28

Compounds of the formula (III-28) corresponding to the compounds of the formula II-4, in which X and Y are O, R³ is phenylmethyl, and the combination of R¹, ZR² for a compound corresponds in each case to one line of Table A.

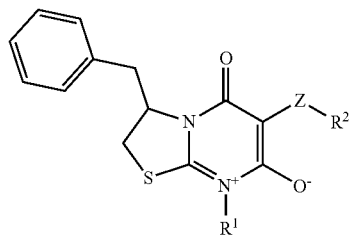

III-28

TABLE 29

Compounds of the formula (III-29) corresponding to the compounds of the formula II-5, in which X and Y are O, R³ is phenylmethyl, and the combination of R¹, ZR² for a compound corresponds in each case to one line of Table A.

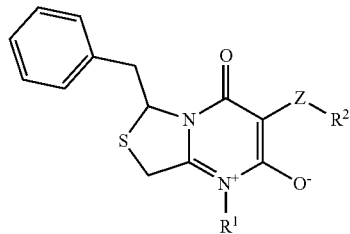

III-29

TABLE 30

Compounds of the formula (III-30) corresponding to the compounds of the formula II-6, in which X and Y are O, R³ is phenylmethyl, and the combination of R¹, ZR² for a compound corresponds in each case to one line of Table A.

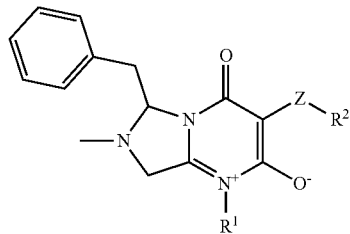

III-30

TABLE 31

Compounds of the formula (III-31) corresponding to the compounds of the formula II-7, in which X and Y are O, R³ is phenylmethyl, and the combination of R¹, ZR² for a compound corresponds in each case to one line of Table A.

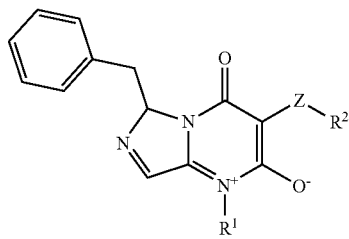

III-31

TABLE 32

Compounds of the formula (III-32) corresponding to the compounds of the formula II-15, in which X and Y are O, R³ is phenylmethyl, and the combination of R¹, ZR² for a compound corresponds in each case to one line of Table A.

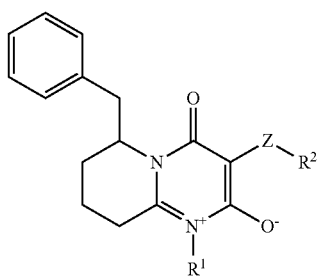

III-32

TABLE 33

Compounds of the formula (III-33) corresponding to the compounds of the formula II-17, in which X and Y are O, R³ is cyanoethyl, and the combination of R¹, ZR² for a compound corresponds in each caseto one line of Table A.

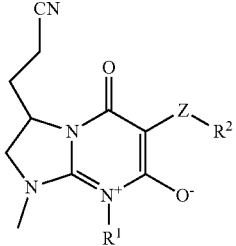

III-33

TABLE 34

Compounds of the formula (III-34) corresponding to the compounds of the formula II-17, in which X and Y are O, $R^3$ is cyanomethyl, and the combination of $R^1$, $ZR^2$ for a compound corresponds in each case to one line of Table A.

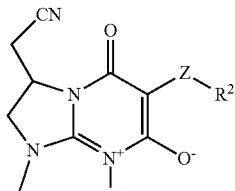

III-34

TABLE 35

Compounds of the formula (III-35) corresponding to the compounds of the formula II-17, in which X and Y are O, $R^3$ is phenyl, and the combination of $R^1$, $ZR^2$ for a compound corresponds in each case to one line of Table A.

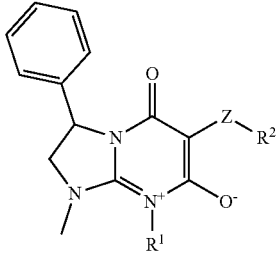

III-35

TABLE 36

Compounds of the formula (III-36) corresponding to the compounds of the formula II-17, in which X and Y are O, $R^3$ is phenylmethyl, and the combination of $R^1$, $ZR^2$ for a compound corresponds in each case to one line of Table A.

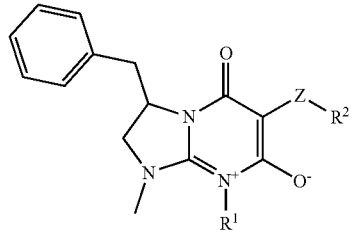

III-36

TABLE A

| No. | $ZR^2$ | $R^1$ |
|---|---|---|
| A-1 | $C_6H_5$ | $CH_3$ |
| A-2 | 2-fluorophenyl | $CH_3$ |
| A-3 | 2-methoxyphenyl | $CH_3$ |
| A-4 | 2,4-difluorophenyl | $CH_3$ |
| A-5 | 2,6-difluorophenyl | $CH_3$ |
| A-6 | 4-fluorophenyl | $CH_3$ |
| A-7 | $CO_2CH_2CH_3$ | $CH_3$ |
| A-8 | $C(O)CF_3$ | $CH_3$ |
| A-9 | $C(O)C_6H_5$ | $CH_3$ |
| A-10 | 3-methoxyphenyl | $CH_3$ |
| A-11 | 3-cyanophenyl | $CH_3$ |
| A-12 | 3-($CO_2CH_2CH_3$)phenyl | $CH_3$ |
| A-13 | 3-(C(O)N($CH_3$)$_2$)phenyl | $CH_3$ |
| A-14 | 3-(trifluoromethyl)phenyl | $CH_3$ |
| A-15 | 3-(trifluoromethoxy)phenyl | $CH_3$ |
| A-16 | 3,5-dichlorophenyl | $CH_3$ |
| A-17 | 3-fluoro-5-methylphenyl | $CH_3$ |
| A-18 | 2-methoxy-5-(trifluoromethyl)phenyl | $CH_3$ |
| A-19 | 3-chloro-5(trifluoromethyl)phenyl | $CH_3$ |
| A-20 | 3-(2-chloro-4-(trifluoromethyl)phenyl)phenyl | $CH_3$ |
| A-21 | 3-(2-chloro-4-(trifluoromethyl)phenyl)-4-fluorophenyl | $CH_3$ |
| A-22 | 3-(2-chloro-4-(trifluoromethyl)phenyl)-5-methylphenyl | $CH_3$ |
| A-23 | 3-phenylphenyl | $CH_3$ |
| A-24 | 4-methoxyphenyl | $CH_3$ |
| A-25 | 3-(3-chloro-5-trifluoromethyl-pyridine-2-yl)phenyl | $CH_3$ |
| A-26 | $C_6H_5$ | $CH_2CH_3$ |
| A-27 | 2-fluorophenyl | $CH_2CH_3$ |
| A-28 | 2-methoxyphenyl | $CH_2CH_3$ |
| A-29 | 2,4-difluorophenyl | $CH_2CH_3$ |
| A-30 | 2,6-difluorophenyl | $CH_2CH_3$ |
| A-31 | 4-fluorophenyl | $CH_2CH_3$ |
| A-32 | $CO_2CH_2CH_3$ | $CH_2CH_3$ |
| A-33 | $C(O)CF_3$ | $CH_2CH_3$ |
| A-34 | $C(O)C_6H_5$ | $CH_2CH_3$ |
| A-35 | 3-methoxyphenyl | $CH_2CH_3$ |
| A-36 | 3-cyanophenyl | $CH_2CH_3$ |
| A-37 | 3-($CO_2CH_2CH_3$)phenyl | $CH_2CH_3$ |
| A-38 | 3-(C(O)N($CH_3$)$_2$)phenyl | $CH_2CH_3$ |
| A-39 | 3-(trifluoromethyl)phenyl | $CH_2CH_3$ |
| A-40 | 3-(trifluoromethoxy)phenyl | $CH_2CH_3$ |
| A-41 | 3,5-dichlorophenyl | $CH_2CH_3$ |
| A-42 | 3-fluoro-5-methylphenyl | $CH_2CH_3$ |
| A-43 | 2-methoxy-5-(trifluoromethyl)phenyl | $CH_2CH_3$ |
| A-44 | 3-chloro-5(trifluoromethyl)phenyl | $CH_2CH_3$ |
| A-45 | 3-(2-chloro-4-(trifluoromethyl)phenyl)phenyl | $CH_2CH_3$ |
| A-46 | 3-(2-chloro-4-(trifluoromethyl)phenyl)-4-fluorophenyl | $CH_2CH_3$ |
| A-47 | 3-(2-chloro-4-(trifluoromethyl)phenyl)-5-methylphenyl | $CH_2CH_3$ |
| A-48 | 3-phenylphenyl | $CH_2CH_3$ |
| A-49 | 4-methoxyphenyl | $CH_2CH_3$ |
| A-50 | 3-(3-chloro-5-trifluoromethyl-pyridine-2-yl)phenyl | $CH_2CH_3$ |
| A-51 | $C_6H_5$ | $CH(CH_3)_2$ |
| A-52 | 2-fluorophenyl | $CH(CH_3)_2$ |
| A-53 | 2-methoxyphenyl | $CH(CH_3)_2$ |
| A-54 | 2,4-difluorophenyl | $CH(CH_3)_2$ |
| A-55 | 2,6-difluorophenyl | $CH(CH_3)_2$ |
| A-56 | 4-fluorophenyl | $CH(CH_3)_2$ |
| A-57 | $CO_2CH_2CH_3$ | $CH(CH_3)_2$ |
| A-58 | $C(O)CF_3$ | $CH(CH_3)_2$ |
| A-59 | $C(O)C_6H_5$ | $CH(CH_3)_2$ |
| A-60 | 3-methoxyphenyl | $CH(CH_3)_2$ |
| A-61 | 3-cyanophenyl | $CH(CH_3)_2$ |
| A-62 | 3-($CO_2CH_2CH_3$)phenyl | $CH(CH_3)_2$ |
| A-63 | 3-(C(O)N($CH_3$)$_2$)phenyl | $CH(CH_3)_2$ |
| A-64 | 3-(trifluoromethyl)phenyl | $CH(CH_3)_2$ |
| A-65 | 3-(trifluoromethoxy)phenyl | $CH(CH_3)_2$ |
| A-66 | 3,5-dichlorophenyl | $CH(CH_3)_2$ |
| A-67 | 3-fluoro-5-methylphenyl | $CH(CH_3)_2$ |
| A-68 | 2-methoxy-5-(trifluoromethyl)phenyl | $CH(CH_3)_2$ |
| A-69 | 3-chloro-5(trifluoromethyl)phenyl | $CH(CH_3)_2$ |
| A-70 | 3-(2-chloro-4-(trifluoromethyl)phenyl)phenyl | $CH(CH_3)_2$ |
| A-71 | 3-(2-chloro-4-(trifluoromethyl)phenyl)-4-fluorophenyl | $CH(CH_3)_2$ |
| A-72 | 3-(2-chloro-4-(trifluoromethyl)phenyl)-5-methylphenyl | $CH(CH_3)_2$ |
| A-73 | 3-phenylphenyl | $CH(CH_3)_2$ |
| A-74 | 4-methoxyphenyl | $CH(CH_3)_2$ |
| A-75 | 3-(3-chloro-5-trifluoromethyl-pyridine-2-yl)phenyl | $CH(CH_3)_2$ |
| A-76 | $C_6H_5$ | $CH_2CH{=}CH_2$ |
| A-77 | 2-fluorophenyl | $CH_2CH{=}CH_2$ |
| A-78 | 2-methoxyphenyl | $CH_2CH{=}CH_2$ |
| A-79 | 2,4-difluorophenyl | $CH_2CH{=}CH_2$ |
| A-80 | 2,6-difluorophenyl | $CH_2CH{=}CH_2$ |

TABLE A-continued

| No. | ZR² | R¹ |
|---|---|---|
| A-81 | 4-fluorophenyl | CH₂CH=CH₂ |
| A-82 | CO₂CH₂CH₃ | CH₂CH=CH₂ |
| A-83 | C(O)CF₃ | CH₂CH=CH₂ |
| A-84 | C(O)C₆H₅ | CH₂CH=CH₂ |
| A-85 | 3-methoxyphenyl | CH₂CH=CH₂ |
| A-86 | 3-cyanophenyl | CH₂CH=CH₂ |
| A-87 | 3-(CO₂CH₂CH₃)phenyl | CH₂CH=CH₂ |
| A-88 | 3-(C(O)N(CH₃)₂)phenyl | CH₂CH=CH₂ |
| A-89 | 3-(trifluoromethyl)phenyl | CH₂CH=CH₂ |
| A-90 | 3-(trifluoromethoxy)phenyl | CH₂CH=CH₂ |
| A-91 | 3,5-dichlorophenyl | CH₂CH=CH₂ |
| A-92 | 3-fluoro-5-methylphenyl | CH₂CH=CH₂ |
| A-93 | 2-methoxy-5(trifluoromethyl)phenyl | CH₂CH=CH₂ |
| A-94 | 3-chloro-5(trifluoromethyl)phenyl | CH₂CH=CH₂ |
| A-95 | 3-(2-chloro-4-(trifluoromethyl)phenyl)phenyl | CH₂CH=CH₂ |
| A-96 | 3-(2-chloro-4-(trifluoromethyl)phenyl)-4-fluorophenyl | CH₂CH=CH₂ |
| A-97 | 3-(2-chloro-4-(trifluoromethyl)phenyl)-5-methylphenyl | CH₂CH=CH₂ |
| A-98 | 3-phenylphenyl | CH₂CH=CH₂ |
| A-99 | 4-methoxyphenyl | CH₂CH=CH₂ |
| A-100 | 3-(3-chloro-5-trifluoromethyl-pyridine-2-yl)phenyl | CH₂CH=CH₂ |
| A-101 | C₆H₅ | CH₂C₆H₅ |
| A-102 | 2-fluorophenyl | CH₂C₆H₅ |
| A-103 | 2-methoxyphenyl | CH₂C₆H₅ |
| A-104 | 2,4-difluorophenyl | CH₂C₆H₅ |
| A-105 | 2,6-difluorophenyl | CH₂C₆H₅ |
| A-106 | 4-fluorophenyl | CH₂C₆H₅ |
| A-107 | CO₂CH₂CH₃ | CH₂C₆H₅ |
| A-108 | C(O)CF₃ | CH₂C₆H₅ |
| A-109 | C(O)C₆H₅ | CH₂C₆H₅ |
| A-110 | 3-methoxyphenyl | CH₂C₆H₅ |
| A-111 | 3-cyanophenyl | CH₂C₆H₅ |
| A-112 | 3-(CO₂CH₂CH₃)phenyl | CH₂C₆H₅ |
| A-113 | 3-(C(O)N(CH₃)₂)phenyl | CH₂C₆H₅ |
| A-114 | 3-(trifluoromethyl)phenyl | CH₂C₆H₅ |
| A-115 | 3-(trifluoromethoxy)phenyl | CH₂C₆H₅ |
| A-116 | 3,5-dichlorophenyl | CH₂C₆H₅ |
| A-117 | 3-fluoro-5-methylphenyl | CH₂C₆H₅ |
| A-118 | 2-methoxy-5(trifluoromethyl)phenyl | CH₂C₆H₅ |
| A-119 | 3-chloro-5(trifluoromethyl)phenyl | CH₂C₆H₅ |
| A-120 | 3-(2-chloro-4-(trifluoromethyl)phenyl)phenyl | CH₂C₆H₅ |
| A-121 | 3-(2-chloro-4-(trifluoromethyl)phenyl)-4-fluorophenyl | CH₂C₆H₅ |
| A-122 | 3-(2-chloro-4-(trifluoromethyl)phenyl)-5-methylphenyl | CH₂C₆H₅ |
| A-123 | 3-phenylphenyl | CH₂C₆H₅ |
| A-124 | 4-methoxyphenyl | CH₂C₆H₅ |
| A-125 | 3-(3-chloro-5-trifluoromethyl-pyridine-2-yl)phenyl | CH₂C₆H₅ |
| A-126 | C₆H₅ | CH₂CF₃ |
| A-127 | 2-fluorophenyl | CH₂CF₃ |
| A-128 | 2-methoxyphenyl | CH₂CF₃ |
| A-129 | 2,4-difluorophenyl | CH₂CF₃ |
| A-130 | 2,6-difluorophenyl | CH₂CF₃ |
| A-131 | 4-fluorophenyl | CH₂CF₃ |
| A-132 | CO₂CH₂CH₃ | CH₂CF₃ |
| A-133 | C(O)CF₃ | CH₂CF₃ |
| A-134 | C(O)C₆H₅ | CH₂CF₃ |
| A-135 | 3-methoxyphenyl | CH₂CF₃ |
| A-136 | 3-cyanophenyl | CH₂CF₃ |
| A-137 | 3-(CO₂CH₂CH₃)phenyl | CH₂CF₃ |
| A-138 | 3-(C(O)N(CH₃)₂)phenyl | CH₂CF₃ |
| A-139 | 3-(trifluoromethyl)phenyl | CH₂CF₃ |
| A-140 | 3-(trifluoromethoxy)phenyl | CH₂CF₃ |
| A-141 | 3,5-dichlorophenyl | CH₂CF₃ |
| A-142 | 3-fluoro-5-methylphenyl | CH₂CF₃ |
| A-143 | 2-methoxy-5(trifluoromethyl)phenyl | CH₂CF₃ |
| A-144 | 3-chloro-5(trifluoromethyl)phenyl | CH₂CF₃ |
| A-145 | 3-(2-chloro-4-(trifluoromethyl)phenyl)phenyl | CH₂CF₃ |
| A-146 | 3-(2-chloro-4-(trifluoromethyl)phenyl)-4-fluorophenyl | CH₂CF₃ |
| A-147 | 3-(2-chloro-4-(trifluoromethyl)phenyl)-5-methylphenyl | CH₂CF₃ |
| A-148 | 3-phenylphenyl | CH₂CF₃ |
| A-149 | 4-methoxyphenyl | CH₂CF₃ |
| A-150 | 3-(3-chloro-5-trifluoromethyl-pyridine-2-yl)phenyl | CH₂CF₃ |

The compound of formula (I) according to the present invention can be prepared according to the following syntheses routes, e.g. according to the preparation methods and preparation schemes as described below.

The compound of formula (I) according to the present invention can be prepared according to the e.g. preparation methods and preparation schemes as described below.

The compounds used as starting materials for the syntheses of the compounds according to the present invention can generally be prepared by standard methods of organic chemistry. If not otherwise specified, the definitions of the variables such as X, Y, R³, R¹ and R² of the structures given in the schemes have the same meaning as defined above.

Compounds of the formula (I) can for example be prepared by reacting the appropriately substituted compounds P-1 with the a malonate derivative P-2 analogous to the methods described by Holyoke et al. in WO 2009/099929 (Scheme 1):

Scheme 1

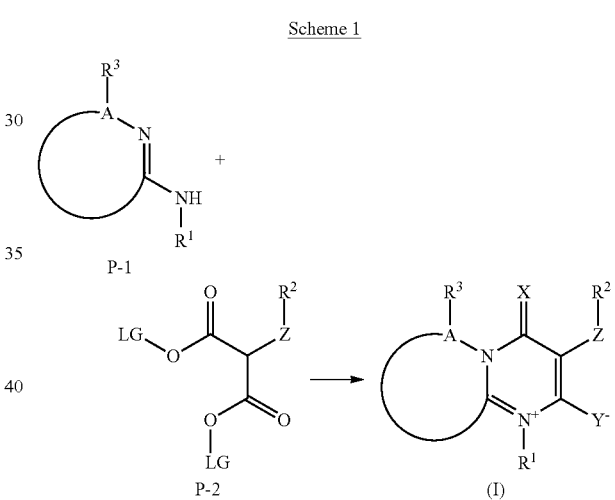

Compounds like P-1 can be prepared from the corresponding compounds P-3, by reacting it with an amine nucleophile like P-4 as described by, for example, Michel Langlois et al, Journal of Heterocyclic Chemistry, 19(1), 193-200; 1982, wherein LG denotes a leaving group such as halogen (e.g. chlorine or bromine), OR', or SR', with R' being C₁-C₆-alkyl, preferably chlorine methoxy ethoxy, methylthio or ethylthio (Scheme 2):

Scheme 2

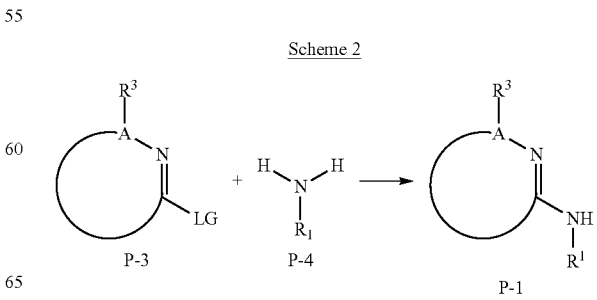

Compounds like P-3 are available from the corresponding lactams P-5 by standard procedures known to a person skilled in the art. For example see Allen, Jennifer Rebecca et al in WO 2004/094382 or Lang, Kai et al, Journal of Organic Chemistry, 75(19), 6424-6435; 2010 (Scheme 3):

Scheme 3

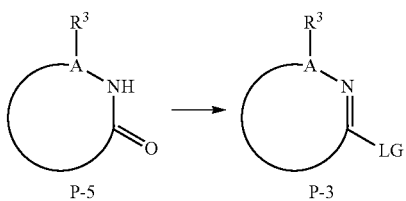

Lactams are widespread in organic chemistry and methods to produce them are well known. For example see: Smith, M. B. in Science of Synthesis, (2005) 21, 653.

If individual compounds cannot be prepared via the above described routes, they can be prepared by derivatization of other compounds of formula (I) or by customary modifications of the synthesis routes described.

For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or silica gel.

As used herein, the term "compound(s) of the present invention" or "compound(s) according to the invention" refers to the compound(s) of formula (I) as defined above, which are also referred to as "compound(s) of formula I" or "compound(s) I" or "formula I compound(s)", and includes their salts, tautomers, stereoisomers, and N-oxides.

Mixtures

The present invention also relates to a mixture of at least one compound of the present invention with at least one mixing partner as defined herein after. Preferred are binary mixtures of one compound of the present invention as component I with one mixing partner as defined herein after as component II. Preferred weight ratios for such binary mixtures are from 5000:1 to 1:5000, preferably from 1000:1 to 1:1000, more preferably from 100:1 to 1:100, particularly preferably from 10:1 to 1:10. In such binary mixtures, components I and II may be used in equal amounts, or an excess of component I, or an excess of component II may be used.

Mixing partners can be selected from pesticides, in particular insecticides, nematicides, and acaricides, fungicides, herbicides, plant growth regulators, fertilizers, and the like. Preferred mixing partners are insecticides, nematicides and fungicides.

The following list M of pesticides, grouped and numbered according the Mode of Action Classification of the Insecticide Resistance Action Committee (IRAC), together with which the compounds of the present invention can be used and with which potential synergistic effects might be produced, is intended to illustrate the possible combinations, but not to impose any limitation:

M.1 Acetylcholine esterase (AChE) inhibitors from the class of: M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as: M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of M.4A neonicotinoids, for example acetamiprid, clothianidin, cycloxaprid, dinotefuran, imidacloprid, nitenpyram, thiacloprid and thiamethoxam; or the compounds M.4A.2: (2E-)-1-[(6-Chloropyridin-3-yl)methyl]-N'-nitro-2-pentylidenehydrazinecarboximidamide; or M4.A.3: 1-[(6-Chloropyridin-3-yl)methyl]-7-methyl-8-nitro-5-propoxy-1,2,3,5,6,7-hexahydroimidazo[1,2-a]pyridine; or from the class M.4B nicotine;

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as M.7A juvenile hormone analogues as hydroprene, kinoprene and methoprene; or others as M.78 fenoxycarb or M.7C pyriproxyfen;

M.8 miscellaneous non-specific (multi-site) inhibitors, for example M.8A alkyl halides as methyl bromide and other alkyl halides, or M.88 chloropicrin, or M.8C sulfuryl fluoride, or M.8D borax, or M.8E tartar emetic;

M.9 Selective homopteran feeding blockers, for example M.98 pymetrozine, or M.9C flonicamid;

M.10 Mite growth inhibitors, for example M.10A clofentezine, hexythiazox and diflovidazin, or M.10B etoxazole;

M.11 Microbial disruptors of insect midgut membranes, for example *Bacillus thuringiensis* or *Bacillus sphaericus* and the insecticdal proteins they produce such as *Bacillus thuringiensis* subsp. *israelensis, Bacillus sphaericus, Bacillus thuringiensis* subsp. *aizawai, Bacillus thuringiensis* subsp. *kurstaki* and *Bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example M.12A diafenthiuron, or M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example M.20A hydramethylnon, or M.206 acequinocyl, or M.20C fluacrypyrim;

M.21 Mitochondrial complex I electron transport inhibitors, for example M.21A METI acaricides and insecticides such as fenazaquin, fenpyroximate, pyrimidifen, pyridaben, tebufenpyrad or tolfenpyrad, or M.216 rotenone;

M.22 Voltage-dependent sodium channel blockers, for example M.22A indoxacarb, or M.22B metaflumizone, or M.22B.1: 2-[2-(4-Cyanophenyl)-1-[3-(trifluoromethyl)phenyl]ethylidene]-N-[4-(difluoromethoxy)phenyl]-hydrazinecarboxamide or M.22B.2: N-(3-Chloro-2-methylphenyl)-2-[(4-chlorophenyl)[4-[methyl(methylsulfonyl)amino]phenyl]methylene]-hydrazinecarboxamide;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example M.24A phosphine such as aluminium phosphide, calcium phosphide, phosphine or zinc phosphide, or M.246 cyanide;

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), tetraniliprole, or the phthalamide compounds M.28.1: (R)-3-Chlor-N1-{2-methyl-4-[1,2,2,2 tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2 tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarbovlate; or a compound selected from M.28.5a) to M.28.5d) and M.28.5h) to M.28.5I): M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide; M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide; M.28.5j) 3-Chloro-1-(3-chloro-2-pyridinyl)-N-[2,4-dichloro-6-[[(1-cyano-1-methylethyl)amino]carbonyl]phenyl]-1H-pyrazole-5-carboxamide; M.28.5k) 3-Bromo-N-[2,4-dichloro-6-(methylcarbamoyl)phenyl]-1-(3,5-dichloro-2-pyridyl)-1H-pyrazole-5-carboxamide; M.28.5l) N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide; or M.28.6: cyhalodiamide; or;

M.29. insecticidal active compounds of unknown or uncertain mode of action, as for example afidopyropen, afoxolaner, azadirachtin, amidoflumet, benzoximate, bifenazate, broflanilide, bromopropylate, chinomethionat, cryolite, dicloromezotiaz, dicofol, flufenerim, flometoquin, fluensulfone, fluhexafon, fluopyram, flupyradifurone, fluralaner, metoxadiazone, piperonyl butoxide, pyflubumide, pyridalyl, pyrifluquinazon, sulfoxaflor, tioxazafen, triflumezopyrim, or the compounds M.29.3: 11-(4-chloro-2,6-dimethylphenyl)-12-hydroxy-1,4-dioxa-9-azadispiro[4.2.4.2]-tetradec-11-en-10-one, or the compound M.29.4: 3-(4'-fluoro-2,4-dimethylbiphenyl-3-yl)-4-hydroxy-8-oxa-1-azaspiro[4.5]dec-3-en-2-one, or the compound M.29.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *Bacillus firmus* (Votivo, 1-1582); or a compound selected from the group of M.29.6, wherein the compound is selected from M.29.6a) to M.29.6k): M.29.6a) (E/Z)-N-[1-[(6-chloro-3-pyridyl)methyl]-2-pyridylidene]-2,2,2-trifluoro-acetamide; M.29.6b) (E/Z)-N-[1-[(6-chloro-5-fluoro-3-pyridyl)methyl]-2-pyridylidene]-2,2,2-trifluoro-acetamide; M.29.6c) (E/Z)-2,2,2-trifluoro-N-[1-[(6-fluoro-3-pyridyl)methyl]-2-pyridylidene]acetamide; M.29.6d) (E/Z)-N-[1-[(6-bromo-3-pyridyl)methyl]-2-pyridylidene]-2,2,2-trifluoro-acetamide; M.29.6e) (E/Z)-N-[1-[1-(6-chloro-3-pyridyl)ethyl]-2-pyridylidene]-2,2,2-trifluoro-acetamide; M.29.6f) (E/Z)-N-[1-[(6-chloro-3-pyridyl)methyl]-2-pyridylidene]-2,2-difluoro-acetamide; M.29.6g)

(E/Z)-2-chloro-N-[1-[(6-chloro-3-pyridyl)methyl]-2-pyridylidene]-2,2-difluoro-acetamide; M.29.6h) (E/Z)-N-[1-[(2-chloropyrimidin-5-yl)methyl]-2-pyridylidene]-2,2,2-trifluoro-acetamide; M.29.6i) (E/Z)-N-[1-[(6-chloro-3-pyridyl)methyl]-2-pyridylidene]-2,2,3,3,3-pentafluoropropanamide); M.29.6j) N-[1-[(6-chloro-3-pyridyl)methyl]-2-pyridylidene]-2,2,2-trifluoro-thioacetamide; or M.29.6k) N-[1-[(6-chloro-3-pyridyl)methyl]-2-pyridylidene]-2,2,2-trifluoro-N'-isopropyl-acetamidine; or the compounds M.29.8: fluazaindolizine; or the compounds M.29.9.a): 4-[5-(3,5-dichlorophenyl)-5-(trifluoromethyl)-4H-isoxazol-3-yl]-2-methyl-N-(1-oxothietan-3-yl)benzamide; or M.29.9.b): fluxametamide; or M.29.10: 5-[3-[2,6-dichloro-4-(3,3-dichloroallyloxy)phenoxy]propoxy]-1H-pyrazole; or a compound selected from the group of M.29.11, wherein the compound is selected from M.29.11b) to M.29.11p): M.29.11.b) 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide; M.29.11.c) 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide; M.29.11.d) N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.e) N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide; M.29.11.f) 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.g) 3-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.h) 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide; M.29.11.i) 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide; M.29.11j) 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide; M.29.11.k) N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide; M.29.11.l) N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide; M.29.11.m) N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide; M.29.11.n) 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide; M.29.11.o) 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide; M.29.11.p) N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; or a compound selected from the group of M.29.12, wherein the compound is selected from M.29.12a) to M.29.12m): M.29.12.a) 2-(1,3-Dioxan-2-yl)-6-[2-(3-pyridinyl)-5-thiazolyl]-pyridine; M.29.12.b) 2-[6-[2-(5-Fluoro-3-pyridinyl)-5-thiazolyl]-2-pyridinyl]-pyrimidine; M.29.12.c) 2-[6-[2-(3-Pyridinyl)-5-thiazolyl]-2-pyridinyl]-pyrimidine; M.29.12.d) N-Methylsulfonyl-6-[2-(3-pyridyl)thiazol-5-yl]pyridine-2-carboxamide; M.29.12.e) N-Methylsulfonyl-6-[2-(3-pyridyl)thiazol-5-yl]pyridine-2-carboxamide; M.29.12.f) N-Ethyl-N-[4-methyl-2-(3-pyridyl)thiazol-5-yl]-3-methyl-thio-propanamide; M.29.12.g) N-Methyl-N-[4-methyl-2-(3-pyridyl)thiazol-5-yl]-3-methylthio-propanamide; M.29.12.h) N,2-Dimethyl-N-[4-methyl-2-(3-pyridyl)thiazol-5-yl]-3-methylthio-propanamide; M.29.12.i) N-Ethyl-2-methyl-N-[4-methyl-2-(3-pyridyl)thiazol-5-yl]-3-methyl-thio-propanamide; M.29.12j) N-[4-Chloro-2-(3-pyridyl)thiazol-5-yl]-N-ethyl-2-methyl-3-methylthio-propanamide; M.29.12.k) N-[4-Chloro-2-(3-pyridyl)thiazol-5-yl]-N,2-dimethyl-3-methylthio-propanamide; M.29.12.l) N-[4-Chloro-2-(3-pyridyl)thiazol-5-yl]-N-methyl-3-methylthio-propanamide; M.29.12.m) N-[4-Chloro-2-(3-pyridyl)thiazol-5-yl]-N-ethyl-3-methylthio-propanamide; or the compounds M.29.14a) 1-[(6-Chloro-3-pyridinyl)methyl]-1,2,3,5,6,7-hexahydro-5-methoxy-7-methyl-8-nitroimidazo[1,2-a]pyridine; or M.29.14b) 1-[(6-Chloropyridin-3-yl)methyl]-7-methyl-8-nitro-1,2,3,5,6,7-hexahydroimidazo[1,2-a]pyridin-5-ol; or the compounds M.29.16a) 1-isopropyl-N,5-dimethyl-N-pyridazin-4-yl-pyrazole-4-carboxamide; or M.29.16b) 1-(1,2-dimethylpropyl)-N-ethyl-5-methyl-N-pyridazin-4-yl-pyrazole-4-carboxamide; M.29.16c) N,5-dimethyl-N-pyridazin-4-yl-1-(2,2,2-trifluoro-1-methyl-ethyl)pyrazole-4-carboxamide; M.29.16d) 1-[1-(1-cyanocyclopropyl)ethyl]-N-ethyl-5-methyl-N-pyridazin-4-yl-pyrazole-4-carboxamide; M.29.16e) N-ethyl-1-(2-fluoro-1-methyl-propyl)-5-methyl-N-pyridazin-4-yl-pyrazole-4-carboxamide; M.29.16f) 1-(1,2-dimethylpropyl)-N,5-dimethyl-N-pyridazin-4-yl-pyrazole-4-carboxamide; M.29.16g) 1-[1-(1-cyanocyclopropyl)ethyl]-N,5-dimethyl-N-pyridazin-4-yl-pyrazole-4-carboxamide; M.29.16h) N-methyl-1-(2-fluoro-1-methyl-propyl)-5-methyl-N-pyridazin-4-yl-pyrazole-4-carboxamide; M.29.16i) 1-(4,4-difluorocyclohexyl)-N-ethyl-5-methyl-N-pyridazin-4-yl-pyrazole-4-carboxamide; or M.29.16j) 1-(4,4-difluorocyclohexyl)-N,5-dimethyl-N-pyridazin-4-yl-pyrazole-4-carboxamide, or M.29.17 a compound selected from the compounds M.29.17a) to M.29.17j): M.29.17a) N-(1-methylethyl)-2-(3-pyridinyl)-2H-indazole-4-carboxamide; M.29.17b) N-cyclopropyl-2-(3-pyridinyl)-2H-indazole-4-carboxamide; M.29.17c) N-cyclohexyl-2-(3-pyridinyl)-2H-indazole-4-carboxamide; M.29.17d) 2-(3-pyridinyl)-N-(2,2,2-trifluoroethyl)-2H-indazole-4-carboxamide; M.29.17e) 2-(3-pyridinyl)-N-[(tetrahydro-2-furanyl)methyl]-2H-indazole-5-carboxamide; M.29.17f) methyl 2-[[2-(3-pyridinyl)-2H-indazol-5-yl]carbonyl]hydrazinecarboxylate; M.29.17g) N-[(2,2-difluorocyclopropyl)methyl]-2-(3-pyridinyl)-2H-indazole-5-carboxamide; M.29.17h) N-(2,2-difluoropropyl)-2-(3-pyridinyl)-2H-indazole-5-carboxamide; M.29.17i) 2-(3-pyridinyl)-N-(2-pyrimidinylmethyl)-2H-indazole-5-carboxamide; M.29.17j) N-[(5-methyl-2-pyrazinyl)methyl]-2-(3-pyridinyl)-2H-indazole-5-carboxamide, or M.29.18 a compound selected from the compounds M.29.18a) to M.29.18d): M.29.18a) N-[3-chloro-1-(3-pyridyl)pyrazol-4-yl]-N-ethyl-3-(3,3,3-trifluoropropylsulfanyl)propanamide; M.29.18b) N-[3-chloro-1-(3-pyridyl)pyrazol-4-yl]-N-ethyl-3-(3,3,3-trifluoropropylsulfinyl)propanamide; M.29.18c) N-[3-chloro-1-(3-pyridyl)pyrazol-4-yl]-3-[(2,2-difluorocyclopropyl)methylsulfanyl]-N-ethyl-propanamide; M.29.18d) N-[3-chloro-1-(3-pyridyl)pyrazol-4-yl]-3-[(2,2-difluorocyclopropyl)methylsulfinyl]-N-ethyl-propanamide; or the compound M.29.19 sarolaner, or the compound M.29.20 lotilaner.

The commercially available compounds of the group M listed above may be found in The Pesticide Manual, 16th Edition, C. MacBean, British Crop Protection Council (2013) among other publications. The online Pesticide Manual is updated regularly and is accessible through http://bcpcdata.com/pesticide-manual.html.

Another online data base for pesticides providing the ISO common names is http://www.alanwood.net/pesticides.

The M.4 neonicotinoid cycloxaprid is known from WO2010/069266 and WO2011/069456, the neonicotinoid M.4A.2, sometimes also to be named as guadipyr, is known from WO2013/003977, and the neonicotinoid M.4A.3 (approved as paichongding in China) is known from WO2007/101369. The metaflumizone analogue M.228.1 is described in CN10171577 and the analogue M.228.2 in CN102126994. The phthalamides M.28.1 and M.28.2 are both known from WO2007/101540. The anthranilamide M.28.3 is described in WO2005/077934. The hydrazide compound M.28.4 is described in WO2007/043677. The anthranilamides M.28.5a) to M.28.5d) and M.28.5h) are described in WO 2007/006670, WO2013/024009 and WO2013/024010, the anthranilamide M.28.5i) is described in WO2011/085575, M.28.5j) in WO2008/134969, M.28.5k) in US2011/046186 and M.28.5l) in WO2012/034403. The diamide compound M.28.6 can be found in WO2012/034472. The spiroketal-substituted cyclic ketoenol derivative M.29.3 is known from WO2006/089633 and the biphenyl-substituted spirocyclic ketoenol derivative M.29.4 from WO2008/067911. The triazoylphenylsulfide M.29.5 is described in WO2006/043635, and biological control agents on the basis of *Bacillus firmus* are described in WO2009/124707. The compounds M.29.6a) to M.29.6i) listed under M.29.6 are described in WO2012/029672, and M.29.6j) and M.29.6k) in WO2013/129688. The nematicide M.29.8 is known from WO2013/055584. The isoxazoline M.29.9.a) is described in WO2013/050317. The isoxazoline M.29.9.b) is described in WO2014/126208. The pyridalyl-type analogue M.29.10 is known from WO2010/060379. The carboxamides broflanilide and M.29.11.b) to M.29.11.h) are described in WO2010/018714, and the carboxamides M.29.11i) to M.29.11.p) in WO2010/127926. The pyridylthiazoles M.29.12.a) to M.29.12.c) are known from WO2010/006713, M.29.12.d) and M.29.12.e) are known from WO2012/000896, and M.29.12.f) to M.29.12.m) from WO2010/129497. The compounds M.29.14a) and M.29.14b) are known from WO2007/101369. The pyrazoles M.29.16.a) to M.29.16h) are described in WO2010/034737, WO2012/084670, and WO2012/143317, respectively, and the pyrazoles M.29.16i) and M.29.16j) are described in U.S. 61/891,437. The pyridinylindazoles M.29.17a) to M.29.17.j) are described in WO2015/038503. The pyridylpyrazoles M.29.18a) to M.29.18d) are described in US2014/0213448. The isoxazoline M.29.19 is described in WO2014/036056. The isoxazoline M.29.20 is known from WO2014/090918.

The following list of fungicides, in conjunction with which the compounds of the present invention can be used, is intended to illustrate the possible combinations but does not limit them:

A) Respiration Inhibitors

Inhibitors of complex III at $Q_o$ site (e. g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxy.strobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A.1.22), 1-[3-chloro-2-[[1-(4-chlorophenyl)-1H-pyrazol-3-yl]oxymethyl]phenyl]-4-methyl-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetrazol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolyl)thiazol-2-yl]oxymethyl]phenyl]-4-methyl-tetrazol-5-one (A.1.29), 1-[3-cyclopropyl-2-[[2-methyl-4-(1-methylpyrazol-3-yl)phenoxy]methyl]phenyl]-4-methyl-tetrazol-5-one (A.1.30), 1-[3-(difluoromethoxy)-2-[[2-methyl-4-(1-methylpyrazol-3-yl)phenoxy]methyl]phenyl]-4-methyl-tetrazol-5-one (A.1.31), 1-methyl-4-[3-methyl-2-[[2-methyl-4-(1-methylpyrazol-3-yl)phenoxy]methyl]phenyl]tetrazol-5-one (A.1.32), 1-methyl-4-[3-methyl-2-[[1-[3-(trifluoromethyl)phenyl]-ethylideneamino]oxymethyl]phenyl]tetrazol-5-one (A.1.33), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), (Z,2E)-5-[1-(4-chloro-2-fluoro-phenyl)pyrazol-3-yl]oxy-2-methoxyimino-N,3-dimethyl-pent-3-enamide (A.1.36), inhibitors of complex III at $Q_i$ site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate (A.2.3), [(3S,6S,7R,8R)-8-benzyl-3-[[3-(acetoxymethoxy)-4-methoxypyridine-2-carbonyl]amino]-6-methyl-4,9-dioxo-1,5-dioxonan-7-yl] 2-methylpropanoate (A.2.4), [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7), (3S,6S,7R,8R)-8-benzyl-3-[3-[(isobutyryloxy)methoxy]-4-methoxypicolinamido]-6-methyl-4,9-dioxo-1,5-dioxonan-7-yl isobutyrate (A.2.8);

inhibitors of complex II (e. g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)-phenyl)-1,3-dimethyl-5-fluoro-1H-pyrazole-4-carboxamide (A.3.20), 3-(difluoromethyl)-1-methyl-N-(1,1,3-trimethylindan-4-yl)pyrazole-4-carboxamide (A.3.21), 3-(trifluoromethyl)-1-methyl-N-(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methyl-ethyl]-3-(difluoromethyl)-1-methyl-pyrazole-4-carboxamide (A.3.27);

other respiration inhibitors (e. g. complex I, uncouplers): diflumetorim (A.4.1), (5,8-difluoroquinazolin-4-yl)-{2-[2-fluoro-4-(4-trifluoromethylpyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol Biosynthesis Inhibitors (SBI Fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S,3R)-3-(2-chlorophenyl)-2-(2,4-difluorophenyl)-oxiranylmethyl]-5-thiocyanato-1H-[1,2,4]triazolo (B.1.31), 2-[rel-(2S,3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chlorophenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.51); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluorophenyl)isoxazol-4-yl]-(3-pyridyl)methanol (B.1.50);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of Cell Division and Cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of Amino Acid and Protein Synthesis methionine synthesis inhibitors (anilino-pyrimidines): cyprodinil (E.1.1), mepanipyrim (E.1.2), pyrimethanil (E.1.3);

protein synthesis inhibitors: blasticidin-S(E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal Transduction Inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenypethanesulfonyl)-but-2-yl) carbamic acid-(4-fluorophenyl) ester (G.3.8);

compounds affecting cell membrane permeability and fatty acids: propamocarb (G.4.1);

fatty acid amide hydrolase inhibitors: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3);

H) Inhibitors with Multi Site Action inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds (e. g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methylbenzenesulfonamide (H.3.12);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (1.1.1), polyoxin B (1.1.2);

melanin synthesis inhibitors: pyroquilon (1.2.1), tricyclazole (1.2.2), carpropamid (1.2.3), dicyclomet (1.2.4), fenoxanil (1.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown Mode of Action bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquat-methylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothal-isopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (K.1.29), N-(cyclopropylmethoxyimino-(6-difluoromethoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethylsilanyl-propoxy)-phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl) cyclopropane-carboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyl-tetrazol-5-yl)-phenyl-methylene]amino]oxymethyl]-2-pyridyl]carbamate (K.1.42), 2-[2-[(7,8-difluoro-2-methyl-3-quinolyl)oxy]-6-fluoro-phenyl]propan-2-01 (K.1.43), 2-[2-fluoro-6-[(8-fluoro-2-methyl-3-quinolyl)oxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl) quinoline (K.1.47), 9-fluoro-2,2-dimethyl-5-(3-quinolyl)-3H-1,4-benzoxazepine (K.1.48).

The fungicides described by common names, their preparation and their activity e.g. against harmful fungi is known (cf.: http://www.alanwood.net/pesticides/); these substances are commercially available.

The fungicides described by IUPAC nomenclature, their preparation and their pesticidal activity is also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

Biopesticides

Suitable mixing partners for the compounds of the present invention also include biopesticides.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classified as microbial pesticides, even though they are multicellular.

(2) Biochemical pesticides are naturally occurring substances or structurally-similar and functionally identical to a naturally-occurring substance and extracts from biological sources that control pests or provide other crop protection uses as defined below, but have non-toxic mode of actions (such as growth or developmental regulation, attractants, repellents or defense activators (e.g. induced resistance) and are relatively non-toxic to mammals.

Biopesticides for use against crop diseases have already established themselves on a variety of crops. For example, biopesticides already play an important role in controlling downy mildew diseases. Their benefits include: a 0-Day Pre-Harvest Interval, the ability to use under moderate to severe disease pressure, and the ability to use in mixture or in a rotational program with other registered pesticides.

A major growth area for biopesticides is in the area of seed treatments and soil amendments. Biopesticidal seed treatments are e.g. used to control soil borne fungal pathogens that cause seed rots, damping-off, root rot and seedling blights. They can also be used to control internal seed borne fungal pathogens as well as fungal pathogens that are on the surface of the seed. Many biopesticidal products also show capacities to stimulate plant host defenses and other physiological processes that can make treated crops more resistant to a variety of biotic and abiotic stresses or can regulate plant growth. Many biopesticidal products also show capacities to stimulate plant health, plant growth and/or yield enhancing activity.

The following list of biopesticides, in conjunction with which the compounds of the present invention can be used, is intended to illustrate the possible combinations but does not limit them:

L) Biopesticides

L1) Microbial pesticides with fungicidal, bactericidal, viricidal and/or plant defense activator activity: *Ampelomyces quisqualis, Aspergillus flavus, Aureobasidium pullulans, Bacillus altitudinis; B. amyloliquefaciens, B. megaterium, B. mojavensls; B. mycoldes, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowla fructicola, Microdochlum climerum, Microsphaeropsis ochracea, Muscodor albus, Paenibacillus alvei, Paenibacillus polymyxa, Pantoea vagans, Penicillium bilaiae, Phleblopsis gigantea, Pseudomonas* sp., *Pseudomonas chloraphls, Pseudozyma flocculosa, Pichia aromala, Pythium ollgandrum, Sphaerodes mycoparasitica, Streptomyces griseoviridis; S. lydicus, S. violaceusniger, Talaromyces flavus, Trichoderma asperelloides, T. asperellum, T. atroviride, T. fertile, T. gamsli, T. harmatum, T. harzianum, T. polysporum, T. stromaticum, T. virens, T. wide, Typhula phacorrhiza, Ulocladium ouclemansii Verticillium dahlia,* zucchini yellow mosaic virus (avirulent strain);

L2) Biochemical pesticides with fungicidal, bactericidal, viricidal and/or plant defense activator activity: harpin protein, *Reynoutria sachalinensis* extract;

L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai B. t.* ssp. *israelensis, B. t.* ssp. *galleriae, B. t.* ssp. *kurstakt; B. t.* ssp. *tenebrionis, Beauveria bassiana, B. brongniartii, Burkholderia* spp., *Chromobacterium subtsugae, Cydia pomonella* granulovirus (CpGV), *Cryptophlebia leucotreta* granulovirus (CrleGV), *Flavobacterium* spp., *Helicoverpa armigera* nucleopolyhedrovirus (HearNPV), *Helicoverpa zea* nucleopolyhedrovirus (HzNPV), *Helicoverpa zea* single capsid nucleopolyhedrovirus (HzSNPV), *Heterorhabditis bacteriophora, Isaria fumosorosea, Lecanicillium longisporum, L. muscarium, Metarhizium anisopliae, Metarhizium anisopliae* var. *anisopliae, M. anisopliae* var. *acridum, Nomuraea rileyi, Paecilomyces fumosoroseus, P. Illacinus, Paenibacillus popilliae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinernema carpocapsae, S. feltiae, S. kraussei; Streptomyces galbus, S. microfiavus,*

L4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, extract of *Chenopodium ambrosiodes*, Neem oil, Quillay extract;

L5) Microbial pesticides with plant stress reducing, plant growth regulator, plant growth promoting and/or yield enhancing activity: *Azospirillum amazonense, A. brasilense, A. lipoferum, A. irakense, A. halopraeferens, Bradyrhizobium* spp., *B. elkanii, B. Japonicum, B. liaoningense, B. lupine; Delftia acidovorans, Glomus intraradices, Mesorhizobium* spp., *Rhizobium leguminosarum* bv. *phaseoli, R. I.* bv. *trifolii, R. I.* bv. *viciae, R. tropic,* Sinorhizobium mellloti.

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) may also have fungicidal, bactericidal, viricidal, plant defense activator, insecticidal, acaricidal, molluscidal, pheromone and/or nematicidal activity.

Many of these biopesticides have been deposited under deposition numbers mentioned herein (the prefices such as ATCC or DSM refer to the acronym of the respective culture collection, for details see e. g. here: http://www.wfcc.info/ccinfo/collection/by_acronym/), are referred to in literature, registered and/or are commercially available: mixtures of *Aureobasidium pullulans* DSM 14940 and DSM 14941 isolated in 1989 in Konstanz, Germany (e. g. blastospores in Blossom-Protect® from bio-ferm GmbH, Austria), *Azosplrillum brasllense* Sp245 originally isolated in wheat region of South Brazil (Passo Fundo) at least prior to 1980 (BR 11005; e. g. GELFIX® Gramineas from BASF Agricultural Specialties Ltd., Brazil), *A. brasllense* strains Ab-V5 and Ab-V6 (e. g. in AzoMax from Novozymes BioAg Produtos papra Agricultura Ltda., Quattro Barras, Brazil or Simbiose-Maíz® from Simbiose-Agro, Brazil; Plant Soil 331, 413-425, 2010), *Bacillus amyloliquefaciens* strain AP-188 (NRRL B-50615 and B-50331; U.S. Pat. No. 8,445,255); *B. amyloliquefaciens* spp. *plantarum* D747 isolated from air in Kikugawa-shi, Japan (US 20130236522 A1; FERM BP-8234; e. g. Double Nickel™ 55 WDG from Certis LLC, USA), *B. amyloliquefaciens* spp. *plantarum* FZB24 isolated from soil in Brandenburg, Germany (also called 5133615; DSM 96-2; J. Plant Dis. Prot. 105, 181-197, 1998; e. g. Taegro® from Novozyme Biologicals, Inc., USA), *B. amyloliquefaciens* ssp. *plantarum* FZB42 isolated from soil in Brandenburg, Germany (DSM 23117; J. Plant Dis. Prot. 105, 181-197, 1998; e. g. RhizoVital® 42 from AbiTEP GmbH, Germany), *B. amyloliquefaciens* ssp. *plantarum* MBI600 isolated from faba bean in Sutton Bonington, Nottinghamshire, U.K. at least before 1988 (also called 1430; NRRL B-50595; US 2012/0149571 A1; e. g. Integral® from BASF Corp., USA), *B. amyloliquefaciens* spp. *plantarum* QST-713 isolated from peach orchard in 1995 in California, U.S.A. (NRRL B-21661; e. g. Serenade® MAX from Bayer Crop Science LP, USA), *B. amyloliquefaciens* spp. *plantarum* TJ1000 isolated in 1992 in South Dakota, U.S.A. (also called 1BE; ATCC BAA-390; CA 2471555 A1; e. g. QuickRoots™ from TJ Technologies, Watertown, S. Dak., USA), *B. firmus* CNCM 1-1582, a variant of parental strain EIP-N1 (CNCM 1-1556) isolated from soil of central plain area of Israel (WO 2009/126473, U.S. Pat. No. 6,406, 690; e. g. Votivo® from Bayer CropScience LP, USA), *B. pumilus* GHA 180 isolated from apple tree rhizosphere in Mexico (IDAC 260707-01; e. g. PRO-MIX® BX from Premier Horticulture, Quebec, Canada), *B. pumilus* INR-7 otherwise referred to as BU-F22 and BU-F33 isolated at least before 1993 from cucumber infested by *Erwinia tracheiphila* (NRRL B-50185, NRRL B-50153; U.S. Pat. No. 8,445,255), (NRRL B-50754; WO 2014/029697; *B. pumilus* QST 2808 was isolated from soil collected in Pohnpei, Federated States of Micronesia, in 1998 (NRRL B-30087; e. g. Sonata® or Ballad® Plus from Bayer Crop Science LP, USA), *B. simplex* ABU 288 (NRRL B-50304; U.S. Pat. No. 8,445,255), *B. subtilis* FB17 also called UD 1022 or UD10-22 isolated from red beet roots in North America (ATCC PTA-11857; System. Appl. Microbiol. 27, 372-379, 2004; US 2010/0260735; WO 2011/109395); *B. thuringiensis* ssp. *aizawai* ABTS-1857 isolated from soil taken from a lawn in Ephraim, Wis., U.S.A., in 1987 (also called ABG-6346; ATCC SD-1372; e. g. XenTari® from BioFa AG, Münsingen, Germany), *B. t.* ssp. *kurstaki* ABTS-351 identical to HD-1 isolated in 1967 from diseased Pink Bollworm black larvae in Brownsville, Tex., U.S.A. (ATCC SD-1275; e. g. Dipel® DF from Valent BioSciences, IL, USA), *B. t.* ssp. *kurstaki* SB4 isolated from *E. saccharina* larval cadavers (NRRL B-50753; *B. t.* ssp. *tenebrionis* NB-176-1, a mutant of strain NB-125, a wild type strain isolated in 1982 from a dead pupa of the beetle *Tenebrio molitor* (DSM 5480; EP 585 215 B1; e. g. Novodor® from Valent BioSciences, Switzerland), *Beauveria bassiana* GHA (ATCC 74250; e. g. BotaniGard® 22WGP from Laverlam Int. Corp., USA), *B. bassiana* JW-1 (ATCC 74040; e. g. Naturalis® from CBC (Europe) S.r.l., Italy), *B. bassiana* PPRI 5339 isolated from the larva of the tortoise beetle *Conchyloctenia punctata* (NRRL 50757), *Bradyrhizobium elkanii* strains SEMIA 5019 (also called 29W) isolated in Rio de Janeiro, Brazil and SEMIA 587 isolated in 1967 in the State of Rio Grande do Sul, from an area previously inoculated with a North American isolate, and used in commercial inoculants since 1968 (Appl. Environ. Microbiol. 73(8), 2635, 2007; e. g. GELFIX 5 from BASF Agricultural Specialties Ltd., Brazil), *B. japonicum* 532c isolated from Wisconsin field in U.S.A. (Nitragin 61A152; Can. J. Plant. Sci. 70, 661-666, 1990; e. g. in Rhizoflo®, Histick®, Hicoat® Super from BASF Agricultural Specialties Ltd., Canada), *B. japonicum* E-109 variant of strain USDA 138 (INTA E109, SEMIA 5085; Eur. J. Soil Biol. 45, 28-35, 2009; Biol. Fertil. Soils 47, 81-89, 2011); *B. japonicum* strains deposited at SEMIA known from Appl. Environ. Microbiol. 73(8), 2635, 2007: SEMIA 5079 isolated from soil in Cerrados region, Brazil by Embrapa-Cerrados used in commercial inoculants since 1992 (CPAC 15; e. g. GELFIX 5 or ADHERE 60 from BASF Agricultural Specialties Ltd., Brazil), *B. japonicum* SEMIA 5080 obtained under lab conditions by Embrapa-Cerrados in Brazil and used in commercial inoculants since 1992, being a natural variant of SEMIA 586 (CB1809) originally isolated in U.S.A. (CPAC 7; e. g. GELFIX 5 or ADHERE 60 from BASF Agricultural Specialties Ltd., Brazil); *Burkholderia* sp. A396 isolated from soil in Nikko, Japan, in 2008 (NRRL B-50319; WO 2013/032693; Marrone Bio Innovations, Inc., USA), *Coniothyrium minitans* CON/M/91-08 isolated from oilseed rape (WO 1996/021358; DSM 9660; e. g. Contans® WG, Intercept® WG from Bayer CropScience AG, Germany), harpin (alpha-beta) protein (Science 257, 85-88, 1992; e. g. Messenger™ or HARP-N-Tek from Plant Health Care plc, U.K.), *Helicoverpa armigera* nucleopolyhedrovirus (HearNPV) (J. Invertebrate Pathol. 107, 112-126, 2011; e. g. Helicovex® from Adermatt Biocontrol, Switzerland; Diplomata® from Koppert, Brazil; Vivus® Max from AgBiTech Pty Ltd., Queensland, Australia), *Helicoverpa zea* single capsid nucleopolyhedrovirus (HzSNPV) (e. g. Gemstar® from Certis LLC, USA), *Helicoverpa zea* nucleopolyhedrovirus ABA-NPV-U (e. g. Heligen® from AgBiTech Pty Ltd., Queensland, Australia), *Heterorhabditis bacteriophora* (e. g. Nemasys® G from BASF Agricultural Specialities Limited, UK), *Isaria fumosorosea* Apopka-97 isolated from mealy bug on gynura in Apopka, Fla., U.S.A. (ATCC 20874; Biocontrol Science Technol. 22(7), 747-761, 2012; e. g. PFR97™ or PreFeRal® from Certis LLC, USA), *Metarhizium anisopliae* var. *anisopliae* F52 also called 275 or V275 isolated from codling moth in Austria (DSM 3884, ATCC 90448; e. g. Met52® Novozymes Biologicals BioAg Group, Canada), *Metschnikowia fructicola* 277 isolated from grapes in the central part of Israel (U.S. Pat. No. 6,994,849; NRRL Y-30752; e. g. formerly Shemer® from Agrogreen, Israel), *Paecilomyces ilacinus* 251 isolated from infected nematode eggs in the Philippines (AGAL 89/030550; WO1991/02051; Crop Protection 27, 352-361, 2008; e. g. BioAct® from Bayer CropScience AG, Germany and MeloCon® from Certis, USA), *Pasteuria nishizawae* Pn1 isolated from a soybean field in the mid-2000s in Illinois, U.S.A. (ATCC SD-5833; Federal Register 76(22), 5808, Feb. 2, 2011; e.g. Clariva™ PN from Syngenta Crop Protection, LLC, USA), *Penicillium bilaiae* (also called *P. bilail*) strains ATCC 18309 (=ATCC 74319), ATCC 20851 and/or ATCC 22348 (=ATCC 74318) originally isolated from soil in Alberta, Canada (Fertilizer Res. 39, 97-103, 1994; Can. J. Plant Sci. 78(1), 91-102, 1998; U.S. Pat. No. 5,026,417, WO 1995/017806; e. g. Jump Start®, Provide® from Novozymes Biologicals BioAg Group, Canada), *Reynoutria sachalinensis* extract (EP 0307510 B1; e. g. Regalia® SC from Marrone BioInnovations, Davis, Calif., USA or Milsana® from BioFa AG, Germany), *Steinernema carpocapsae* (e. g. Millenium® from BASF Agricultural Specialities Limited, UK), *S. feltiae* (e. g. Nemashield® from BioWorks, Inc., USA; Nemasys® from BASF Agricultural Specialities Limited, UK), *Streptomyces microflavus* NRRL B-50550 (WO 2014/124369; Bayer CropScience, Germany), *T. harzianum* T-22 also called KRL-AG2 (ATCC 20847; BioControl 57, 687-696, 2012; e. g. Plantshield® from BioWorks Inc., USA or SabrEx™ from Advanced Biological Marketing Inc., Van Wert, Ohio, USA).

According to the invention, the solid material (dry matter) of the biopesticides (with the exception of oils such as Neem oil) are considered as active components (e.g. to be obtained after drying or evaporation of the extraction or suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1\times10^{10}$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as *Steinernema feltiae*.

When mixtures comprising microbial pesticides are employed in crop protection, the application rates preferably range from about 1×106 to 5×1015 (or more) CFU/ha, preferably from about 1×108 to about 1×1013 CFU/ha, and even more preferably from about 1×109 to about 1×1012 CFU/ha. In the case of (entomopathogenic) nematodes as microbial pesticides (e. g. *Steinernema feltiae*), the application rates preferably range inform about 1×105 to 1×1012 (or more), more preferably from 1×108 to 1×1011, even more preferably from 5×108 to 1×1010 individuals (e. g. in the form of eggs, juvenile or any other live stages, preferably in an infective juvenile stage) per ha.

When mixtures comprising microbial pesticides are employed in seed treatment, the application rates with respect to plant propagation material preferably range from about 1×106 to 1×1012 (or more) CFU/seed. Preferably, the concentration is about 1×106 to about 1×109 CFU/seed. In the case of the microbial pesticides II, the application rates with respect to plant propagation material also preferably range from about 1×107 to 1×1014 (or more) CFU per 100 kg of seed, preferably from 1×109 to about 1×1012 CFU per 100 kg of seed.

Formulations

The invention also relates to agrochemical compositions comprising an auxiliary and at least one compound of the present invention or a mixture thereof.

An agrochemical composition comprises a pesticidally effective amount of a compound of the present invention or a mixture thereof. The term "pesticidally effective amount" is defined below.

The compounds of the present invention or the mixtures thereof can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials (e.g. GF). These and further compositions types are defined in the "Catalogue of pesticide formulation types and international coding system", Technical Mono-graph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Ag row Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protec-tive colloids, adhesion agents, thickeners, humectants, repellents, attractants, feeding stimu-lants, compatibilizers, bactericides, anti-freezing agents, anti-foaming agents, colorants, tackifi-ers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, al-kylated naphthalenes; alcohols, e.g. ethanol, propanol, butanol, benzylalcohol, cyclo¬hexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Voll: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl-sulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethox-ylated alcohols, or of fatty acid esters. Examples of phosphates are phosphate esters. Exam-pies of carboxylates are alkyl carboxylates, and carboxylated alcohol or alkylphenol eth-ovlates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Exam-pies of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the present invention on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazoli-nones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-Soluble Concentrates (SL, LS)

10-60 wt % of a compound I according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible Concentrates (DC)

5-25 wt % of a compound I according to the invention and 1-10 wt % dispersant (e. g. polyvinylpyrrolidone) are dissolved in up to 100 wt % organic solvent (e.g. cyclohexanone). Dilution with water gives a dispersion.

iii) Emulsifiable Concentrates (EC)

15-70 wt % of a compound I according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)

5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active sub-stance. For FS type composition up to 40 wt % binder (e.g. polyvinylalcohol) is added.

vi) Water-Dispersible Granules and Water-Soluble Granules (WG, SG)

50-80 wt % of a compound I according to the invention are ground finely with addition of up to 100 wt % dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I according to the invention are ground in a rotor-stator mill with ad-dition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dis-persion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active sub-stance. Dilution with water gives a stable suspension of the active substance.

ix) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water up to 100%. This mixture is stirred for 1 h to produce spontaneously a thermodynamically stable microemulsion.

x) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radi-cal initiator results in the formation of poly(meth)acrylate microcapsules. Alternatively, an oil phase comprising 5-50 wt % of a compound I according to the invention, 0-40 wt % water insolu-ble organic solvent (e.g. aromatic hydrocarbon), and an isocyanate monomer (e.g. diphenylme-thene-4,4'-diisocyanatae) are dispersed into an aqueous solution of a protective colloid (e.g. polyvinyl alcohol). The addition of a polyamine (e.g. hexamethylenediamine) results in the for-mation of a polyurea microcapsule. The monomers amount to 1-10 wt %. The wt % relate to the total CS composition.

xi) Dustable Powders (DP, DS)

1-10 wt % of a compound I according to the invention are ground finely and mixed intimately with up to 100 wt % solid carrier, e.g. finely divided kaolin.

xii) Granules (GR, FG)

0.5-30 wt % of a compound I according to the invention is ground finely and associated with up to 100 wt % solid carrier (e.g. silicate). Granulation is achieved by extrusion, spray-drying or the fluidized bed.

xiii) Ultra-Low Volume Liquids (UL)

1-50 wt % of a compound I according to the invention are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active sub-stance. The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage de-vice, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising compounds of the present invention and/or mixing partners as defined above, may be mixed by the user in a spray tank and further auxiliaries and additives may be added, if appropriate.

In a further embodiment, either individual components of the composition according to the invention or partially premixed components, e. g. components comprising compounds of the present invention and/or mixing partners as defined above, can be applied jointly (e.g. after tank mix) or consecutively.

Application Methods

The compounds of the present invention are suitable for use in protecting crops, plants, plant propagation materials, such as seeds, or soil or water, in which the plants are growing, from attack or infestation by animal pests. Therefore, the present invention also relates to a plant protection method, which comprises contacting crops, plants, plant propagation materials, such as seeds, or soil or water, in which the plants are growing, to be protected from attack or infestation by animal pests, with a pesticidally effective amount of a compound of the present invention. The compounds of the present invention are also suitable for use in combating or controlling animal pests. Therefore, the present invention also relates to a method of combating or controlling animal pests, which comprises contacting the animal pests, their habitat, breeding ground, or food supply, or the crops, plants, plant propagation materials, such as seeds, or soil, or the area, material or environment in which the animal pests are growing or may grow, with a pesticidally effective amount of a compound of the present invention.

The compounds of the present invention are effective through both contact and ingestion. Furthermore, the compounds of the present invention can be applied to any and all developmental stages, such as egg, larva, pupa, and adult.

The compounds of the present invention can be applied as such or in form of compositions comprising them as defined above. Furthermore, the compounds of the present invention can be applied together with a mixing partner as defined above or in form of compositions comprising said mixtures as defined above. The components of said mixture can be applied simultaneously, jointly or separately, or in succession, that is immediately one after another and thereby creating the mixture "in situ" on the desired location, e.g. the plant, the sequence, in the case of separate application, generally not having any effect on the result of the control measures.

The application can be carried out both before and after the infestation of the crops, plants, plant propagation materials, such as seeds, soil, or the area, material or environment by the pests.

Suitable application methods include inter alia soil treatment, seed treatment, in furrow application, and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active compound to the furrow, and closing the furrow. Foliar application refers to the application of the pesticidally active compound to plant foliage, e.g. through spray equipment. For foliar applications, it can be advantageous to modify the behavior of the pests by use of pheromones in combination with the compounds of the present invention. Suitable pheromones for specific crops and pests are known to a skilled person and publicly available from databases of pheromones and semiochemicals, such as http://www.pherobase.com.

As used herein, the term "contacting" includes both direct contact (applying the compounds/compositions directly on the animal pest or plant—typically to the foliage, stem or roots of the plant) and indirect contact (applying the compounds/compositions to the locus, i.e. habitat, breeding ground, plant, seed, soil, area, material or environment in which a pest is growing or may grow, of the animal pest or plant).

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The term "crop" refers to both, growing and harvested crops.

The term "plant" includes cereals, e.g. durum and other wheat, rye, barley, triticale, oats, rice, or maize (fodder maize and sugar maize/sweet and field corn); beet, e.g. sugar beet or fodder beet; fruits, such as pomes, stone fruits or soft fruits, e.g. apples, pears, plums, peaches, nectarines, almonds, cherries, papayas, strawberries, raspberries, blackberries or gooseberries; leguminous plants, such as beans, lentils, peas, alfalfa or soybeans; oil plants, such as rapeseed (oilseed rape), turnip rape, mustard, olives, sunflowers, coconut, cocoa beans, castor oil plants, oil palms, ground nuts or soybeans; cucurbits, such as squashes, pumpkins, cucumber or melons; fiber plants, such as cotton, flax, hemp or jute; citrus fruit, such as oranges, lemons, grapefruits or mandarins; vegetables, such as eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, such as avocados, cinnamon or camphor; energy and raw material plants, such as corn, soybean, rapeseed, sugar cane or oil palm; tobacco; nuts, e.g. walnuts; pistachios; coffee; tea; bananas; vines (table grapes and grape juice grape vines); hop; sweet leaf (also called *Stevia*); natural rubber plants or ornamental and forestry plants, such as flowers (e.g. carnation, petunias, geranium/pelargoniums, pansies and *impatiens*), shrubs, broad-leaved trees (e.g. poplar) or evergreens, e.g. conifers; *eucalyptus*; turf; lawn; grass such as grass for animal feed or ornamental uses. Preferred plants include potatoes sugar beets, tobacco, wheat, rye, barley, oats, rice, corn, cotton, soybeans, rapeseed, legumes, sunflowers, coffee or sugar cane; fruits; vines; ornamentals; or vegetables, such as cucumbers, tomatoes, beans or squashes.

The term "plant" is to be understood as including wild type plants and plants, which have been modified by either conventional breeding, or mutagenesis or genetic engineering, or by a combination thereof.

Plants, which have been modified by mutagenesis or genetic engineering, and are of particular commercial importance, include alfalfa, rapeseed (e.g. oilseed rape), bean, carnation, chicory, cotton, eggplant, *eucalyptus*, flax, lentil, maize, melon, *papaya, petunia*, plum, poplar, potato, rice, soybean, squash, sugar beet, sugarcane, sunflower, sweet pepper, tobacco, tomato, and cereals (e.g. wheat), in particular maize, soybean, cotton, wheat, and rice. In plants, which have been modified by mutagenesis or genetic engineering, one or more genes have been mutagenized or integrated into the genetic material of the plant. The one or more mutagenized or integrated genes are preferably selected from pat, epsps, cry1Ab, bar, cry1Fa2, cry1Ac, cry34Ab1, cry35AB1, cry3A, cryF, cry1F, mcry3a, cry2Ab2, cry3Bb1, cry1A.105, dfr, barnase, vip3Aa20, barstar, als, bxn, bp40, asn1, and ppo5. The mutagenesis or integration of the one or more genes is performed in order to improve certain properties of the plant. Such properties, also known as traits, include abiotic stress tolerance, altered growth/yield, disease resistance, herbicide tolerance, insect resistance, modified product quality, and pollination control. Of these properties, herbicide tolerance, e.g. imidazolinone tolerance, glyphosate tolerance, or glufosinate tolerance, is of particular importance. Several plants have been rendered tolerant to herbicides by mutagenesis, for example Clearfield® oilseed rape being tolerant to imidazolinones, e.g. imazamox. Alternatively, genetic engineering methods have been used to render plants, such as soybean, cotton, corn, beets and oil seed rape, tolerant to herbicides, such as glyphosate and glufosinate, some of which are commercially available under the trade names RoundupReady® (glyphosate) and LibertyLink® (glufosinate). Furthermore, insect resistance is of importance, in particular lepidopteran insect resistance and coleopteran insect resistance. Insect resistance is typically achieved by modifying plants by integrating cry and/or vip genes, which were isolated from *Bacillus thuringiensis* (Bt), and code for the respective Bt toxins. Genetically modified plants with insect resistance are commercially available under trade names including WideStrike®, Bollgard®, Agrisure®, Herculex®, YieldGard®, Genuity®, and Intacta®. Plants may be modified by mutagenesis or genetic engineering either in terms of one property (singular traits) or in terms of a combination of properties (stacked traits). Stacked traits, e.g. the combination of herbicide tolerance and insect resistance, are of increasing importance. In general, all relevant modified plants in connection with singular or stacked traits as well as detailed information as to the mutagenized or integrated genes and the respective events are available from websites of the organizations "International Service for the Acquisition of Agri-biotech Applications (ISAAA)" (http://www.isaaa.org/gmap-provaldatabase) and "Center for Environmental Risk Assessment (CERA)" (http://cera-gmc.org/GMCropDatabase).

It has surprisingly been found that the pesticidal activity of the compounds of the present invention may be enhanced by the insecticidal trait of a modified plant. Furthermore, it has been found that the compounds of the present invention are suitable for preventing insects to become resistant to the insecticidal trait or for combating pests, which already have become resistant to the insecticidal trait of a modified plant. Moreover, the compounds of the present invention are suitable for combating pests, against which the insecticidal trait is not effective, so that a complementary insecticidal activity can advantageously be used.

The term "plant propagation material" refers to all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "seed" embraces seeds and plant propagules of all kinds including but not limited to true seeds, seed pieces, suckers, corms, bulbs, fruit, tubers, grains, cuttings, cut shoots and the like, and means in a preferred embodiment true seeds.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment, in furrow application or of application to the pests dwelling place or nest, the quantity of active ingredient ranges from 0.0001 to 500 g per 100 m$^2$, preferably from 0.001 to 20 g per 100 m$^2$.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The compounds of the present invention are particularly suitable for use in the treatment of seeds in order to protect the seeds from insect pests, in particular from soil-living insect pests, and the resulting seedling's roots and shoots against soil pests and foliar insects. The present invention therefore also relates to a method for the protection of seeds from insects, in particular from soil insects, and of the seedling's roots and shoots from insects, in particular from soil and foliar insects, said method comprising treating the seeds before sowing and/or after pre-germination with a compound of the present invention. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active compound is carried out by spraying or by dusting the seeds before sowing of the plants and before emergence of the plants.

The present invention also comprises seeds coated with or containing the active compound. The term coated with and/or containing generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is for example seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens*.

In addition, the active compound may also be used for the treatment of seeds from plants, which have been modified by mutagenisis or genetic engineering, and which e.g. tolerate the action of herbicides or fungicides or insecticides. Such modified plants have been described in detail above.

Conventional seed treatment formulations include for example flowable concentrates FS, solutions LS, suspoemulsions (SE), powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of the compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

In the treatment of seed, the application rates of the compounds of the invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising a compound of the present invention, or an agriculturally useful salt thereof, as defined herein. The amount of the compound of the present invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The compounds of the present invention may also be used for improving the health of a plant. Therefore, the present invention also relates to a method for improving plant health by treating a plant, plant propagation material and/or the locus where the plant is growing or is to grow with an effective and non-phytotoxic amount of a compound of the present invention.

As used herein "an effective and non-phytotoxic amount" means that the compound is used in a quantity which allows to obtain the desired effect but which does not give rise to any phytotoxic symptom on the treated plant or on the plant grown from the treated propagule or treated soil.

The terms "plant" and "plant propagation material" are defined above.

"Plant health" is defined as a condition of the plant and/or its products which is determined by several aspects alone or in combination with each other such as yield (for example increased biomass and/or increased content of valuable ingredients), quality (for example improved content or composition of certain ingredients or shelf life), plant vigour (for example improved plant growth and/or greener leaves ("greening effect"), tolerance to abiotic (for example drought) and/or biotic stress (for example disease) and production efficiency (for example, harvesting efficiency, processability).

The above identified indicators for the health condition of a plant may be interdependent and may result from each other. Each indicator is defined in the art and can be determined by methods known to a skilled person.

The compounds of the invention are also suitable for use against non-crop insect pests. For use against said non-crop pests, compounds of the present invention can be used as bait composition, gel, general insect spray, aerosol, as ultra-low volume application and bed net (impregnated or surface applied). Furthermore, drenching and rodding methods can be used.

As used herein, the term "non-crop insect pest" refers to pests, which are particularly relevant for non-crop targets, such as ants, termites, wasps, flies, ticks, mosquitos, crickets, or cockroaches.

The bait can be a liquid, a solid or a semisolid preparation (e.g. a gel). The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature (e.g. http://www.pherobase.com), and are known to those skilled in the art.

For use in bait compositions, the typical content of active ingredient is from 0.001 weight % to 15 weight %, desirably from 0.001 weight % to 5% weight % of active compound.

Formulations of the compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents, furthermore auxiliaries such as emulsifiers, perfume oils, if appropriate stabilizers, and, if required, propellants.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder.

The compounds of the present invention and its compositions can be used for protecting wooden materials such as trees, board fences, sleepers, frames, artistic artifacts, etc. and buildings, but also construction materials, furniture, leathers, fibers, vinyl articles, electric wires and cables etc. from ants and/or termites, and for controlling ants and termites from doing harm to crops or human being (e.g. when the pests invade into houses and public facilities).

Customary application rates in the protection of materials are, for example, from 0.001 g to 2000 g or from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

Pests

The compounds of the present invention are especially suitable for efficiently combating animal pests such as arthropods, gastropods and nematodes including but not limited to:

insects from the order of Lepidoptera, for example *Achroia grisella*, *Acleris* spp. such as *A. fimbriana*, *A. gloverana*, *A. variana*; *Acroleplopsis assectella*, *Acronicta major*, *Adoxophyes* spp. such as *A. cyrtosema*, *A. orana*; *Aedia leucomelas*, *Agrotis* spp. such as *A. exclamationis*; *A. fucosa*, *A. ipsilon*, *A. orthogoma*, *A. segetum*, *A. subterranea*; *Alabama argillacea*, *Aleurodicus dispersus*, *Alsophila pometana*, *Ampelophaga rublginosa*, *Amyelois transitella*, *Anacampsis sarcitella*, *Anagasta kuehniella*, *Anarsia lineatella*, *Anisota senatoria*, *Antheraea pernyi*, *Anticarsla* (=*Thermesia*) spp. such as *A. gemmatalis Aparnea* spp., *Aproaerema modicella*, *Archips* spp. such as *A. argyrospila*, *A. fuscocupreanus*, *A. rosana*, *A. xyloseanus*; *Argyresthia conjugella*, *Argyroploce* spp., *Argyrotaenia* spp. such as *A. velutinana*; *Athetis minclara*, *Austroasca vindignsea*, *Autographa gamma*, *Autographa nignsigna*, *Barathra brassicae*, spp., *Bonagota salubncola*, *Borbo cinnara*, *Bucculatrix thurberiella*, *Bupalus piniarius*, *Busseola* spp., *Cacoecia* spp. such as *C. murinana*, *C. podana*; *Cactoblastis cactorum*, *Cadra cautella*, *Calingo brazillensis*, *Caloptilis theivora*, *Capua reticulana*, *Carposina* spp. such as *C. niponensis*; *C. sasakii*; *Cephus* spp., *Chaetocnema aridula*, *Cheimatobia brumata*, *Chilo* spp. such as *C. indicus*, *C. suppressalis*, *C. partellus*; *Choreutis pariana*, *Choristoneura* spp. such as *C. conflictana*, *C. fumiferana*, *C. longicellana*, *C. murinana*, *C. occidentalis*, *C. rosaceana*; *Chlysodeixis* (=*Pseucloplusia*) spp. such as *C. eriosoma*, *C. includens*; *Cirphis unipuncta*, *Clysla ambiguella*, *Cnaphalocerus* spp., *Cnaphalocrocis medinalis*; *Cnephasia* spp., *Cochylls hospes*, *Coleophora* spp., *Colias eurytheme*, *Conopomorpha* spp., *Conotrachelus* spp., *Copitarsia* spp., *Corcyra cephalonica*, *Crambus caliginosellus*, *Crambus teterrellus*, *Crocidosema* (=*Epinotia*) *aporema*, *Cydalima* (=*Diaphania*) *perspectalis*; *Cydia* (=*Carpocapsa*) spp. such as *C. pomonella*, *C. latiferreana*; *Dalaca noctuides*, *Datana integerrima*, *Dasychira pinicola*, *Dendrolimus* spp. such as *D. pini*; *D. spectabills*; *D. sibiricus*; *Desmia funeralis*, *Diaphania* spp. such as *D. nitidalis*; *D. hyalinata*; *Diatraea grandlosella*, *Diatraea saccharalis*; *Diphthera Festiva*, *Earias* spp. such as *E. insulana*, *E. vittella*; *Ecdytolopha aurantianu*, (=*Xylomyges*) *curialis*; *Elasmopalpus lignosellus*, *Eldana saccharina*, *Enclopiza viteana*, *Ennomos subsignana*, *Eoreuma loftini*, *Ephestia* spp. such as *E. cautella*, *E. elutella*, *E. kuehniella*; *Epinotia aporema*, *Epiphyas postvittana*, *Erannis tillaria*, *Erionota thrax*, *Etiella* spp., *Eulla* spp., *Eupoecilla ambiguella*, *Euproctis chlysorrhoea*, *Euxoa* spp., *Evetria boullana*, *Faronta albilinea*, *Feltia* spp. such as *F. subterranean*; *Galleria mellonella*, *Gracillaria* spp., *Grapholita* spp. such as *G. funebrana*, *G. molesta*, *G. inopinata*; *Halysidota* spp., *Harrisina americana*, *Hedylepta* spp., *Helicoverpa* spp. such as *H. armigera* (=*Heliothis armigera*), *H.* zea (=Heiliothis zea); Heiliothis spp. such as *H. assulta*, *H. subflexa*, *H. virescens* Hellula spp. such as *H. undalis*; *H. rogatalis*; *Helocoverpa gelotopoeon*, *Hemlleuca oliviae*, *Herpetogramma licarsisalis*; *Hibernia defoliaria*, *Hofmannophila pseudospretella*, *Homoeosoma electellum*, *Homona magnanima*, *Hypena scabra*, *Hyphantria cunea*, *Hyponomeuta padella*, *Hyponomeuta malinellus*, *Kakivoria flavofasciata*, *Keiferialycopersicella*, *Lambdina fiscellaria fiscellaria*, *Lambdina fiscellaria lugubrosa*, *Lamprosema indicata*, *Laspeyresia molesta*, *Leguminivora glycinivorella*, *Lerodea eufala*, *Leucinodes orbonalis*; *Leucoma salicis*; *Leucoptera* spp. such as *L. coffeella*, *L. scitella*; *Leuminivora lycinivorella*, *Lithocolletis blancardella*, *Lithophane antennata*, *Llattla octo* (=*Amyna axis*), *Lobesia botrana*, *Lophocampa* spp., *Loxagrotis albicosta*, *Loxostege* spp. such as *L. sticticalis*; *L. cereralis Lymantria* spp. such as *L. dispar*, *L. monacha*; *Lyonetia clerkella*, *Lyonetia prunifoliella*, *Malacosoma* spp. such as *M. americanum*, *M. californIcum*, *M. constrictum*, *M. neustria*; *Mamestra* spp. such as *M. brassicae*, *M. configurata*; *Mamstra brassicae*, *Manduca* spp. such as *M. quinquemaculata*, *M. sexta*; *Marasmia* spp, *Marmara* spp., *Maruca testulalis*; *Megalopyge lanata*, *Melanchra picta*, *Melanitis leda*, *Mocis* spp. such as *M. lapites*, *M. repanda*; *Mocis latipes*, *Monochroa fragariae*, *Mythimna separata*, *Nemapogon cloacella*, *Neoleucinodes elegantalis*; *Nepytia* spp., *Nymphula* spp., *Olketicus* spp., *Omiodes indicata*, *Omphisa anastomosalis*; *Operophtera brumata*, *Orgyia pseudotsugata*, *Oria* spp., *Orthaga thyrisalis*; *OstrInia* spp. such as *O. nubilalis Oulema oryzae*, *Paleacrita vernata*, *Panolis flammea*, *Parnara* spp., *Papaipema nebris*, *Papilio cresphontes*, *Paramyelois transltella*, *Paranthrene regalis*, *Paysandisia archon*, *Pectinophora* spp. such as *P. gossypiella*; *Peridroma saucia*, *Perileucoptera* spp., such as *P. coffeella*; *Phalera bucephala*, *Phryganidia californica*, *Phthorimaea* spp. such as *P. operculella*; *Phyllocnistis citrella*, *Phyllonorycter* spp. such as *P. blancardella*, *P. crataegella*, *P. issikii*, *P. ringoniella*; *Pieris* spp. such as *P. brassicae*, *P. rapae*, *P. napi*; *Pilocrocis tripunctata*, *Plathypena scabra*, *Platynota* spp. such as *P. flavedana*, *P. idaeusalis*; *P. stultana*; *Platyptilia carduidactyla*, *Plebejus argus*, *Plodia interpunctella*, *Plusia* spp, *Plutella maculipennis Plutella xylostella*, *Pontia protodica*, *Prays* spp., *Prodenia* spp., *Proxenus lepigone*, *Pseudaletia* spp. such as *P. sequax*, *P. unlpuncta*; *Pyrausta nubllalis*; *Rachlplusla nu*, *Richia albicosta*, *Rhizobius ventralis*, *Rhyaclonia frustrana*, *Sabulodes aegrotata*, *Schizura concinna*, *Schoenobius* spp., *Schreckenstelnia festaliella*, *Scirpophaga* spp. such as *S. incertulas*, *S. innotata*; *Scotia segetum*, *Sesamia* spp. such as *S. inferens*, *Seudyra subflava*, *Sitotroga cerealella*, *Sparganothis pilleriana*, *Spilonota lechriaspis*; *S. ocellana*, *Spodoptera* (=*Lamphygma*) spp. such as *S. cosmoides*, *S. eridania*, *S. exigua*, *S. frugiperda*, *S. latisfascia*, *S. littoralis*, *S. litura*, *S. omithogalli*; *Stigmella* spp., *Stomopteryx subsecivella*, *Strymon bazochii*, *Sylepta derogata*, *Synanthedon* spp. such as *S. exitiosa*, *Tecia solanivora*, *Telehin licus*, *Thaumatopoea pityocampa*, *Thaumatotibia* (=*Cryptophlebia*) *leucotreta*, *Thaumetopoea pityocampa*, *Thecla* spp., *Theresimima ampelophaga*, *Thyrinteina* spp, *Tildenia inconspicuella*, *Tinea* spp. such as *T. cloacella*, *T. pellionella*; *Tineola bisselliella*, *TortriX* spp. such as *T. vindana*; *Trichophaga tapetzella*, *Trichoplusia* spp. such as *T. ni*; *Tuta* (=*Scrobipalpula*) *absoluta*, *Udea* spp. such as *U. rubigalis*; *U. rubigalis*; *Virachola* spp., *Yponomeuta padella*, and *Zeiraphera canadensis* insects from the order of Coleoptera, for example *Acalymma vittatum*, *Acanthoscehdes obtectus*, *Adoretus* spp., *Agelastica Agrilus* spp. such as *A. anxius*, *A. planipennis*; *A. sinuatus*; *Agriotes* spp. such as *A. fuscicollis*; *A. lineatus*, *A. obscurus*; *Alphitoblus diaperinus*, *Amphimallus Anisandrus dispar*, *Anisoplia austriaca*, *Anoblum punctatum*, *Anomala corpulenta*, *Anomala rufocuprea*, *Anoplophora* spp. such as *A. glabripennis Anthonomus* spp. such as *A. eugenii*; *A. grandis*, *A. pomorum*; *Anthrenus* spp., *Aphthona euphoridae*, *Apion* spp., *Apogonia* spp., *Athous haemorrhoidalis*; *Atomaria* spp. such as *A. linearis*; *Attagenus* spp., *Aulacophora femoralis*, *Blastophagus piniperda*, *Blitophaga undata*, *Bruchidius obtectus*, *Bruchus* spp. such as *B. lentis*; *B. pisorum*, *B. rufimanus*; *Byctiscus betulae*, *Callidiellum rufipenne*, *Callopistria flondensis*; *Callosobruchus chinensis*; *Cameraria ohndella*, *Cassida nebulosa*, *Cerotoma trifurcata*, *Cetonia aurata*, *Ceuthorhynchus* spp. such as *C. assimilis*; *C. napi*; *Chaetocnema tibialis*, *Cleonus mendicus*, *Conoderus* spp. such as *C. vespertinus*; *Conotrachelus nenuphar*, *Cosmopolites* spp., *Costelytra zealandica*, *Crioceris asparagl*, *Cryptolestes ferrugineus*, *Cryptorhynchus lapathi Ctenicera* spp. such as *C. destructor*; *Curcullo* spp., *Cylindrocopturus* spp., *Cyclocephala* spp., *Dactylispa balyi*, *Dectes texanus*, *Dermestes* spp., *Diabrotica* spp. such as *D. undecimpunctata*, *D. speciosa*, *D. longicornis*; *D. semipunctata*, *D. virgifera*; *Diaprepes* abbreviates, *Dichocrocis* spp., *Dicladispa armigera*, *Diloboderus abderus*, *Diocalandra frumenti* (*Diocalandra stigmaticollis*), *Enaphalodes rufulus*, *Epilachna* spp. such as *E. varivestis*; *E. vigintioctomaculata*; *Epitrix* spp. such as *E. hirtipennis*; *E. similaris*; *Eutheola humilis*, *Eutinobothrus brasiliensis*; *Faustinus cubae*, *Gibbium psylloides*, *Gnathocerus cornutus*, *Hellula undalis*; *Heteronychus arator*, *Hylamorpha elegans*, *Hylobius abietis*; *Hylotrupes bajulus*, *Hypera* spp. such as *H. brunnelpennis*; *H. postica*; *Hypomeces squamosus*, *Hypothenemus* spp., *Ips typographus*, *Lachnostema consanguinea*, *Lasioderma serricome*, *Latheticus oryzae*, *Lathridius* spp., *Lema* spp. such as *L. bilineata*, *L. melanopus*; *Leptinotarsa* spp. such as *L. decemlineata*; *Leptispa pygmaea*, *Limonius californicus*, *Lissorhoptrus oryzophilus*, *Lixus* spp., *Luperodes* spp., *Lyctus* spp such as *L. bruneus*; *Liogerys fuscus*, *Macrodactylus* spp. such as *M. subspinosus*; *Maladera matrida*, *Megaplatypus mutates*, *Megascelis* spp., *Melanotus communis*, *Meligethes* spp. such as *M. aeneus*; *Melolontha* spp. such as *M. hippocastani*, *M. melolontba*; *Metamasius hemipterus*, *Microtheca* spp., *Migdolus* spp. such as *M. fryanus*, *Monochamus* spp. such as *M. alternatus*; *Naupactus xanthographus*, *Niptus hololeucus*, *Oberia brevis*, *Oemona hirta*, *Oryctes rhinoceros*, *Oryzaephifus surinamensis*, *Oryzaphagus oryzae*, *Otiorrhynchus sulcatus*, *Otiorrhynchus ovatus*, *Otiorrhynchus sulcatus*, *Oulema melanopus*, *Oulema oryzae*, *Oxycetonia jucunda*, *Phaedon* spp. such as *P. brassicae*, *P. cochieariae*; *Phoracantha recurva*, *Phyllobius pyri*, *Phyllopertha horticola*, *Phyllophaga* spp. such as *P. helleri*; *Phyilotreta* spp. such as *P. chrysocephaia*, *P. nemorum*, *P. striolata*, *P. vittula*; *Phyllopertha horticola*, *Popillia japonica*, *Premnotrypes* spp., *Psacothea hifaris*, *Psylliodes chrysocephaia*, *Prostephanus truncates*, *Psylliodes* spp., *Ptinus* spp., *Pulga saltona*, *Rhizopertha dominica*, *Rhynchophorus* spp. such as *R. billineatus*, *R. ferrugineus*, *R. palmarum*, *R. phoenicis*, *R. vulneratus*; *Saperda Candida*, *Scolytus schevyrewi*, *Scyphophorus acupunctatus*, *Sitona lineatus*, *Sitophilus* spp. such as *S. granaria*, *S. oryzae*, *S. zeamais*; *Sphenophorus* spp. such as *S. levis*; *Stegobium paniceum*, *Sternechus* spp. such as *S. subsignatus*; *Strophomorphus ctenotus*, *Symphytetes* spp., *Tanymecus* spp., *Tenebrio molitor*, *Tenebrioides mauretanicus*, *Tribolium* spp. such as *T. castaneum*; *Trogoderma* spp., *Tychius* spp., *Xylotrechus* spp. such as *X. pyrrhoderus*; and, *Zabrus* spp. such as *Z. tenebrioides*;

insects from the order of Diptera for example *Aedes* spp. such as *A. aegypti*, *A. albopictus*, *A. vexans*; *Anastrepha ludens*, *Anopheles* spp. such as *A. albimanus*, *A. crucians*, *A. freeborni*, *A. gambiae*, *A. leucosphyrus*, *A. maculipennis*, *A. minimus*, *A. quadrimaculatus*, *A. sinensis*; *Bactrocera invadens*, *Bibio hortufanus*, *Calliphora erythrocephala*, *Calliphora vicina*, *Ceratitis capitata*, *Chrysomyia* spp. such as *C. bezziana*, *C. hominivorax*, *C. macellaria*; *Chrysops atlanticus*, *Chrysops discalis*, *Chrysops silacea*, *Cochliomyia* spp. such as *C. hominivorax*; *Contarinia* spp. such as *C. sorghicola*; *Cordytobia anthropophaga*, *Culex* spp. such as *C. nigripalpus*, *C. pipiens*, *C. quinquefasciatus*, *C. tarsalis*, *C. tritaeniorhynchus*; *Culicoides furens*, *Culiseta inornata*, *Culiseta melanura*, *Cuterebra* spp., *Dacus cucurbitae*, *Dacus oleae*, *Dasineura brassicae*, *Dasineura oxycoccana*, *Delia* spp. such as *D. antique*, *D. coarctata*, *D. platura*. *D. radicum*; *Dermatobia hominis*, *Drosophila* spp. such as *D. suzukii*, *Fannia* spp. such as *F. canicularis*; *Gastraphilus* spp. such as *G. intestinalis*; *Geomyza tipunctata*, *Glossina* spp. such as *G. fuscipes*, *G. morsitans*, *G. palpalis*, *G. tachinoides*; *Haematobia irritans*, *Haplodiplosis equestris*, *Hippelates* spp., *Hylemyia* spp. such as *H. platura*; *Hypoderma* spp. such as *H. lineata*; *Hyppobosca* spp., *Hydrellia philippina*, *Leptoconops torrens*, *Liriomyza* spp. such as *L. sativae*, *L. trifolii*; *Lucifa* spp. such as *L. caprina*, *L. cuprina*, *L sericata*; *Lycoria pectoralis*, *Mansonia titillanus*, *Mayetiola* spp. such as *M. destructor*; *Musca* spp. such as *M. autumnalis*, *M. domestica*; *Muscina stabulars*, *Oestrus* spp. such as *O. ovis*; *Opomyza florum*, *Oscinella* spp. such as *O. frit*; *Orseolia oryzae*, *Pegomya hysocyami*, *Phlebotomus argentipes*, *Phorbia* spp. such as *P. antiqua*, *P. brassicae*, *P. coarctata*; *Phytomyza gymnostoma*, *Prosimulium mixtum*, *Psila rosae*, *Psorophora columbiae*, *Psorophora discolor*, *Rhagofetis* spp. such as *R. cerasi*, *R. cingutate*, *R. indifferens*, *R. mendax*, *R. pomonella*; *Rivellia quadrifasciata*, *Sarcophaga* spp. such as *S. haemorrhoidalis*; *Simulium vittatum*, *Sitodipfosis mosellana*, *Stomoxys* spp. such as *S. calcitrans*; *Tabanus* spp. such as *T. atratus*, *T. bovinus*, *T. lineola*, *T. similis*; *Tannia* spp, *Thecodiplosis japonensis*, *Tipula oleracea*, *Tipula paludosa*, and *Wohlfahrtia* spp;

insects from the order of Thysanoptera for example, *Baliothrips biformis*, *Dichromothrips corbetti*, *Dichromothrips* ssp., *Echinothrips americanus*, *Enneothrips flavens*, *Frankliniella* spp. such as *F. fusca*, *F occidentalis*, *F. tritici*; *Heliothnps* spp, *Hercinothrips femoralis*, *Kakothrips* spp., *Microcephalothrips abdominalis*, *Neohydatothrips samayunkur*, *Pezothrips kellyanus*, *Rhipiphorothrips cruentatus*, *Scirtothrips* spp. such as *S. citri*, *S. dorsalis*, *S. perseae*; *Stenchaetothrips* spp, *Taeniothrips cardamoni*, *Taeniothrips inconsequens*, *Thrips* spp. such as *T. imagines*, *T. hawaiiensis*, *T. oryzae*, *T. palmi*, *T. parvispinus*, *T. tabaci*;

insects from the order of Hemiptera for example, *Acizzia jamatonica*, *Acrosternum* spp. such as *A. hilare*; *Acyrthosipon* spp. such as *A. onobrychis*, *A. pisum*; *Adelges laricis*, *Adelges tsugae*, *Adelphocoris* spp., such as *A. rapidus*, *A. superbus*; *Aeneolamia* spp., *Agonoscena* spp., *Aulacorthum solani*, *Aleurocanthus woglumi*, *Aleurodes* spp., *Aleurodicus disperses*, *Aleurolobus barodensis*, *Aleurothrixus* spp., *Amrasca* spp., *Anasa tristis*, *Antestiopsis* spp., *Anuraphis cardui*, *Aonidiella* spp., *Aphanostigma piri*, *Aphidula nasturtrii*, *Aphis* spp. such as *A. craccivora*, *A. fabae*, *A. forbesi*, *A. gossypii*, *A. grossutariae*, *A. maiditadicis*, *A. pomi*, *A. sambuci*, *A. schneideri*, *A. spiraecofa*; *Arboridia apicalis*, *Arilus critatus*, *Aspioiella* spp., *Aspidiotus* spp., *Atanus* spp., *Aulacaspis yasumatsui*, *Aulacorthum solani*, *Bactericera cockerelli* (*Paratrioza cockerelli*), *Bemisia* spp. such as *B. argentifolii*, *B. tabaci* (*Aleurodes tabaci*); *Blissus* spp. such as *B. leucopterus*; *Brachycaudus* spp. such as *B. cardui*, *B. helichrysi*, *B. persicae*, *B. prunicola*; *Brachycolus* spp., *Brachycorynella asparagi*, *Brevicoryne brassicae*, *Cacopsylla* spp. such as *C. fulguralis*, *C. pyricola* (*Psylla piri*); *Calligypona marginata*, *Calocoris* spp., *Campylomma livida*, *Capitophorus horni*, *Carneocephala fulgida*, *Cavelerius* spp., *Ceraplastes* spp., *Ceratovacuna lanigera*, *Ceroplastes ceriferus*, *Cerosipha gossypii*, *Chaetosiphon fragaefolii*, *Chionaspis tegalensis*, *Chlorita onukii*, *Chromaphis juglandicola*, *Chrysomphalus ficus*, *Cicadulina mbila*, *Cimex* spp. such as *C. hemipterus*, *C. lectularius*; *Coccomytilus halli*, *Coccus* spp. such as *C. hesperidum*, *C. pseudomagnoliarurum*, *Corythucha arcuata*, *Creontiades dilutus*, *Cryptomyzus ribis*, *Chrysomphalus aonidum*, *Cryptomyzus ribis*, *Ctenarytaina spatulata*, *Cyrtopeltis notatus*, *Dalbulus* spp., *Dasynus piperis*, *Dialeurodes* spp. such as *D. citrifolii*; *Dalbulus maidis*, *Diaphorina* spp. such as *D. citri*; *Diaspis* spp. such as *D. bromeliae*; *Dichelops furcatus*, *Diconocoris hewetti*, *Doratis* spp., *Dreyfusia nordmannianae*, *Dreyfusia piceae*, *Drosicha* spp., *Dysaphis* spp. such as *D. plantaginea*, *D. pyri*, *D. radicola*; *Dysaulacorthum pseudosolani*, *Dysdercus* spp. such as *D. cingulatus*, *D. intermedius*; *Dysmicoccus* spp., *Edessa* spp., *Geocoris* spp., *Empoasca* spp. such as *E. fabae*, *E. sofana*; *Epidiaspis leperii*, *Eriosoma* spp. such as *E. lanigerum*, *E. pyricola*; *Erythroneura* spp., *Eurygaster* spp. such as *E. integriceps*; *Euscelis biiobatus*, *Euschistus* spp. such as *E. heros*, *E. impictiventris*, *E. servus*; *Fiorinia theae*, *Geococcus coffeae*, *Glycaspis brimblecombei*, *Hatyomorpha* spp. such as *H. halys*; *Heliopeltis* spp., *Homalodisca vitripennis* (=*H. coagulata*) *Horcias nobifellus*, *Hyalopterus pruni*, *Hyperomyzus actucae*, *Icerya* spp. such as *I. purchase*; *Idiocerus* spp., *Idioscopus* spp., *Laodelphax striatellus*, *Lecanium* spp., *Lecanoideus floccissimus*, *Lepioosaphes* spp. such as *L. ulmi*; *Leptocorisa* spp., *Leptogfossus phyllopus*, *Lipaphis erysimi*, *Lygus* spp. such as *L. hesperus*, *L. lineolaris*, *L. pratensis*; *Maconellicoccus hirsutus*, *Marchalina hellenica*, *Macropes excavatus*, *Macrosiphum* spp. such as *M. rosae*, *M. avenae*, *M. euphorbiae*; *Macrosteles quadrilineatus*, *Mahanarva fimbriolata*, *Megacopta cribraria*, *Megoura viciae*, *Melanaphis pyarius*, *Melanaphis sacchari*, *Melanocallis* (=*Tinocallis*) *caryaefoliae*, *Metcafiella* spp., *Metopolopbium dirhodum*, *Monellia costatis*, *Monelliopsis pecanis*, *Myzocallis coryli*, *Murgantia* spp., *Myzus* spp. such as *M. ascalonicus*, *M. cerasi*, *M. nicotianae*, *M. persicae*, *M. varians*; *Nasonovia ribisnigri*, *Neotoxoptera formosana*, *Neomegalotomus* spp, *Nephotettix* spp. such as *N. malayanus*, *N. nigropictus*, *N. parvus*, *N. virescens*; *Nezara* spp. such as *N. viridula*; *Nilaparvata lugens*, *Nysius huttoni*, *Oebalus* spp. such as *O. pugnax*; *Oncometopia* spp., *Orthezia praefonga*, *Oxycaraenus hyalinipennis*, *Parabemisia myricae*, *Pariatoria* spp., *Parthenolecanium* spp. such as *P. corni*, *P. persicae*; *Pemphigus* spp. such as *P. bursarius*, *P. populivenae*; *Peregrinus maidis*, *Perkinsiella saccharicida*, *Phenacoccus* spp. such as *P. aceris*, *P. gossypii*; *Phloeomyzus passerinii*, *Phorodon humuli*. *Phylloxera* spp. such as *P. devastatrix*, *Piesma quadrata*, *Piezodorus* spp. such as *P. guildinii*; *Pinnaspis aspidistrae*, *Planococcus* spp. such as *P. citri*, *P. ficus*; *Prosapia bicincta*, *Protopulvinaria pyriformis*,

*Psallus seriatus, Pseudacysta persea, Pseudaulacaspis pentagona, Pseudococcus* spp. such as *P. comstocki; Psylla* spp. such as *P. mali; Pteromalus* spp., *Putvinaria amygdali, Pyrilla* spp., *Quadraspidiotus* spp., such as *Q. pemiciosus; Quesada gigas, Rastrococcus* spp., *Reduvius senilis, Rhizoecus americanus, Rhodnius* spp., *Rhopalomyzus ascaionicus, Rhopalosiphum* spp. such as *R. pseudobrassicas, R. insertum, R. maidis, R padi; Sagatodes* spp., *Sahibergella singuiaris, Saissetia* spp., *Sappaphis mala, Sappaphis mali, Scaptocoris* spp., *Scaphoides titanus, Schizaphis graminum. Schizoneura lanuginosa. Scotinophora* spp., *Selenaspidus articulatus Sitobion avenae, Sogata* spp., *Sogatella furcifera. Sofubea insularis, Spissistitus festinus* (=*Stictocephaa festina*), *Stephanitis nashi, Stephanitis pyrioides, Stephanitis takeyai, Tenalaphara malayensis, Tetraleurodes perseae, Therioaphis maculate, Thyania* spp. such as *T. accerra, T. perditor; Tibraca* spp., *Tomaspis* spp., *Toxoptera* spp. such as *T. aurantii; Triafeurodes* spp. such as *T. abutilonea, T. ridni, T. vaporariorum; Triatoma* spp., *Trioza* spp., *Typhlocyba* spp, *Unaspis* spp. such as *U. citri, U. yanonensis;* and *Viteus vitifolii,*

Insects from the order Hymenoptera for example *Acanthomyops interjectus, Athalia rosae, Alta* spp. such as *A. capiguara, A. cephalotes, A. cephaiotes, A. laevigata, A. robusta, A. sexdens, A. texana, Bombus* spp., *Brachymyrmex* spp., *Camponotus* spp. such as *C. fioridanus, C. pennsytvanicus, C. modoc; Cardiocondyla nuda, Chalibion* sp, *Crematogaster* spp., *Dasymutilla occidental, Diprion* spp., *Dolichovespula maculata, Dorymyrmex* spp., *Dryocosmus kuriphiius, Formica* spp., *Hoplocampa* spp. such as *H. minuta. H. testudinea; Iridomyrmex humilis, Lasius* spp. such as *L. niger, Linepithema humile, Liometopum* spp., *Leptocybe invasa, Monomorium* spp. such as *M. pharaonis, Monomorium, Nytandria futva, Pachycondyla chinensis, Paratrechina tongicomis, Para vespula* spp., such as *P. germanica. P. pennsyivanica, P. vulgaris; Pheidole* spp. such as *P. megacephala; Pogonomyrmex* spp. such as *P. barbatus. P. californicus, Polistes rubiginosa. Prenolepis impairs, Pseudomyrmex gracilis, Schelipron* spp., *Sirex cyaneus, Sofenopsis* spp. such as *S. geminata, S. invicta, S. molesta, S. richteri, S. xyloni, Sphecius speciosus, Sphex* spp., *Tapinoma* spp. such as *T. melanocephalum, T. sessile; Telramorium* spp. such as *T. caespitum, T. bicarinatum. Vespa* spp. such as *V. crabro; Vespula* spp. such as *V. squamosal; Wasmannia auropunctata, Xylocopa* sp;

Insects from the order Orthoptera for example *Acheta domesticus, Calliptamus italicus, Chortoicetes terminifera, Ceuthophllus* spp., *Diastrammena asynamora, Dociostaurus maroccanus, Gryllotalpa* spp. such as *G. africana, G. gryllotalpa; Gryllus* spp., *Hieroglyphus daganensis; Kraussaria angulifera, Locusta* spp. such as *L. migratoria, L. pardallna; Melanoplus* spp. such as *M. bivittatus, M. femurrubrum, M. mexicanus, M. sanguinipes, M. spretus; Nomadacris septemfasciata, Oedaleus senegalensls; Scapteriscus* spp., *Schistocerca* spp. such as *S. americana, S. gregaria, Stemopelmatus* spp., *Tachycines asynamorus,* and *Zonozerus varlegatus*

Pests from the Class Arachnida for example Acari, e.g. of the families Argasidae, Ixodidae and Sarcoptidae, such as *Amblyomma* spp. (e.g. *A. americanum, A. variegatum, A. maculatum*), *Argas* spp. such as *A. persicu*), *Boophilus* spp. such as *B. annulatus, B. decoloratus, B. microplus, Dermacentor* spp. such as *D. silvarum, D. andersoni, D. variabills; Hyalomma* spp. such as *H. truncatum, Ixodes* spp. such as *I. ricinus, I. rubicundus, I. scapularis, I. holocyclus, I. pacificus, Rhipicephalus sanguineus, Ornithodorus* spp. such as *O. moubata, O. hermsi, O. turicata, Ornithonyssus bacoti, Otobius megnini, Dermanyssus gallinae, Psoroptes* spp. such as *P. ovis, Rhipicephalus* spp. such as *R. sanguineus, R. appendiculatus, Rhipicephalus evertsi, Rhizoglyphus* spp., *Sarcoptes* spp. such as *S. Scablei,* and Family Eriophyidae including *Aceria* spp. such as *A. sheldone; A. anthocoptes, Acallitus* spp., *Aculops* spp. such as *A. lycopersici, A. pelekassi, Aculus* spp. such as *A. schlechtendali; Colomerus vitis, Epitrimerus pyri, Phyllocoptruta oleivora; Eriophytes ribis* and *Eriophyes* spp. such as *Eriophyes sheldoni,* Family Tarsonemidae including *Hemitarsonemus* spp., *Phytonemus pallidus* and *Polyphagotarsonemus latus, Stenotarsonemus* spp. *Steneotarsonemus spinki,* Family Tenuipalpidae including *Brevipalpus* spp. such as *B. phoenicis;* Family Tetranychidae including *Eotetranychus* spp., *Eutetranychus* spp., *Oligonychus* spp., *Petrobia latens, Tetranychus* spp. such as *T. cinnabarinus, T. evansi, T. kanzawai, T. pacificus, T. phaseulus, T. telarius* and *T. urticae, Bryobia praetiosa, Panonychus* spp. such as *P. ulmi, P. citri, Metatetranychus* spp. and *Oligonychus* spp. such as *O. pratensis, O. perseae, Vasates lycopersici, Raoiella indica,* Family Carpoglyphidae including *Carpoglyphus* spp.; *Penthaleidae* spp. such as *Halotydeus destructor,* Family Demodicidae with species such as *Demodex* spp; Family Trombkidea including *Trombicula* spp.; Family Macronyssidae including *Ornothonyssus* spp.; Family Pyemotidae including *Pyemotes tritici, Tyrophagus putrescentiae,* Family Acaridae including *Acarus siro,* Family Araneida including *Lalrodectus mactans, Tegenaria agrestis, Chiracanthium* sp, *Lycosa* sp *Achaearanea tepidariorum* and *Loxosceles redusa,*

Pests from the Phylum Nematoda, for example, plant parasitic nematodes such as root-knot nematodes, *Meloidogyne* spp. such as *M. hapta, M. incognita, M. javanica;* cyst-forming nematodes, *Globodera* spp. such as *G. rostocbiensis; Heterodera* spp. such as *H. avenae, H. glycines, H. schachtii, H. trifolii;* Seed gall nematodes, *Anguina* spp.; Stem and foliar nematodes, *Apheienchoides* spp. such as *A. besseyi;* Sting nematodes, *Belonolaimus* spp. such as *B. fongicaudatus;* Pine nematodes, *Bursapheienchus* spp. such as *B. lignicolus, B. xylophilus;* Ring nematodes, *Criconema* spp., *Criconemella* spp. such as *C. xenoplax* and *C. ornata;* and, *Criconemoides* spp. such as *Criconemoides informis; Mesocriconema* spp.; Stem and bulb nematodes, *Dityienchus* spp. such as *D. destructor, D. dipsaci;* Awl nematodes, *Dolichodorus* spp.; Spiral nematodes, *Heliocotylenchus multicinctus;* Sheath and sheathoid nematodes, *Hemicycliophora* spp. and *Hemicriconemoides* spp.; *Hirshmanniella* spp.; Lance nematodes, *Hoploaimus* spp.; False rootknot nematodes, *Nacobbus* spp.; Needle nematodes, *Longidorus* spp. such as *L. elongalus;* Lesion nematodes, *Pratylencbus* spp. such as *P. brachyurus, P. neglectus, P. penetrans, P. curvitatus, P. goodeyi;* Burrowing nematodes, *Radopbolus* spp. such as *R. similis; Rhadopbolus* spp.; *Rbodopholus* spp.; Reniform nematodes, *Rotylenchus* spp. such as *R. robustus, R. reniformis; Scutellonema* spp.; Stubby-root nematode, *Trichodorus* spp. such as *T. obtusus, T. primitivus; Paratrichodorus* spp. such as *P. minor;* Stunt nematodes, *Tyienchorhynchus* spp. such as *T. daytoni, T. dubius;* Citrus nematodes, *Tyienchulus* spp. such as *T. semipenetrans;* Dagger nematodes, *Xiphinema* spp.; and other plant parasitic nematode species;

Insects from the order Isoptera for example *Calotermes flavicoilis, Coptotermes* spp. such as *C. formosanus, C. geslroi, C. acinaciformis; Cornitermes cumulans, Cryptotermes* spp. such as *C. brevis, C. cavifrons; Globilermes sutfureus, Heterotermes* spp. such as *H. aureus, H. longi-* ceps, H. tenuis; Leucotermes flavipes, Odontotermes spp., incisitermes spp. such as *I. minor, I. Snyder, Marginitermes hubbardi, Mastotermes* spp. such as *M. darwiniensis Neocapritermes* spp. such as *N. opacus N. parvus; Neotermes* spp., *Procornitermes* spp., *Zootermopsis* spp. such as *Z. angusticollis, Z. nevadensis, Reticulitermes* spp. such as *R. hesperus, R. tibialis R. speratus, R. fiavipes, R. grassei, R. lucifugus, R. santonensis, R. virginicus; Termes nataiensis,*

Insects from the order *Blattaria* for example *Blatta* spp. such as *B. orientalis, B. lateralis; Blattella* spp. such as *B. asahinae, B. germanica; Leucophaea maderae, Panchlora nivea, Peripfaneta* spp. such as *P. americana, P. austraiasiae, P. brunnea, P. fuligginosa, P. japonica; Supella longipalpa, Parcoblatta pennsylvanica, Eurycotis fioridana, Pycnoscelus surinamensis,*

Insects from the order Siphonoptera for example *Cediopsylla simples, Ceratophyllus* spp., *Ctenocephalides* spp. such as *C. felis, C. canis, Xenopsylla cheopis, Putex irritans, Trichodectes canis, Tunga penetrans* and *Nosopsyllus fasciatus,*

Insects from the order Thysanura for example *Lepisma saccharina, Ctenolepisma urbana,* and *Thermobia domestica.*

Pests from the class Chilopoda for example *Geophilus* spp., *Scutigera* spp. such as *Scutigera coleoptrata,*

Pests from the class Diplopoda for example *Blaniulus guttulatus, Julus* spp., *Narceus* spp., Pests from the class Symphyla for example *Scutigerella immaculata,*

Insects from the order Dermaptera, for example *Forficula auricularia,*

Insects from the order Collembola, for example *Onychiurus* spp., such as *Onychiurus armatus,*

Pests from the order Isopoda for example, *Armadillidium vufgare, Oniscus asellus, Porcellio scaber,*

Insects from the order Phthiraptera, for example *Damalinia* spp., *Pediculus* spp. such as *Pediculus humanus capitis. Pediculus humanus corporis, Pediculus humanus humanus; Pthirus pubis, Haematopinus* spp. such as *Haematopinus eurysternus, Haematopinus suis, Linognathus* spp. such as *Linognathus vituli; Bovicofa bovis, Menopon gallinae, Menacanthus stramineus* and *Solenopotes capillatus, Trichodectes* spp., Examples of further pest species which may be controlled by compounds of formula (I) include: from the Phylum Mollusca, class Bivalvia, for example, *Dreissena* spp.; class Gastropoda, for example, *Arion* spp., *Biomphalaria* spp., *Bulinus* spp., *Deroceras* spp., *Galba* spp., *Lymnaea* spp., *Oncomelania* spp., *Pomacea canaliclata, Succinea* spp; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia matayi, Brugia timori, Bunostomum* spp., *Chabertia* spp., *Cbnorchis* spp., *Coopeha* spp., *Dicrocoellum* spp., *Dictyocaulus filaria, Diphyllobothrium latum, Dracuncutus medinensis, Echinococcus granulosus, Echinococcus multilocularis, Enterobius vermicularis, Faciola* spp., *Haemonchus* spp. such as *Haemonchus contortus; Heterakis* spp., *Hymertolepis nana, Hyostrongufus* spp., *Loa Loa, Nematodirus* spp., *Oesophagostomum* spp., *Opisthorchis* spp., *Onchocerca volvulus. Ostertagia* spp., *Paragonimus* spp., *Schistosomen* spp., *Strongybides fuellebomi, Strongyloides stercora lis, Stronybides* spp., *Taenia saginata. Taenia solium, Trichinella spiralis, Trichinella nativa, Trichinella britovi, Trichinella nelsoni, Trichinella pseudopsirafis, Trichostrongufus* spp, *Trichuris trichiura, Wuchereria bancrofti.*

Animal Health

The compounds of the present invention are suitable for use in treating or protecting animals against infestation or infection by parasites. Therefore, the present invention also relates to the use of a compound of the present invention for the manufacture of a medicament for the treatment or protection of animals against infestation or infection by parasites. Furthermore, the present invention relates to a method of treating or protecting animals against infestation and infection by parasites, which comprises orally, topically or parenterally administering or applying to the animals a parasiticidally effective amount of a compound of the present invention. The present invention also relates to the non-therapeutic use of compounds of the present invention for treating or protecting animals against infestation and infection by parasites. Moreover, the present invention relates to a non-therapeutic method of treating or protecting animals against infestation and infection by parasites, which comprises applying to a locus a parasiticidally effective amount of a compound of the present invention.

The compounds of the present invention are further suitable for use in combating or controlling parasites in and on animals. Furthermore, the present invention relates to a method of combating or controlling parasites in and on animals, which comprises contacting the parasites with a parasitically effective amount of a compound of the present invention.

The present invention also relates to the non-therapeutic use of compounds of the present invention for controlling or combating parasites. Moreover, the present invention relates to a non-therapeutic method of combating or controlling parasites, which comprises applying to a locus a parasiticidally effective amount of a compound of the present invention.

The compounds of the present invention can be effective through both contact (via soil, glass, wall, bed net, carpet, blankets or animal parts) and ingestion (e.g. baits). Furthermore, the compounds of the present invention can be applied to any and all developmental stages.

The compounds of the present invention can be applied as such or in form of compositions comprising the compounds of the present invention.

The compounds of the present invention can also be applied together with a mixing partner, which acts against pathogenic parasites, e.g. with synthetic coccidiosis compounds, polyetherantibiotics such as Amprolium, Robenidin, Toltrazuril, Monensin, Salinomycin, Maduramicin, Lasalocid, Narasin or Semduramicin, or with other mixing partners as defined above, or in form of compositions comprising said mixtures.

The compounds of the present invention and compositions comprising them can be applied orally, parenterally or topically, e.g. dermally. The compounds of the present invention can be systemically or non-systemically effective.

The application can be carried out prophylactically, therapeutically or non-therapeutically. Furthermore, the application can be carried out preventively to places at which occurrence of the parasites is expected.

As used herein, the term "contacting" includes both direct contact (applying the compounds/compositions directly on the parasite, including the application directly on the animal or excluding the application directly on the animal, e.g. at it's locus for the latter) and indirect contact (applying the compounds/compositions to the locus of the parasite). The contact of the parasite through application to its locus is an example of a non-therapeutic use of the compounds of the present invention.

The term "locus" means the habitat, food supply, breeding ground, area, material or environment in which a parasite is growing or may grow outside of the animal.

As used herein, the term "parasites" includes endo- and ectoparasites. In some embodiments of the present invention, endoparasites can be preferred. In other embodiments, ectoparasites can be preferred. Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention are especially useful for combating parasites of the following orders and species, respectively:

fleas (Siphonaptera), e.g. *Ctenocephalides felis, Ctenocephalides canis; Xenopsylla cheopis, Pulex irritans, Tunga penetrans,* and *Nosopsyllus fasciatus*; cockroaches (*Blattaria-Blattodea*), e.g. *Blattella germanica, Blattella asahinae, Periplaneta americana, Periplaneta japonica, Periplaneta brunnea, Periplaneta fuligginosa, Periplaneta australasiae,* and *Blatta orientalis*; flies, mosquitoes (Diptera), e.g. *Aedes aegypti Aedes albopictus, Aedes vexans, Anastrepha ludens, Anopheles maculipennis; Anopheles cruclans, Anopheles albimanus, Anopheles gambiae, Anopheles freeborni; Anophelesleucosphyrus, Anopheles minithus, Anopheles quadrimaculatus, Calliphora vicina, Chrysomya bezziana, Chrysomya hominivorax, Chrysomya macellaria, Chrysops discalis; Chrysops sllacea, Chrysops atlanticus, Cochliomyia hominivorax, Cordylobia anthropophaga, Culicoides furens, Culex piplens, Culex nigripalpus, Culex quinquefasciatus, Culex tarsalis, Culiseta inomata, Culiseta melanura, Dermatobia hominis; Fannia canicularis; Gasterophilus intestinalis, Glossina morsitans, Glossina palpalis, Glossina fuscipes, Glossina tachinoides, Haematobia irritans, Haplocliplosis equestris; Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimullum mixtum, Sarcophaga haemorrhoidalis; Sarcophaga* sp., *Simulium vittatum, Stomoxys calcitrans, Tabanus bovinus, Tabanus atratus, Tabanus lineola,* and *Tabanus similis*; lice (Phthiraptera), e.g. *Pediculus humanus capitis; Pediculus humanus corporis, Pthirus pubis, Haematopinus eurystemus, Haematopinus suis, Linognathus vituli, Bovicola bovis, Menopon galinae, Menacanthus stramineus* and *Solenopotes capillatus*; ticks and parasitic mites (Parasitiformes): ticks (Ixodida), e.g. *Ixodes scapularis; Ixodes holocyclus, Ixodes pacificus, Rhiphicephalus sanguineus, Dermacentor andersoni Dermacentor variabills; Amblyomma americanum, Ambryomma maculatum, Ornithodorus hermsi; Ornithodorus turicata* and parasitic mites (Mesostigmata), e.g. *Ornithonyssus bacoti* and *Dermanyssus gallinae*, Actinedida (Prostigmata) and Acaridida (Astigmata), e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp; Bugs (Heteropterida): *Cimex lectularius, Cimex hemipterus, Reduvius senilis, Triatoma* spp., *Rhodnius* ssp., *Panstrongylus* ssp., and *Arilus critatus*; Anoplurida, e.g. *Haematopinus* spp., *Linognathus* spp., *Pediculus* spp., *Phtirus* spp., and *Solenopotes* spp.; Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp.; Roundworms Nematoda: Wipeworms and Trichinosis (Trichosyringida), e.g. Trichinellidae (*Trichinella* spp.), (Trichuridae) *Trichuris* spp., *Capillaria* spp.; Rhabditida, e.g. *Rhabditis* spp., *Strongyloides* spp., *Helicephalobus* spp.; Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris; Protostrongylus* spp., *Angiostrongylus* spp., *Parelaphostrongylus* spp., *Aleurostrongylus abstrusus,* and *Dioctophyma renale*; Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi; Camallanida,* e.g. *Dracunculus medinensis* (guinea worm); Spirurida, e.g. *Thelazia* spp., *Wuchereria* spp., *Brugia* spp., *Onchocerca* spp., *Dirofilari* spp. a, *Dipetalonema* spp., *Setaria* spp., *Elaeophora* spp., *Spirocerca lupi,* and *Habronema* spp.; Thorny headed worms (Acanthocephala), e.g. *Acanthocephalus* spp., *Macracanthorhynchus hirudinaceus* and *Oncicola* spp.; Planarians (Plathelminthes): Flukes (Trematoda), e.g. *Faciola* spp., *Fascioloides magna, Paragonimus* spp., *Dicrocoelium* spp., *Fasciolopsis buski; Clonorchis sinensis, Schistosoma* spp., *Trichobilharzla* spp., *Alaria alata, Paragonimus* spp., and *Nanocyetes* spp.; Cercomeromorpha, in particular Cestoda (Tapeworms), e.g. *Diphyllobothnum* spp., *Tenia* spp., *Echinococcus* spp., *Dipylidlum caninum, Multiceps* spp., *Hymenolepis* spp., *Mesocestoides* spp., *Vamplrolepis* spp., *Moniezia* spp., *Anoplocephala* spp., *Sirometra* spp., *Anoplocephala* spp., and *Hymenolepis* spp.

As used herein, the term "animal" includes warm-blooded animals (including humans) and fish. Preferred are mammals, such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels. Particularly preferred are domestic animals, such as dogs or cats.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally, it is favorable to apply the compounds of the present invention in total amounts of 0.5 mg/kg to 100 mg/kg per day, preferably 1 mg/kg to 50 mg/kg per day.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further auxiliaries such as acids, bases, buffer salts, preservatives, and solubilizers. Suitable auxiliaries for injection solutions are known in the art. The solutions are filtered and filled sterile.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Gels are applied to or spread on the skin or introduced into body cavities. Gels are prepared by treating solutions which have been prepared as described in the case of the injection solutions with sufficient thickener that a clear material having an ointment-like consistency results. Suitable thickeners are known in the art.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added. Suitable such auxiliaries are known in the art.

Emulsions can be administered orally, dermally or as injections. Emulsions are either of the water-in-oil type or of the oil-in-water type. They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances. Suitable hydrophobic phases (oils), suitable hydrophilic phases, suitable emulsifiers, and suitable further auxiliaries for emulsions are known in the art.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers. Suitable suspending agents, and suitable other auxiliaries for suspensions including wetting agents are known in the art.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form. Suitable auxiliaries for this purpose are known in the art.

The compositions which can be used in the invention can comprise generally from about 0.001 to 95% of the compound of the present invention.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

Topical application may be conducted with compound-containing shaped articles such as collars, medallions, ear tags, bands for fixing at body parts, and adhesive strips and foils.

Generally it is favorable to apply solid formulations which release compounds of the present invention in total amounts of 10 mg/kg to 300 mg/kg, preferably 20 mg/kg to 200 mg/kg, most preferably 25 mg/kg to 160 mg/kg body weight of the treated animal in the course of three weeks.

EXAMPLES

With appropriate modification of the starting materials, the procedures as described in the preparation examples below were used to obtain further compounds of formula I. The compounds obtained in this manner are listed in the table X that follows, together with physical data.

Compounds can be characterized e.g. by coupled High Performance Liquid Chromatography/mass spectrometry (HPLC/MS), or by $^1$H-NMR and/or by their melting points.

Example-(C-1)

3-(cyanomethyl)-8-methyl-7-oxo-6-phenyl-2,3-dihydrothiazolo[3,2-a]pyrimidin-4-ium-5-olate (C-1)

Step 1: 4-amino-2-(tert-butoxycarbonylamino)-4-oxo-butanoic acid

To Compound of DL-Asparagine monohydrate (15.0 gm, 0.114 mol) in 1,4 Dioxane (150 ml) and water (150 ml) was added sodium carbonate (14.44 gm, 0.136 mol) and Di-tert butyl-dicarbonate (31.29 ml, 0.136 ma). Then reaction mass was stirred for 16 hr. at ambient temperature. Progress of reaction was monitored by TLC. After completion of reaction, reaction mass was concentrate under reduced pressure until 1,4-dioxane was evaporated. Then pH adjusted to 2 with 37% HCl to give white solid that was filtered, washed with water and dried under reduced pressure to afford 25.0 g (94.8% yield) of title compound as a solid.

$^1$H NMR (DMSO-$d_6$, 500 MHz) δ=12.5 (s, 1H), 7.31 (s, 1H), 6.88 (t, J=14 Hz, 2H), 4.25-4.21 (m, 1H), 2.51-2.40 (m, 2H), 1.38 (s, 1H).

Step 2: ethyl 2-(tert-butoxycarbonylamino)-3-cyano-propanoate

To the product of step-1 (15.0 gm, 0.065 mol) in DCM (150 ml) and Ethanol (15 ml) was added EDC.HCl (37.4 gm, 0.194 mol) and 4-Dimethylaminopyridine (1.57 gm, 0.013 ml) 0° C. after addition Reaction mass was stirred for 16 hr. at ambient temperature. Progress of reaction was monitored by TLC. After completion of reaction, reaction mass was diluted with water (200 ml) and followed by extracting in ethyl acetate (100 ml×3). The combined organic extracts were dried over Na$_2$SO$_4$, filtered and concentrated under reduced pressure. The crude product was purified by flash chromatography (eluting in 0-30% ethyl acetate in heptane as a mobile phase) to afford 7.0 gm (44.7% yield) of title compound as a solid.

$^1$H NMR (DMSO-$d_6$, 300 MHz) δ=7.65 (d, J=8.4, 1H), 4.35-4.27 (m, 1H), 4.14-4.07 (m, 2H), 2.29-2.80 (m, 2H), 1.36 (s, 10H), 1.18 (t, J=7.2, 3H).

Step 3: tert-butyl N-[1-(cyanomethyl)-2-hydroxy-ethyl]carbamate

To the product of step-2 (1.8 gm, 0.007 mol) in dry THF (15 ml) was added Lithium borohydride 2M (1.85 ml, 0.004 mol) at 0° C. Then reaction mass was heated at 70° C. for 2 hr. Progress of reaction was monitored by TLC. After completion of reaction, reaction mass was cooled to room temp and acidified with 2M KHSO$_4$ solution to pH 4. After filtration, Filtrate was extracted in ethyl acetate (30 ml×3). The combined organic extracts were dried over Na$_2$SO$_4$, filter and concentrated under reduced pressure. The crude product was purified by flash chromatography (eluting in 0-50% ethyl acetate in heptane as a mobile phase) to afford 1.3 gm (87.4% yield) of title compound as a liquid.

$^1$H NMR (DMSO-$d_6$, 300 MHz) δ=6.98 (d, J=8.4, 1H), 4.95-4.91 (m, 1H), 3.65-3.67 (m, 1H), 3.43-3.24 (m, 2H), 2.75-2.55 (m, 1H), 1.39 (s, 9H).

Step 4: 3-amino-4-hydroxy-butanenitrile

To the product of step-3 (0.500 gm, 0.002 mol) in Methanol (5 ml) was added 3M Methanolic HCl (5 ml). Reaction mass was stirred for 16 hr. at ambient temperature. Progress of reaction was monitored by TLC. After completion of reaction, reaction mass was concentrated under reduced pressure. diluted with DCM (10 ml) Then added 3M Methanolic ammonia at 0° C. NH$_4$Cl was formed, Filtered it and filtrate was concentrated under reduced pressure to afford 0.200 gm (80.0% yield) of title compound as a Liquid.

$^1$H NMR (CDCl$_3$-$d_6$, 500 MHz) δ=3.68-3.57 (m, 2H), 3.28-3.23 (m, 1H), 2.58-2.45 (m, 2H). Step 5: 1-[1-(cyanomethyl)-2-hydroxy-ethyl]-3-methyl-thiourea To the product of step-4 (0.764 gm, 0.008 mol) in dry THF (10 ml) was added Methyl Isothiocyanate (0.837 gm, 0.011 mol) at 0'C. Reaction mass was stirred for 16 hr. at ambient temperature. Progress of reaction was monitored by TLC. After completion of reaction, Reaction mass was concentrated under reduced pressure to afford crude 1.20 gm (90.8% yield) of title compound as a viscous liquid.

LC/MS (method 1): R$_t$: 0.84 min; MS: m/z=174.2 (M$^{+1}$).

Step 6: 2-[(2Z)-2-methyliminothiazolidin-4-yl]acetonitrile

To the product of step-5 (1.20 gm, 0.007 mol) in dry THF (10 ml) was added 1,1'Carbonyldiimidazole (1.68 gm, 0.010 mol) at room temperature. Reaction mass was stirred for 16 hr. at ambient temperature. Progress of reaction was monitored by TLC. After completion of reaction, reaction mass was concentrate under reduced pressure. The crude product was purified by flash chromatography (eluting in 0-80% ethyl acetate in heptane as a mobile phase) to afford 0.500 gm (46.5% yield) of title compound as a solid.

LC/MS (method 1): R$_t$: 0.48 min; MS: m/z=156.2 (M$^{+1}$).

Step 7: 3-(cyanomethyl)-8-methyl-7-oxo-6-phenyl-2,3-dihydrothiazolo[3,2-a]pyrimidin-4-ium-5-olate (C-1)

To the product of step-6 (0.200 gm, 0.001 mol) in Toluene (5 ml) was heated at 105° C. for 15 min. Then added Activated ester (0.517 gm 0.001 mol) at same temperature. Then reaction mass was heated at 110° C. for 2 hr. Progress of reaction was monitored by TLC. After completion of reaction, reaction mass was cooled to room temperature, concentrated under reduced pressure. The crude product was purified by flash chromatography (eluting in 0-100% ethyl acetate in heptane as a mobile phase) to afford 0.080 gm (20.5% yield) of title compound as a solid.

LC/MS (method 1): R$_t$: 1.18 min; MS: m/z=300.0 (M$^{+1}$).
$^1$H NMR (DMSO-$d_6$, 500 MHz) δ=7.62 (dd J=1.5, 7 Hz, 2H). 7.45 (dd, J=7.5, 7.5 Hz, 2H), 7.09 (dd, J=7.5, 7 Hz, 1H), 4.41-4.39 (m, 1H), 4.10-4.08 (m, 1H), 3.62-3.59 (m, 1H), 3.41 (s, 3H), 3.31-3.21 (m, 1H), 3.19-3.15 (m, 1H), Examples of compound of formula I given in table Z were prepared using the method analogous to preparation of the above examples or by derivatization of the above examples or intermediates thereof, or using the method analogous to the methods mentioned in the general procedure.

TABLE Z

| Example | Structure | ¹H NMR |
|---|---|---|
| C-1 | 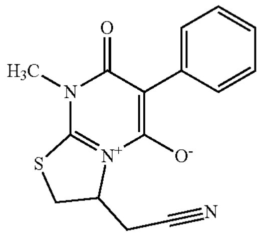 [SMILES: Cn1c2[n+](c([O-])c(-c3ccccc3)c1=O)C(CC#N)CS2] | ¹H NMR (DMSO-$d_6$, 500 MHz) δ = 7.62 (dd J = 1.5, 7 Hz, 2H). 7.45 (dd, J = 7.5, 7.5Hz, 2H), 7.09 (dd, J = 7.5, 7Hz, 1H), 4.41-4.39 (m, 1H), 4.10-4.08 (m, 1H), 3.62-3.59(m, 1H), 3.41 (s, 3H), 3.31-3.21 (m, 1H), 3.19-3.15 (m, 1H), |
| C-2 | 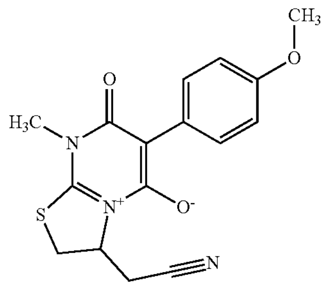 | ¹H NMR (DMSO-$d_6$, 500 MHz) δ = 7.55 (d J = 8Hz, 2H). 6.82 (d, J = 8.5Hz, 2H), 7.5, 7.5Hz, 4.39-4.38 (m, 1H), 4.09-4.05 (m, 1H), 3.75 (s, 3H), 3.61-3.59 (m, 1H), 3.51-3.15 (m, 5H). |
| C-3 | 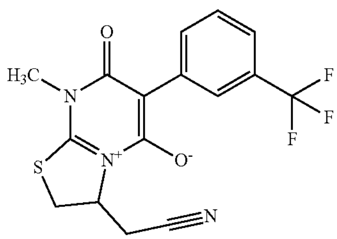 [SMILES: Cn1c2[n+](c([O-])c(-c3cccc(C(F)(F)F)c3)c1=O)C(CC#N)CS2] | ¹H NMR (DMSO-$d_6$, 500 MHz) δ = 8.12 (s, 1H), 8.05 (d, J = 8 Hz, 1H), 7.54-7.41 (m, 2H), 5.43-5.42 (m, 1H), 4.11-4.06 (m, 1H), 3.61-3.63 (m, 1H), 3.43-3.40 (m, 4H), 3.20-3.16 (m, 1H). |
| C-4 | 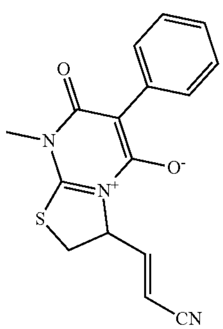 [SMILES: Cn1c2[n+](c([O-])c(-c3ccccc3)c1=O)C(/C=C/C#N)CS2] | ¹H NMR (500 MHz, DMSO-$d_6$) δ 7.55 (d, J = 7.4 Hz, 2H), 7.17 (t, J= 7.6 Hz, 2H), 7.11-6.70 (m, 2H), 6.06-5.84 (m, 1H), 5.72 (dd, J = 15.3, 8.2 Hz, 1H), 4.05 (ddd, J = 46.3,11.7, 8.8 Hz, 1H), 3.66-3.41 (m, 1H), 3.35 (d, J = 7.7 Hz, 3H). |

Biological Tests

The biological activity of the compounds of formula (I) of the present invention can be evaluated in biological tests as described in the following.

General conditions: If not otherwise specified, the test solutions are prepared as follows:

The active compound is dissolved at the desired concentration in a mixture of 1:1 (vol:vol) distilled water: acetone. The test solution is prepared at the day of use.

Test solutions are prepared in general at different concentrations (wt/vol).

Orchid Thrips (*Dichromothrips corbetti*)

*Dichromothrips corbetti* adults used for bioassay are obtained from a colony maintained continuously under laboratory conditions. For testing purposes, the test compound is diluted in a 1:1 mixture of acetone:water (vol:vol), plus 0.01% vol/vol Alkamuls® EL 620 surfactant.

Thrips potency of each compound is evaluated by using a floral-immersion technique. Plastic petri dishes are used as test arenas. All petals of individual, intact orchid flowers are dipped into treatment solution and allowed to dry. Treated flowers are placed into individual petri dishes along with about 20 adult thrips. The petri dishes v then covered with lids. All test arenas are held under continuous light and a temperature of about 28° C. for duration of the assay. After 3 days, the numbers of live thrips are counted on each flower, and along inner walls of each petri dish. The percent mortality is recorded 72 hours after treatment.

In this test, compound C1 at 500 ppm showed over 75% mortality in comparison with untreated controls Rice Green Leafhopper (*Nephotettix virescens*)

Rice seedlings are cleaned and washed 24 hours before spraying. The active compounds are formulated in 50:50 acetone:water (vol:vol), and 0.1% vol/vol surfactant (EL 620) is added. Potted rice seedlings are sprayed with 5 ml test solution, air dried, placed in cages and inoculated with 10 adults. Treated rice plants are kept at about 28-29° C. and relative humidity of about 50-60%. Percent mortality is recorded after 72 hours.

In this test, compound C1 at 500 ppm showed over 75% mortality in comparison with untreated controls Rice Brown Plant Hopper (*Nilaparvata lugens*)

Rice seedlings are cleaned and washed 24 hours before spraying. The active compounds are formulated in 50:50 acetone:water (vol:vol) and 0.1% vol/vol surfactant (EL 620) is added. Potted rice seedlings are sprayed with 5 ml test solution, air dried, placed in cages and inoculated with 10 adults. Treated rice plants are kept at about 28-29° C. and relative humidity of about 50-60%. Percent mortality is recorded after 72 hours.

In this test, compound C1 at 500 ppm showed over 75% mortality in comparison with untreated controls

The invention claimed is:
1. A substituted pyrimidinium compound of formula (I)

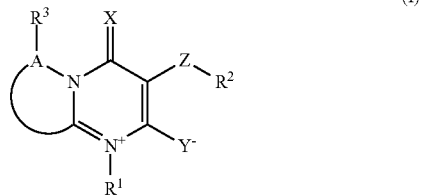

(I)

wherein

X, Y are each independently O or S;

Z is a direct bond, O, $S(O)_m$, $NR^b$, $C(R^a R^{aa})O$, $C(=X^1)$, $C(=X^1)Y^1$, or $Y^1C(=X^1)$;

$X^1$ is O, S, or $NR^b$;

$Y^1$ is O, S, or $NR^c$;

A is CH or N and, wherein the nitrogen of the pyrimidinium ring taken together with the contiguous linking carbon atom and A as depicted in formula (I), form a four- to seven-membered ring, wherein each remaining ring member is selected from carbon atoms and up to 3 heteroatoms independently selected from up to 2 O, up to 2 S, and up to 3 $N(R^c)_p$, wherein up to 2 carbon atom ring members are independently selected from the group consisting of $C(=O)$ and $C(=S)$, and the sulfur atom ring members are independently selected from $S(=O)_m$, wherein each ring may be substituted with up to 3 $R^a$;

$R^3$ is $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_7$-cycloalkyl, $C_3$-$C_7$-halocycloalkyl, $C_4$-$C_8$-alkylcycloalkyl, $C_4$-$C_8$-haloalkylcycloalkyl, $C_4$-$C_8$-cycloalkylalkyl, $C_4$-$C_8$-halocycloalkylalkyl, $C_1$-$C_6$-alkoxy, $C_1$-$C_6$-haloalkoxy, $C_2$-$C_6$-alkylcarbonyl, $C_2$-$C_6$-haloalkylcarbonyl, each substituted with at least one substituent selected from CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or $N=S(=O)_pR^cR^c$, or $R^3$ is phenyl optionally substituted with one or more substituents selected from halogen, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or $N=S(=O)_pR^cR^c$, or $R^3$ is phenyl optionally substituted with one or more substituents selected from $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_7$-cycloalkyl, $C_3$-$C_7$-halocycloalkyl, $C_4$-$C_8$-alkylcycloalkyl, $C_4$-$C_8$-haloalkylcycloalkyl, $C_4$-$C_8$-cycloalkylalkyl, $C_4$-$C_8$-halocycloalkylalkyl, $C_1$-$C_6$-alkoxy, $C_1$-$C_6$-haloalkoxy, $C_2$-$C_6$-alkylcarbonyl, $C_2$-$C_6$-haloalkylcarbonyl, which groups may optionally be substituted with halogen, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)Rb$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or $N=S(=O)_pR^cR^c$, $R^1$ is hydrogen, $C_1$-$C_8$-alkyl, $C_2$-$C_8$-alkenyl, $C_2$-$C_8$-alkynyl, $C_3$-$C_{10}$-cycloalkyl, $C_4$-$C_{10}$-cycloalkenyl, $C_5$-$C_{14}$-cycloalkylcycloalkyl or $R^1$ may form a three- to eleven-membered saturated, or partially unsaturated or aromatic carbo-or heterocyclic ring or ring system, which may contain 1 to 4 heteroatoms selected from $N(R^c)_p$, O, and S, wherein S may be oxidized, and wherein the aforementioned groups and the carbo- or heterocyclic rings system may be unsubstituted, partially or fully substituted with $R^a$; or $R^1$ is $C(=O)R^b$, $C(=O)OR^e$, $NR^bR^c$, $C(=O)NR^bR^c$, $C(=S)NR^bR^c$, $SO_2NR^bR^c$, $OC(=O)R^c$, $OC(=O)OR^e$, $OC(=O)NR^bR^e$, $N(R^c)C(=O)R^c$, $N(R^c)C(=O)OR^e$, $N(R^c)C(=O)NR^bR^c$, $NR^cSO_2R^b$, $NR^cSO_2NR^bR^c$, $Si(R^d)_3$, $C(=NR^c)R^c$, $C(=NOR^c)R^c$, $C(=NNR^bR^c)R^c$, $C(=NN(C(=O)R^b)R^c)R^c$, $C(=NN(C(=O)OR^c)(R^c)_2$, $S(=O)_o(=NR^b)_qR^c$ or $N=CR^bR^c$;

$R^a$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $N=S(=O)_pR^cR^c$, $S(=O)_o(=NR^b)_qR^c$, $SF_5$, OCN, SCN, $Si(R^d)_3$ or a three- to six-membered saturated, or partially unsaturated or aromatic carbo- or heterocyclic ring, which may contain 1 to 3 heteroatoms selected from $N$-$(R^c)_p$, O, and S which may be oxidized, and wherein the aforementioned groups and the carbo- or heterocyclic ring may be partially or fully substituted with $R^{aa}$, or two geminally bound groups $R^a$ together may form a group selected from the group consisting of =O, =S, =$CR^bR^c$, =$NR^c$, =$NOR^c$, and =$NNR^cR^c$;

$R^{aa}$ is each independently halogen, $C_1$-$C_6$-alkyl, $C_1$-$C_6$-haloalkyl, $C_1$-$C_6$-alkoxy or $C_1$-$C_6$-haloalkoxy;

$R^b$ is each independently hydrogen, $C_1$-$C_6$-alkyl, $C_1$-$C_6$-haloalkyl, $C_1$-$C_6$-alkoxy, $C_1$-$C_6$-haloalkoxy or a three- to six-membered saturated, or partially unsaturated or aromatic carbo- or heterocyclic ring, which may contain 1 to 3 heteroatoms selected from $N(R^c)_p$, O, and S, wherein S may be oxidized and which carbo- or heterocyclic ring may be partially or fully substituted with $R^{aa}$;

$R^c$ is each independently hydrogen, $C_1$-$C_4$-alkyl, $C_1$-$C_4$-haloalkyl, $C_1$-$C_4$-alkylcarbonyl, $C_1$-$C_6$ cycloalkyl, or a three- to six-membered saturated, partially unsaturated or aromatic carbo- or heterocyclic ring, which may contain 1 to 3 heteroatoms selected from $N(R^{aa})_p$, O and S, wherein S may be oxidized and wherein the carbo- or heterocyclic ring may be partially or fully substituted with $R^{aa}$;

wherein two geminally bound groups $R^bR^b$, $R^cR^b$ or $R^cR^c$ together with the atom to which they are bound, may form a 3-, 4-, 5-, 6- or 7-membered saturated, partially unsaturated or aromatic carbo- or heterocyclic ring, which may contain 1 to 2 heteroatoms or heteroatoms groups selected from N, O, S, NO, SO and $SO_2$ and wherein the carbo- or heterocyclic ring may be partially or fully substituted with $R^4$;

$R^d$ is each independently hydrogen, phenyl, $C_1$-$C_6$-alkyl, $C_2$-$C_6$-alkenyl, $C_2$-$C_6$-alkynyl, $C_3$-$C_8$-cycloalkyl, or $C_1$-$C_6$-alkoxyalkyl, wherein the above mentioned groups may be substituted with one or more halogen;

$R^e$ is each independently, $C_1$-$C_4$-alkyl, $C_1$-$C_4$-haloalkyl, $C_1$-$C_4$-alkylcarbonyl, $C_1$-$C_6$ cycloalkyl, or a three- to six-membered saturated, partially unsaturated or aromatic carbo- or heterocyclic ring, which may contain 1 to 3 heteroatoms selected from $N(R^{aa})_p$, O and S, wherein S may be oxidized and wherein the carbo- or heterocyclic ring may be partially or fully substituted with $R^{aa}$;

n is 0, 1 or 2;
m is 0, 1, or 2;
p is 0 or 1;

$R^2$ is H, halogen, CN, $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, or $C_3$-$C_6$ cycloalkenyl, wherein the aforementioned groups may be unsubstituted, partially, or fully substituted with $R^{2a}$, or $R^2$ may form a carbo-or heterocyclic three- to ten-membered ring or a seven- to eleven-membered rings system, which ring or ring system may be saturated, partially unsaturated, or aromatic, and which ring or ring system may contain 1 to 4 heteroatoms selected from $N(R^c)_p$, O, and S, wherein S may be oxidized, and wherein the carbo- or heterocyclic ring or rings system may be unsubstituted, partially, or fully substituted with Rea;

with the proviso that if $R^2$ is halogen or CN, then Z is a direct bond;

$R^{2a}$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_p$ $R^c$, $OC(=O)(O)_pR^e$, $C(=O)NR^bR^b$, $OC(=O)$ $NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)$ $R^b$, $C(=NNR^bR^c)R^b$, $C(=NN(C(=O)O_pR^c)R^c)R^b$, ON=$CR^bR^c$, $ONR^bR^c$, $S(=O)_o(=NR^b)_qR^c$, $SO_2NR^b(=O)NR^bR^c$, $P(=X^2)R^bR^c$, $OP(=X^2)$ $(O_pR^c)R^b$, $OP(=X^2)(OR^c)_2$, N=$CR^bR^c$, $NR^bN$=$CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, N=$S(=O)_pR^cR^c$, or a three- to six-membered saturated, or partially unsaturated or aromatic carbo- or heterocyclic ring, which may contain 1 to 3 heteroatoms selected from N—$(R^c)_p$, O, and S, wherein S may be oxidized, and wherein the aforementioned groups and the carbo- or heterocyclic ring may be partially or fully substituted with $R^{2aa}$ or two geminally bound groups $R^{2a}$ together may form a group selected from the group consisting of =O, =S, =$CR^bR^c$, =$NR^c$, =$NOR^c$, and =$NNR^cR^c$;

$R^{2aa}$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_p$ $R^c$, $OC(=O)(O)_pR^e$, $C(=O)NR^bR^b$, $OC(=O)$ $NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^c)R^b$, ON=$CR^bR^c$, $ONR^bR^c$, $S(=O)_o(=NR^b)_qR^c$, $SO_2NR^b(=O)NR^bR^c$, $P(=X^2)R^bR^c$, $OP(=X^2)$ $(O_pR^c)R^b$, $OP(=X^2)(OR^c)_2$, N=$CR^bR^c$, $NR^bN$=$CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or N=$S(=O)_pR^cR^c$ or two geminally bound groups $R^{2aa}$ together may form a group selected from the group consisting of =O, =S, =$CR^bR^c$, =$NR^c$, =$NOR^c$, and =$NNR^cR^c$;

$X^2$ is independently O or S;

$R^4$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, ON=$CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, N=$CR^bR^c$, $NR^bN$=$CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or N=$S(=O)_pR^cR^c$ or two geminally bound groups $R^4$ together may form a group selected from the group consisting of =O, =S, =$CR^bR^c$, =$NR^c$, =$NOR^c$, and =$NNR^cR^c$;

or a stereoisomer, tautomer, salt, or N-oxide thereof.

2. The compound of formula (I) of claim 1 or a stereoisomer, tautomer, salt, or N-oxide thereof, wherein X and Y are O.

3. The compound of formula (I) of claim 1 or a stereoisomer, tautomer, salt, or N-oxide thereof, wherein $R^3$ is $C_1$-$C_4$-alkyl or $C_1$-$C_4$-haloalkyl, each substituted with at least one substituent selected from cyano.

4. The compound of formula (I) of claim 1 or a stereoisomer, tautomer, salt, or N-oxide thereof of, wherein A is CH or N, wherein the nitrogen of the pyrimidinium ring taken together with the contiguous linking carbon atom and A as depicted in formula (I), form a five or six membered ring, wherein each remaining ring member is selected from carbon atoms and up to one heteroatom selected from the group consisting of O, S and $N(R^c)_p$, which ring may be substituted with $R^a$.

5. The compound of formula (I) of claim 1 or a stereoisomer, tautomer, salt, or N-oxide thereof, wherein
Z is a direct bond, and
$R^2$ is a six membered carbo- or heterocyclic ring, which ring may be unsubstituted, partially, or fully substituted with $R^{2a}$, and wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl, which may be substituted with halogen, $C_1$-$C_6$-haloalkyl or $C_1$-$C_6$-haloalkoxy.

6. The compound of formula (I) of claim 1 or a stereoisomer, tautomer, salt, or N-oxide thereof, wherein
Z is a direct bond, and
$R^2$ is phenyl, which is optionally substituted with halogen, $C_1$-$C_4$-haloalkyl, and/or $C_1$-$C_4$-haloalkoxy.

7. The compound of formula (I) of claim 1 or a stereoisomer, tautomer, salt, or N-oxide thereof, wherein
$R^1$ is $C_1$-$C_4$-alkyl, $C_3$-$C_6$-cycloalkyl, $C_2$-$C_4$-alkenyl, benzyl or phenyl, which groups may be partially or fully substituted with halogen or $C_1$-$C_4$-alkyl.

8. The compound of formula (I) of claim 3 or a stereoisomer, tautomer, salt, or N-oxide thereof, wherein
X, Y are each O;
A is CH and the nitrogen of the pyrimidinium ring taken together with the contiguous linking carbon atom and A as depicted in formula (I), form a five or six membered ring, wherein each remaining ring member is selected from 2 and 3 carbon atoms;
$R^1$ is $CH_3$, $CH_2CH_3$, isopropyl, cyclopropyl, $CH_2CF_3$, phenyl, allyl or benzyl;
$R^2$ is phenyl which may be substituted with halogen, $C_1$-$C_6$-haloalkyl, $C_1$-$C_6$-haloalkoxy or phenyl;
Z is a direct bond and
$R^3$ is cyanoethyl or cyanomethyl.

9. The compound of formula (I) of claim 3 or a stereoisomer, tautomer, salt, or N-oxide thereof, wherein the cyano is $CH_2$—CN or $CH_2$—$CH_2$—CN.

10. The compound of formula (I) of claim 3 or a stereoisomer, tautomer, salt, or N-oxide thereof, wherein the cyano is $CH_2$—CN.

11. The compound of formula (I) of claim 2 or a stereoisomer, tautomer, salt, or N-oxide thereof, wherein A is CH or N, wherein the nitrogen of the pyrimidinium ring taken together with the contiguous linking carbon atom and A as depicted in formula (I), form a five or six membered ring, wherein each remaining ring member is selected from carbon atoms and up to one heteroatom selected from the group consisting of O, S and $N(R^c)_p$, which ring may be substituted with $R^a$.

12. The compound of formula (I) of claim 2 or a stereoisomer, tautomer, salt, or N-oxide thereof, wherein
Z is a direct bond, and
$R^2$ is a six membered carbo- or heterocyclic ring, which ring may be unsubstituted, partially, or fully substituted with $R^{2a}$, and wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl, which may be substituted with halogen, $C_1$-$C_6$-haloalkyl or $C_1$-$C_6$-haloalkoxy.

13. The compound of formula (I) of claim 2 or a stereoisomer, tautomer, salt, or N-oxide thereof, wherein
Z is a direct bond, and
$R^2$ is phenyl, which is optionally substituted with halogen, $C_1$-$C_4$-haloalkyl, and/or $C_1$-$C_4$-haloalkoxy.

14. A composition comprising at least one compound of formula (I) of claim 1 and at least one inert liquid and/or solid carrier.

15. A seed comprising a compound of formula (I) of claim 1 or a stereoisomer, tautomer, salt, or N-oxide thereof in an amount of from 0.1 g to 10 kg per 100 kg of seed.

16. A method for protecting crops, plants, plant propagation material and/or growing plants from attack or infestation by invertebrate pests comprising contacting or treating the crops, plants, plant propagation material and growing plants, or soil, material, surface, space, area or water in which the crops, plants, plant propagation material is stored or the plant is growing with a pesticidally effective amount of at least one compound of formula (I) of claim 1 or a stereoisomer, tautomer, salt, or N-oxide thereof.

17. A method for combating, controlling, preventing or protecting against infestation or infection by invertebrate pest, which method comprises contacting said pest or its food supply, habitat or breeding grounds with a pesticidally effective amount of at least one compound of formula (I) of claim 1 or a stereoisomer, tautomer, salt, or N-oxide thereof.

18. A non-therapeutic method for treating animals infested or infected by parasites or preventing animals of getting infected or infested by parasites or protecting animals against infestation or infection by parasites which comprises orally, topically or parenterally administering or applying to the animals a parasiticidally effective amount of a compound of formula (I) of claim 1 or a stereoisomer, tautomer, salt, or N-oxide thereof.

19. A method for combating, controlling, preventing or protecting against infestation or infection by invertebrate pest, which method comprises contacting said pest or its food supply, habitat or breeding grounds with a pesticidally effective amount of at least one compound of formula (I) or a stereoisomer, tautomer, salt, or N-oxide thereof a composition of claim 14.

20. A method for protecting crops, plants, plant propagation material and/or growing plants from attack or infestation by invertebrate pests comprising contacting or treating the crops, plants, plant propagation material and growing plants, or soil, material, surface, space, area or water in which the crops, plants, plant propagation material is stored or the plant is growing with a composition of claim 14.

* * * * *